US011525135B2

(12) United States Patent
Bonnin et al.

(10) Patent No.: US 11,525,135 B2
(45) Date of Patent: Dec. 13, 2022

(54) TLR3 LIGANDS THAT ACTIVATE BOTH EPITHELIAL AND MYELOID CELLS

(71) Applicant: TOLLYS, Lyons (FR)

(72) Inventors: Marc Bonnin, Lyons (FR); Sylvain Thierry, Lyons (FR)

(73) Assignee: TOLLYS, Lyons (FR)

( * ) Notice: Subject to any disclaimer, the term of this patent is extended or adjusted under 35 U.S.C. 154(b) by 61 days.

(21) Appl. No.: 16/675,846

(22) Filed: Nov. 6, 2019

(65) Prior Publication Data

US 2020/0080084 A1 Mar. 12, 2020

Related U.S. Application Data

(63) Continuation-in-part of application No. PCT/EP2019/061591, filed on May 6, 2019.

(30) Foreign Application Priority Data

May 4, 2018 (EP) .................................... 18305561

(51) Int. Cl.

| | |
|---|---|
| ***C12N 15/113*** | (2010.01) |
| ***A61P 35/00*** | (2006.01) |
| ***C07K 16/28*** | (2006.01) |

(52) U.S. Cl.

CPC ............ *C12N 15/113* (2013.01); *A61P 35/00* (2018.01); *C07K 16/2818* (2013.01)

(58) Field of Classification Search

CPC ............ A61K 2039/5154; A61P 37/04; C12N 5/0639; C12N 15/111; C12N 2330/30; C12N 2501/24

USPC ................. 435/6.1, 91.1, 455, 458; 536/23.1

See application file for complete search history.

(56) References Cited

U.S. PATENT DOCUMENTS

| | | | |
|---|---|---|---|
| 7,378,249 B2 | 5/2008 | Andre et al. | |
| 9,814,740 B2 | 11/2017 | Tedder et al. | |
| 10,023,871 B2 | 7/2018 | Rohayem | |
| 2004/0253722 A1* | 12/2004 | Adams .................... | A61P 37/02 435/372 |
| 2011/0076296 A1 | 3/2011 | Aubin et al. | |
| 2020/0147132 A1* | 5/2020 | Dheda ..................... | A61P 37/04 |

FOREIGN PATENT DOCUMENTS

WO WO-2006054177 A1 * 5/2006 .............. A61P 35/04

OTHER PUBLICATIONS

European Search Report for Foreign Application No. EP18305561.5, dated Nov. 6, 2018 European Patent Office, Rijswiki, NL.

International Search Report for International Application No. EP18305561.5, dated Jul. 30, 2019 European Patent Office, Rijswikj, NL.

Botos I. et al. "The Toll-like receptor 3:dsRNA Signaling complex.", vol. 1789, No. 9-10, pp. 667-674, 2009 Biuochimica et Biophysica Acta. Gene Regulatory Mechanisms, Elsevier, Amsterdam.

Marit Bugge et al., "Surface Toll-like receptor 3 expression in metastatic intestinal epithelial cells induces inflammatory cytokine production and promotes invasiveness", Journal of Biological Chemistry, vol. 292, No. 37, 2017, pp. 15408-15425.

* cited by examiner

*Primary Examiner* — Jane J Zara

(74) *Attorney, Agent, or Firm* — BCF LLP

(57) ABSTRACT

The invention relates to a composition comprising a double-stranded RNA (dsRNA) having two complementary strands, comprising at least one block of poly A and the complementary block of poly U, each strand having a length of between 50 and 200 bases, preferably between 55 and 200 bases, and a pharmaceutically acceptable vehicle, carrier or excipient, for use in a method of treating a cancer expressing a TLR3 receptor.

20 Claims, 22 Drawing Sheets

Figure 1:
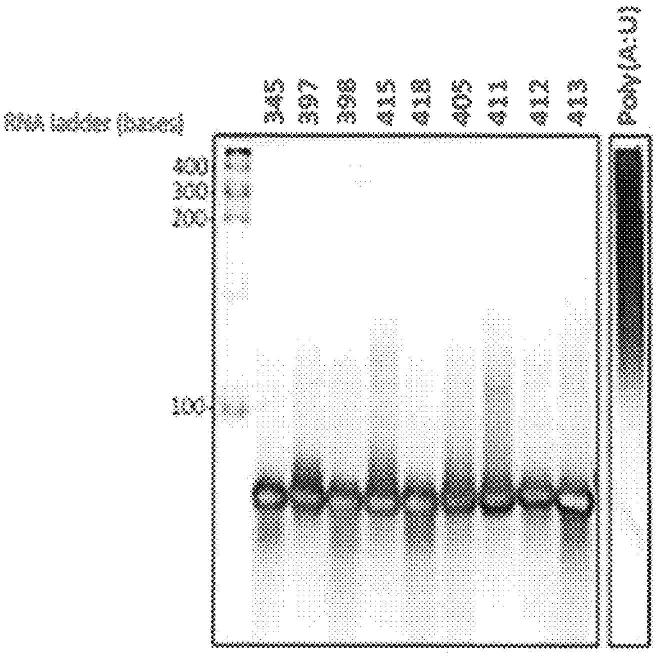

Specification includes a Sequence Listing.

TLR3 LIGANDS THAT ACTIVATE BOTH EPITHELIAL AND MYELOID CELLS

CROSS-REFERENCE TO RELATED APPLICATIONS

This patent application is a Continuation-in-Part of PCT/EP2019/061591 filed on May 6, 2019, which claims the benefit of Eur. Pat. App. 18305561.5 filed May 4, 2018, all of said applications incorporated herein by reference.

ELECTRONIC FILE—SEQUENCE LISTING

This application hereby incorporates by reference the material of the electronic Sequence Listing filed concurrently herewith. The material in the electronic Sequence Listing is submitted as a text (.txt) file entitled "105712-012-Sequence Listing— 2022-05-12_ST25.txt" created on May 12, 2022, which has a file size of 33 KB, and is herein incorporated by reference in its entirety.

The present invention relates to a pharmaceutical composition comprising short and defined double-stranded RNA (dsRNA) having two complementary strands, comprising one strand comprising at least one bloc of a Poly A and a complementary strand comprising the complementary bloc of Poly U, and possibly chimeric forms with other nucleotides among A, U, G, I or C. It also relates to such a composition for use in treating a TLR3 positive cancer and to related methods of treatment. It specifically relates to dsRNA acting as TLR3 ligands and activating both epithelial and myeloid cells.

The present invention also relates to the use of these compositions for treating certain forms of bladder cancer, and to method of treatment of these bladder cancers with these compositions.

The present invention further relates to the combined use or therapy of such composition and of an Immune Check Point Inhibitor or composition containing it, in particular a monoclonal antibody directed against PD-1 or against PD-L1.

BACKGROUND

TLR3 is a pattern recognition receptor expressed mostly in endo-lysosomes that appears to be dedicated to the detection of viral infection through the binding of dsRNA. Indeed, dsRNA produced by virus either as their genomic material (dsRNA viruses) or as intermediates of their life cycle (ssRNA viruses, DNA viruses) have been shown to activate TLR3. Moreover, several vertebrate endogenous dsRNA liberated during tissue destruction have been found to activate TLR3. In addition, synthetic dsRNA have been designed that activate TLR3 as well. They include the Poly(I:C), Poly (A:U) and variants thereof such as Polyl:PolyC12U (Ampligen®)

Extensive experiments with dsRNA, including TLR3-binding assays and TLR3-dependant signaling assays with wild-type and mutants of TLR3, crystallography studies with dsRNA-bound TLR3 and in vivo analysis of dsRNA response in wild-type and $TLR3^{-/-}$ mice have all contributed to defining the structural features required to activate TLR3 (Botos, I. et al., *Biochim. Biophys. Acta* 1789, 667-674, 2009). Agonist ligands for TLR3 are dsRNA with the following features: (1) the dsRNA must be composed of unmodified ribose, that may include inosines; (2) the exact sequence does not appear to be crucial; (3) a minimal length of approximately 50 bp (48 Å) appears to be imposed by the distance between the RNA-binding sites on the extracellular domains of TLR3 in the homodimers that represent the signaling units; (4) single strand RNAs that fold and form stem-loop structure can also activate TLR3; (5) dsRNA must first be efficiently internalized within the cells, i.e. through scavenger receptors binding, before triggering TLR3 dimerization which represents the first step of signaling. In contrast with Poly(A:U) that appears to be highly specific for TLR3 in human, Poly(I:C) also binds and activates the cytosolic dsRNA receptors RIG-I, MDA5, and PKR.

The benefit of targeting TLR3 in cancer and other diseases will most likely ensue from combined activation of different types of cells including the epithelial, myeloid, mesenchymal and endothelial cells. Although immune and non-immune human cells had been shown to produce inflammatory cytokines or not in response to Poly(I:C), this was assumed to depend in human on the cell type rather than on the TLR3 ligand itself.

Compositions comprising dsRNA directed to TLR3 are commercialized. For example there exist commercial Poly (A:U) compositions which are mixtures of dsRNA of different lengths, and the lengths is commonly of the order of 200 to 8000 base pairs.

An objective of the invention is to produce a short dsRNA that is efficient at activating both myeloid and epithelial cells, and lead to cancer cell death. More particularly the objective is to have such short dsRNAs able to both activate myeloid cells and trigger the death of epithelial cancer cells.

Another objective is to propose a dsRNA composition wherein all if not all dsRNA molecules have a predetermined constitution and are active, so that the authority regulation requisites are more easily attained than with undetermined mixtures, and the dsRNA doses may be improved.

Still another objective is to propose dsRNA that do not necessarily need a transfection agent to penetrate the targeted cells.

In an effort to develop new clinical TLR3 ligands for therapy, the inventors screened defined dsRNA for their capacity to both activate myeloid cells and trigger the death of epithelial cancer cells and were able to delineate dsRNA able to respond to these objectives and others.

SUMMARY OF INVENTION

The present invention relates to a composition comprising a dsRNA comprising at least one block or homopolymer of poly A and the complementary block of poly U of short and determined length, in particular a dsRNA wherein each strand has of 50 to 200 nucleotides or bases. Preferably, the length of each strand is between about 55 and about 100, 150 or 200 bases, especially between about 60 and about 70, 80, 90 or 100 bases. Advantageously, all the strands or substantially all the strands in the composition have the predetermined length. Preferably, the strands and the dsRNAs are synthetic.

Synthesis is the privileged mode of production of the dsRNA strands of short and determined length. The dsRNA strands of the invention may be synthetic dsRNA strands, say obtained through synthesis. By convention, the strands and the dsRNA so obtained are qualified of synthetic. Different methods of synthesis are described elsewhere in the application. The short and determined length of the strands according to the invention may be controlled by standard methods such as electrophoresis, as exemplified herein on acrylamide gel.

Methods of synthesis may allow advantageously produce the short and defined dsRNA strands of the invention. These methods allows one to produce advantageously dsRNA strands having the exact length wished. These methods allows one to produce advantageously a composition wherein all the strands are of the same length and/or wherein all the dsRNA are made of strands having the same length. However a certain and limited variation of the length of some strands may be acceptable and encompassed in the compositions according to the invention, whether the strands are produced by synthesis or by another method. In particular, such variation is authorized and encompassed as soon as this does not substantially change the function or the efficacy of the composition. In an embodiment, the variant composition still activate myeloid cells and trigger the death of epithelial cancer cells. In another embodiment, the variant composition still activate myeloid cells and trigger the death of epithelial cancer cells at substantially the same level than the composition wherein all the strands are of the same length and/or wherein all the dsRNA are made of strands having the same length. Preferably, the compositions of the invention comprise a significant and efficient proportion, especially a proportion equal to or above 95, 96, 97, 98, 99, or 99.5, or of about 100%, of strands having the determined length. It can be said that the composition comprises dsRNA active principle consisting essentially of such a significant and efficient proportion of strands having the determined length, including those percentages.

In the dsRNA, the poly A and the poly U blocks may be combined to one or more bases among A, U, G, I, C, poly A, poly U, poly G, poly I or poly C, and the complementary nucleotides or blocks. Exemplary structures are for one strand (then there is the complementary one): poly A-poly I, poly A-poly C, poly I-poly A, poly C—Poly A, poly I-poly A-poly I, poly C-poly A-poly C, poly A-poly I-poly A, poly A-poly C—Poly A.

"Homopolymer" means a sequence of at least two identical and contiguous bases.

Poly A/I or A/C and a complementary strand made of blocks of Poly U/C or U/I are thus encompassed. They may also be designated as poly A/I:poly U/C or Poly A/C:Poly U/I. According to a feature, a poly A/I or poly U/C strand have a predetermined length of more than 50 to about 200 bases. Preferably, the length of said strand is between about 55 and about 200 bases, especially between about 60 and about 100 bases.

The strands may comprise in particular one or more blocks (preferably one or two) of A or U comprising least about 10, 15, 20, 25, 30, 35, 40, 45, 50, 60, 70, 80, 90, A, respectively U; such block may optionally contain less than 20, 15, 14, 13, 12, 11, 10, 9, 8, 7, 6, 5, 4, 3, 2, 1% of another base among A (when Q=A)/U (when Q=A), G, I and C.

The invention makes use in particular of dsRNA of a length comprised between 50 bp and about 200 bp (best about 55 to about 100, 150 or 200, preferably about 60 to about 120, preferably between about 70 and about 100, e.g. about 60, about 70, about 80, about 90) having at least one strand comprising at least one block of A or U, and the complementary strand (thus with the complementary block of U, respectively A), according to the following formula (I) (only one strand is represented), wherein the dsRNA comprises at least 20%, preferably at least 25%, more preferably at least 50%, still more preferably at least 70 or 75%, (or even at least 80, 85, 90 or 95%) of A and U:

$$[P]_a[Q]_b[R]_c \quad (I)$$

- Q represents an homopolymer of A or U, b is an integer of at least 15, 20, 25, 30, 35, 40, 45, 50, 60, 70, 80, 90, or more; such block may optionally contain less than 20, 15, 14, 13, 12, 11, 10, 9, 8, 7, 6, 5, 4, 3, 2, 1% of another base among A (when Q=A)/U (when Q=A), G, I and C;
- a, b and c represent a number of bases or nucleotides, so a+b+c represents the length of the strand or the dsRNA;
- a and c may be independently 0 or an integer such that a+b+c=50 to 200, preferably between 60 and 120, more preferably between 70 and 100; a, b and c may be equal or different;
- if a=1, in case Q=A, P is made of one base among U, G, I and C; as a result of complementarity, in case Q=U, P is made of one base among A, G, I and C;
- if a>1, P is made of at least one or two bases among A, U, G, I and C, under one of these configurations: random combination of at least two of these bases, one block of a base among A, U, G, I and C, at least two blocks of different bases among A, U, G, I and C, or a mixture of at least one block of base among A, U, G, I and C and at least one other base among A, U, G, I and C;
- if c=1, in case R=A, R is made of one base among U, G, I and C; as a result of complementarity, in case R=U, P is made of one base among A, G, I and C;
- if c>1, R is made of at least one or two bases among A, U, G, I and C, under one of these configurations: random combination of at least two of these bases, one block of a base among A, U, G, I and C, at least two blocks of different bases among A, U, G, I and C, or a mixture of at least one block of base among A, U, G, I and C and at least one other base among A, U, G, I and C;
- P and R may be identical or different in terms of bases and/or length of sequence.

In a variant, in formula (I), b is an integer of at least 10.

In Formula (I), wherein Q=A or U, b may be in particular about 35 to about 200, in particular about 50 to about 200, best about 55 to about 100, 150 or 200, preferably about 60 to about 120, preferably between about 70 and about 100, e.g. about 60, about 70, about 80, about 90. The block of poly A may contain less than 20, 15, 14, 13, 12, 11, 10, 9, 8, 7, 6, 5, 4, 3, 2, 1% of another base among U, G, I and C. The block of poly U will be complementary to it and comprise the corresponding A, G, I and/or C.

In an embodiment of this formula (I) above and its embodiments below, the block of polyA or the blocks of polyA may contain less than 20, 15, 14, 13, 12, 11, 10, 9, 8, 7, 6, 5, 4, 3, 2, 1% of another base among U, G, I and C. Thus the corresponding block of polyU or the blocks of poly U would be complementary and have the pairing bases among A, G, I and.

In an embodiment, the formula (I) forms a polyA:polyU. In that case it suffices to have for example a=c=0, Q=A and b of at least 50, or at least about 50, in particular about 50 to about 200, best about 55 to about 100, 150 or 200, preferably about 60 to about 120, preferably between about 70 and about 100, e.g. about 60, about 70, about 80, about 90.

The invention also encompasses the use of modified nucleotide of A, U, I, G, C, such as the O-methylated nucleotides, the phosphorothioate nucleotides, etc.

In another embodiment, the formula (I) forms a polyP-polyA-polyR. The complementary strand would be polyP'-polyU-polyR', with P' and R' being the complementary base or bases of P, respectively R, at the position.

In another embodiment, the formula (I) forms a polyA-polyX-polyA, wherein X may represent U, G, I, C, poly U, poly G, poly I, poly C or any combination thereof and possibly with A or poly A insertions. The complementary strand would be polyU-polyY-polyU, Y being complementary base or bases of X at the position.

In another embodiment, the formula (I) forms a polyP-polyA. The complementary strand would be polyP'-polyU, P' being complementary base or bases of P at the position.

In another embodiment, the formula (I) forms a polyA-polyR. The complementary strand would be polyU-polyR', R' being complementary base or bases of R at the position.

In the following embodiment formulas, a, b and c may have the same meaning as above. A and U designate the bases A and U.

In a first embodiment, the dsRNA is of formula (II):

$$[A]_b$$

$$[U]_b$$

In particular, b=50 to 200, best about 55 to about 100, 150 or 200, preferably about 60 to about 120, preferably between about 70 and about 100, e.g. about 60, about 70, about 80, about 90.

In a second embodiment, the dsRNA is of formula (III):

$$[P]_a[A]_b[R]_c$$

$$[Y]_a[U]_b[Z]_c$$

P and R are independently chosen among G, I and/or C, and Y and Z are the complementary bases.

According to a modality, in formula (III), P and R are both I, and Y and Z are both C.

In particular, in this embodiment and in this modality:

b=is an integer between 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, a and c independently=about 10 to about 50, preferably about 15 to about 40.

In particular, b=is an integer between 10, 15, 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, a and c independently=about 5 to about 50, in particular about 10 to about 50, preferably about 15 to about 40.

In particular, b=is an integer between 10 and 100, a and c independently=about 10 to about 50, preferably about 15 to about 40.

In particular, b=is an integer between 10, 15, 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, a and c independently=about 10 to about 50.

In a third embodiment, the dsRNA is of formula (IV):

$$[A]_b[R]_c$$

$$[U]_b[Z]_c$$

R is chosen among G, I and/or C, Z is the complementary base.

In particular, b=is an integer between 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, c=about 10 to about 50, preferably about 15 to about 40, preferably about 30 to about 40, e.g. about 35, about 40, about 45.

In particular, b=is an integer between 10, 15, 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, c=about 10 to about 50, preferably about 15 to about 40, preferably about 30 to about 40, e.g. about 35, about 40, about 45.

In particular, b=is an integer between 10 and 100, or between about 35 and about 100, c=about 30 to about 50, preferably about 30 to about 40, e.g. about 35, about 40, about 45.

In particular, b=is an integer between 10, 15, 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, c=about 10 to about 50.

In a fourth embodiment, the dsRNA is of formula (V):

$$[P]_a[A]_b$$

$$[Y]_a[U]_b$$

P is chosen among G, I and/or C, Y is the complementary base.

In particular, b=is an integer between 20, 25 or 30 and 100, in particular about 35 to about 100, in particular about 40 to about 100, best about 50 to about 100, e.g. about 50 to about 90, preferably about 50 to about 80, e.g. about 40, about 50, about 60, about 70, about 80, a=about 10 to about 50, preferably about 15 to about 40, preferably about 30 to about 40, e.g. about 35, about 40, about 45.

In particular, b=is an integer between 10 and 100, in particular about 35 to about 100, in particular about 40 to about 100, best about 50 to about 100, e.g. about 50 to about 90, preferably about 50 to about 80, e.g. about 40, about 50, about 60, about 70, about 80, a=about 10 to about 50, preferably about 15 to about 40, preferably about 30 to about 40, e.g. about 35, about 40, about 45.

In particular, b=is an integer between 10 and 100, in particular about 35 to about 100, a=about 30 to about 50, preferably about 30 to about 40, e.g. about 35, about 40, about 45.

In particular, b=is an integer between 10 and 100, in particular about 35 to about 100, in particular about 40 to about 100, best about 50 to about 100, e.g. about 50 to about 90, preferably about 50 to about 80, e.g. about 40, about 50, about 60, about 70, about 80, a=about 10 to about 50.

In an embodiment, the dsRNA is of formula (VI):

$[P]_a[A]_b[R]_c$ $[Y]_a[U]_b[Z]_c$

P and R are independently chosen among I and C, and Y and Z are the complementary bases, b=is an integer between about 20, 25 or 30 and about 100, one of a or c may be 0, and a and c not being equal to 0 at the same time, are about 10 to about 50.

In an embodiment of these formulae (II), (Ill), (IV), (V), (VI), the block or homopolymer of poly A or the blocks or homopolymers of poly A may contain less than 20, 15, 14, 13, 12, 11, 10, 9, 8, 7, 6, 5, 4, 3, 2, 1% of another base among U, G, I and C. The complementary block(s) of U will of course integrate the complementary bases.

In a preferred embodiment, the composition comprises a poly A/I strand and a poly U/C strand wherein both strands have the same predetermined length of more than 50 to about 200 bases. Preferably, the length of both strands is between about 55 and about 200 bases, especially between about 60 and about 100 bases. For example, both strands have about 60, 70, 80, 90 or 100 bases each.

The term "double-stranded" means a portion where ribonucleotides are hydrogen bonded (base-paired) to complementary ribonucleotides to form a double-stranded structure. One may speak of overlap where both strands are paired. Preferably the entire strands are paired (100% of the complementary strands are paired). However, the invention encompasses dsRNA having at least about 60%, 70%, 80%, 90%, 95%, 97%, 98%, 99% or 99.5% of strand length paired (double-stranded conformation). In a same composition it is possible to have dsRNA of varying % of pairing. The determination of what percentage of the dsRNA TLR3 agonist is in a double-stranded conformation is achieved by dividing the number of nucleotides that are base-paired by the total number of nucleotides in a molecule. Thus, a 21 base-paired molecule containing 2 nucleotide overhangs at both the 3' and 5' end would have 42 nucleotides that are base-paired and 4 nucleotides that are not base-paired, making it 42/46 or 91.3% double-stranded or paired.

The conformity of a batch of dsRNA may be controlled by known means. An example is the method described in Examples 1 and 10 with acrylamide gels.

Preferably the compositions of the invention comprise a set of such dsRNA having more than 95, 96, 97, 98, 99 or 99.5% pairing or of fully (about 100%) paired dsRNA, e.g. the dsRNA comprises a Poly A/I strand and a Poly U/C strand, wherein both strands have the same predetermined length of more than 50 to about 200 bases, preferably, the length of both strands is between about 55 and about 200 bases, especially between about 60 and about 100 bases. For example, both strands have about 60, 70, 80, 90 or 100 bases each.

The composition may further comprise a pharmaceutically acceptable vehicle, carrier or excipient. In an embodiment, the composition is sterile.

In the invention, the term "comprise" may be replaced by "consist essentially of" or "consist of".

Another object of the invention is such a composition as a medicament.

Another object of the invention is such a composition for use in a method of treating a human or animal cancer expressing TLR3 receptor.

Another object of the invention is such a composition for use as a medicament.

Another object is the use of this composition for the manufacture of a medicament for treating a human or animal cancer expressing TLR3 receptor.

The dsRNA contained in the composition serves as an agonist of the TLR3 receptor.

In an embodiment, the composition induces inflammation in human or animal myeloid cells.

In an embodiment, the composition induces for example the production of TNF-alpha and/or type I interferon by the human or animal myeloid cells.

In an embodiment, the composition triggers the death of epithelial cancer cells.

In an embodiment, the composition induces both inflammation and cancer cell death.

Another object of the invention is such a composition as a medicament activating human or animal myeloid cells, in particular with TNF-alpha production and ISRE-reporter gene activation, and triggering the death of epithelial cancer cells.

Another object of the invention is such a composition as a medicament activating specifically TLR3 expressed by myeloid cells (macrophages and dendritic cells), inducing the secretion of inflammatory cytokine, and triggering the TLR3-dependent activation of inflammation and death in human or mammal cancer cells.

Another object is a pharmaceutical composition comprising a dsRNA according to the invention and a chemotherapeutic drug, for use in a method of treating a cancer expressing TLR3, with a simultaneous, separate or sequential administration of the dsRNA according to the invention and a chemotherapeutic drug to a mammal or human. This is the (combined) use of a pharmaceutical composition as disclosed here of a chemotherapeutic drug in a combined therapy against the cancers as disclosed herein.

Another object of the invention is a method for treating a cancer in a patient in need thereof. The method comprises the administration of a sufficient amount of a composition as described herein.

In an embodiment, the method activates myeloid cells.

In an embodiment, the method induces the production of TNF-alpha by the myeloid cells.

In an embodiment, the method triggers the NF-Kb- and ISRE-dependent signaling pathway downstream of TLR3.

In an embodiment, the method triggers the death of epithelial cancer cells.

In an embodiment, the method activates myeloid cells, in particular with TNF-alpha production, and triggers the death of epithelial cancer cells.

In an embodiment, the method activates specifically TLR3 expressed by myeloid cells (macrophages and dendritic cells), inducing the secretion of inflammatory cytokine, and triggers the TLR3-dependent inflammation and death in human or mammalian cancer cells.

DETAILED DESCRIPTION

The inventors have screened a series of synthetic dsRNA with various bases compositions, distribution of nucleotides on the two strands and sequences for their capacity to trigger the production of TNF-alpha by the RAW mouse macrophage cell line. The sequences of the first 47 dsRNA tested are presented in table 1. The analysis of commercial Poly (A:U) and 9 dsRNAs ID #345 and, 397, 398, 415, 418, 405, 411, 412, 413 on native acrylamide gel shows that, on the contrary to commercial Poly(A:U) which is a mixture of dsRNA of different lengths, a single major band is detectable at the expected size for each synthetic 50 bp dsRNA (FIG.

1). When the 47 synthetic dsRNA were tested for their capacity to activate the production of TNF-alpha by mouse macrophage Raw cells, none was effective but the 50 bp Poly(A:U) dsRNA (hereafter named dsRNA ID #412) (FIG. 2) that was as efficient as commercial high molecular weight Poly(A:U). Thus, dsRNA ID #412 was efficiently internalized by macrophages and capable of triggering the NF-Kb signaling pathway downstream of TLR3. Remarkably, when the As and Us of a 50 bp Poly(A:U) were distributed on the two strands, (dsRNA ID #413) no TNF-alpha secretion was observed. Unexpectedly, 50 bp Poly(I:C) (dsRNA ID #411) was unable to trigger TNF-alpha production.

The inventors next evaluated the capacity of dsRNA ID #412 to trigger the death of TLR3 WT and TLR3 KO human non-small cell cancer epithelial cells NCI-H292. In the absence of transfection reagent, dsRNA ID #412 could activate neither inflammatory response (FIG. 3) nor death of NCI-H292 cells (FIG. 4). Therefore, in contrast to macrophages, dsRNA ID #412 either was not internalized or could activate neither the NF-kB TLR3 signaling pathway nor the death in epithelial cancer cells.

Figure 5:
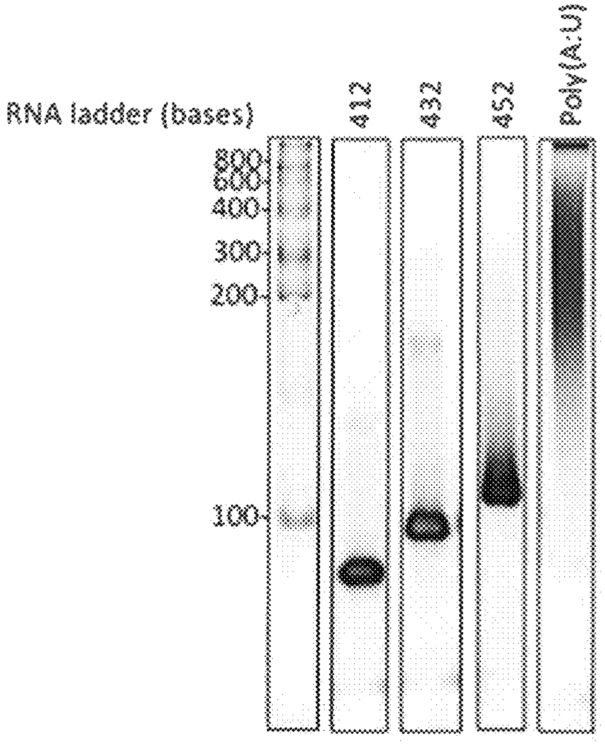

Poly(A:U) of 70 bp (dsRNA ID #432) and of 90 bp (dsRNA ID #452), as defined in Table 2, were then used. Again, both of those synthetic sequences showed a single major band when analyzed on native polyacrylamide gel (FIG. 5). DsRNA ID #432 and 452 were as efficient as dsRNA ID #412 to trigger the inflammatory response of Raw cells as illustrated by the production of TNF-alpha (FIG. 6) and the activation of ISRE-luciferase reporter gene (FIG. 7). Moreover, dsRNA ID #432 and 452 unexpectedly triggered the TLR3-dependent inflammatory (FIG. 8) and apoptotic responses (FIG. 9) of human cancer cells NCI-H292 without transfection reagent.

Figure 10:
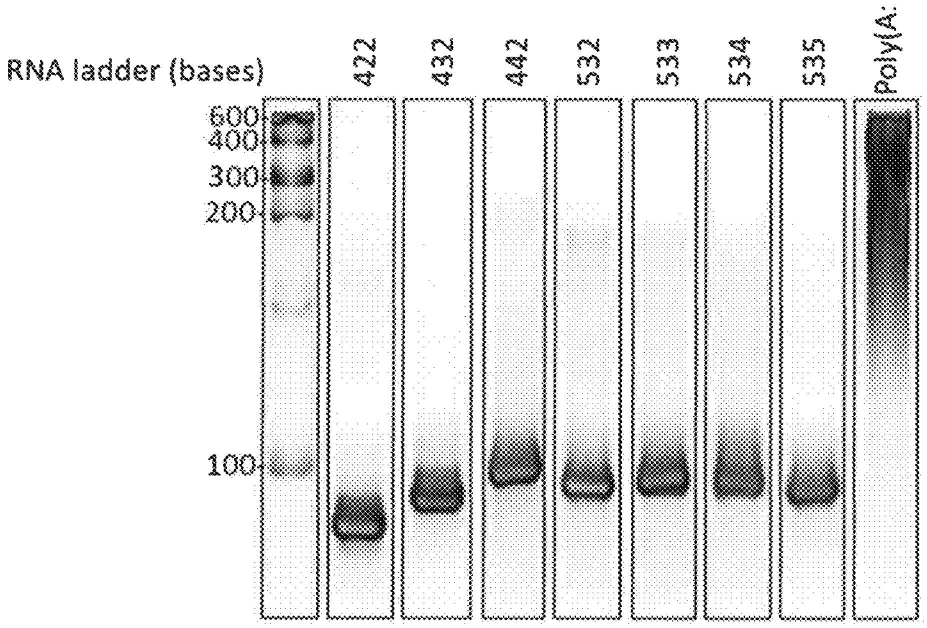

The inventors further tested Poly(A:U) of 60 bp (dsRNA ID #422) and 80 bp (dsRNA ID #442), 3 chimeric 70 bp PolyA/I:U/C dsRNAs: dsRNA ID #532, (dsRNA ID #533, dsRNA ID #534, and dsRNA ID #535) (as defined in table 2). Again, native acrylamide gel shows a single major band at the expected size for each synthetic dsRNA (FIG. 10).

Figure 11:
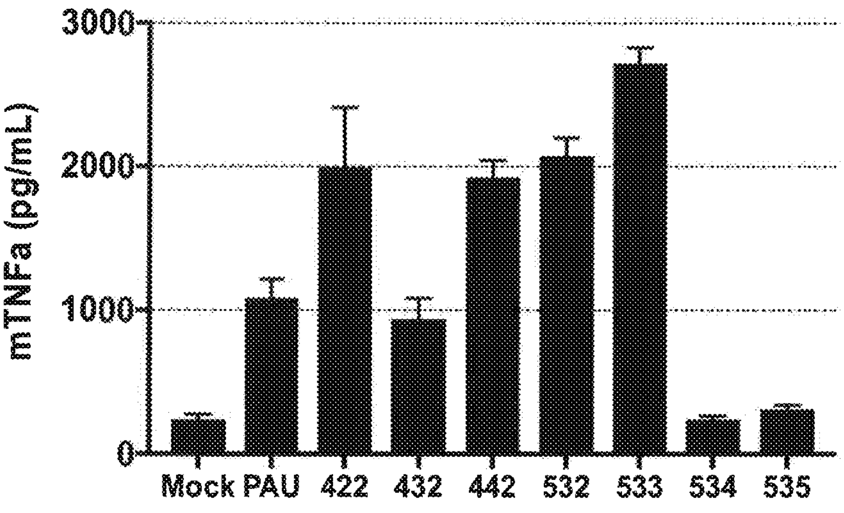
Figure 12:
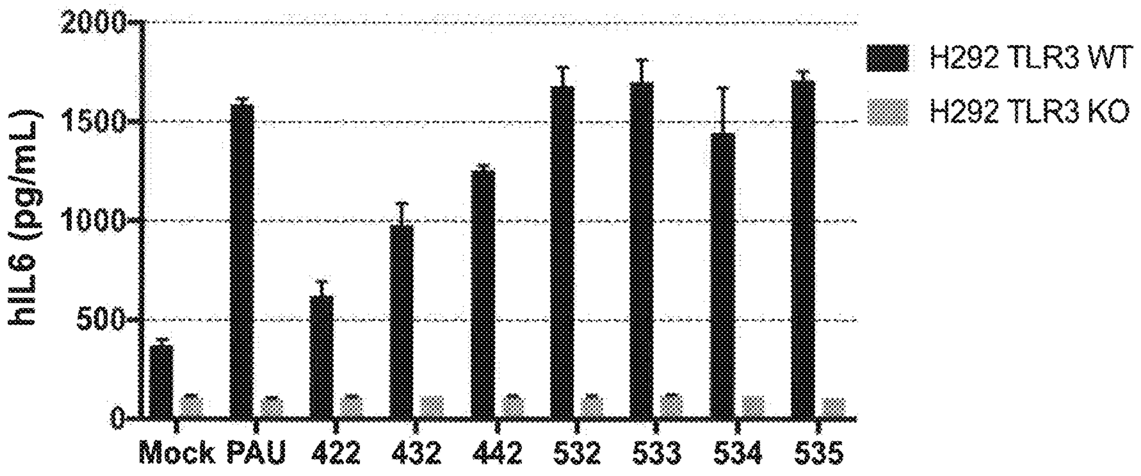
Figure 13:
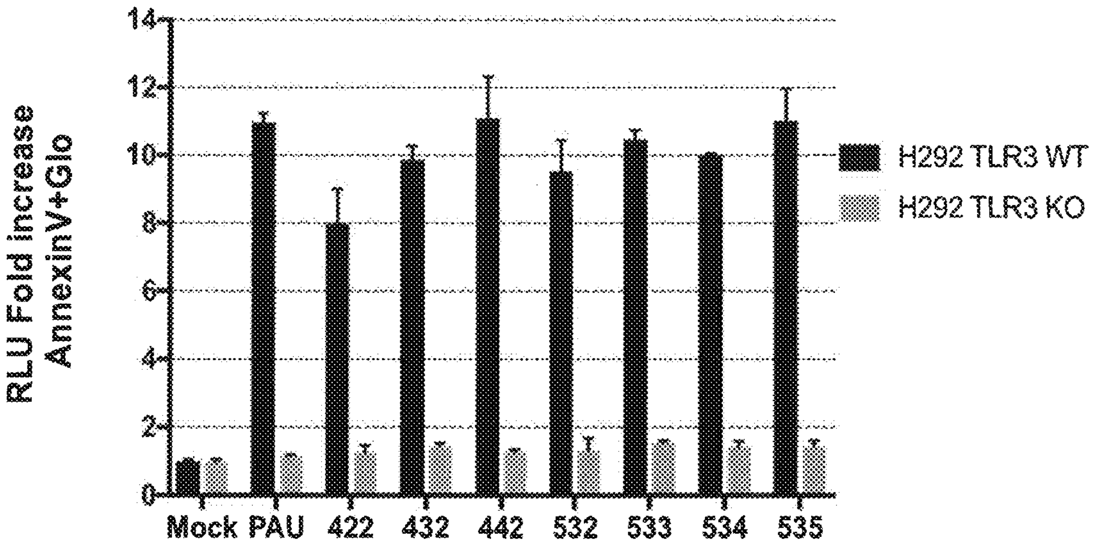

It was observed that: (1) the 70 bp chimeric dsRNA ID #532 and dsRNA ID #533 were the most powerful to induce the secretion of mTNFa by Raw cells (FIG. 11) and (2) that they were both very effective to trigger the secretion of IL-6 by NCI-H292 cells (FIG. 12); (3) moreover, they were as effective as 70 bp Poly(A:U) (dsRNA ID #432) to kill NCI-H292 cells (FIG. 13). Noticeably, neither the 70 bp Poly(I:C) (dsRNA ID #535) nor the I:C-rich chimeric 70 bp dsRNA (dsRNA ID #534) did activate significantly the secretion of TNF-alpha by Raw cells (FIG. 11).

Thus, well-defined synthetic Poly(A:U) according to the invention, e.g. of 70 bp and 80 bp, and 70 bp A:U-rich chimeric dsRNA such as dsRNA ID #532 and dsRNA ID #533 have the unique capacity to both activate myeloid cells to induce the secretion of inflammatory cytokines and trigger the TLR3-dependent activation of inflammation and death in cancer cells.

dsRNAs ID #s 422, 432, 442, 452, 532 and 533 are preferred examples of dsRNAs according to the invention. Other examples are (with the complementary strand C or I, respectively U or A):

5' (I)10-(U)50-(I)10 3' (SEQ ID NO: 95)
5' (A)60-(I)10 3' (SEQ ID NO: 119)
5' (A)50-(I)20 3' (SEQ ID NO: 120)
5' (A)20-(I)50 3' (SEQ ID NO: 121)
5' (I)5-(A)60-(I)5 3' (SEQ ID NO: 96)
5' (I)15-(A)40-(I)15 3' (SEQ ID NO: 97)
5' (I)20-(A)30-(I)20 3' (SEQ ID NO: 98)
5' (I)25-(A)20-(I)25 3' (SEQ ID NO: 99)
5' (I)5-(A)50-(I)15 3' (SEQ ID NO: 100)
5' (I)13-(A)64-(I)13 3' (SEQ ID NO: 101)
5' (I)10-(A)70-(I)10 3' (SEQ ID NO: 102)

Still other examples are (with the complementary strand C or 1, respectively U or A:

5' (A)10-(I)60 3' (SEQ ID NO: 122)
5' (I)30-(A)10-(I)30 3' (SEQ ID NO: 123)

The invention thus concerns compositions comprising one of these specific dsRNAs as the unique polulation of dsRNAs contained in said composition, or in a significant and efficient proportion, especially a proportion equal to or above 95, 96, 97, 98, 99, or 99.5 of the total dsRNAs comprised in the composition.

Definitions

"TLR3", "TLR3 protein" and "TLR3 receptor", used interchangeably, are used herein to refer to Toll Like Receptor 3, a member of the Toll-like receptor (TLRs) family. Its amino acid sequence of is shown in NCBI gene ID 7098. Toll Like Receptor 3 is a member of the Toll-like receptor (TLR) family which plays a fundamental role in pathogen recognition and activation of innate immunity. This receptor is most abundantly expressed in placenta and pancreas, and is restricted to the dendritic subpopulation of the leukocytes. It recognizes dsRNA associated with viral infection, and induces the activation of NF-κB and the production of type I interferons.

By "cancer" is meant the survival, division or proliferation of abnormal cells in the body. In particular, cancers covered are those that express TLR3. The determination of TLR3 expression in cancer cells is well within the ability of the man skilled in the art and can be measured by any method available to the man skilled in the art such as immunohistochemistry, Western Blot, or quantitative PCR (for example by using the LightCycler® System of Roche Molecular Diagnostics), etc. Still particularly, cancers covered by the present invention are chosen from: epithelial cancers such as Small-cell Lung cancers, Non-Small-Cell Lung cancer, lung adenocarcinomas, hepatocarcinoma, neuroblastoma, Head and Neck, ovarian, renal, bladder, prostate, breast, cervix, pancreas, esophageal, gastric, small intestine, colon, or melanoma cancers and mesenchymal cancers such as mesothelioma or sarcoma cancer, and more particularly Non-Small-Cell Lung cancer.

As used herein, the term "subject" or "patient" refers to a warm-blooded animal such as a mammal, animal or human, in particular a human, who is afflicted with, or has the potential to be afflicted with one or more diseases and conditions described herein.

The terms "treat", "treating", "treated" or "treatment", as used herein, refer to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition, to the prevention of the onset, recurrence or spread of a disease or disorder, or of one or more symptoms thereof. In certain embodiments, the terms refer to the treatment with or administration of a compound provided herein prior to the onset of symptoms. The terms encompass the inhibition or reduction of a symptom of the particular disease. Subjects with familial history of a disease in particular are candidates for treatment regimens in certain embodiments. Also, subjects in whom a genetic disposition for the particular disease has been shown are candidates for treatment regimens in certain embodiments. In addition, subjects who have a history of recurring symptoms are also potential candidates for the treatment. In this regard, the term "treatment" may be interchangeably used with the term "prophylactic treatment."

The identification of the subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

As used herein, a "pharmaceutically acceptable excipient" refers to molecular entities and compositions that do not produce an adverse, allergic or other untoward reaction when administered to a mammal, especially a human, as appropriate. A pharmaceutically acceptable excipient refers to a non-toxic solid, semi-solid or liquid filler, diluent, encapsulating material or formulation auxiliary of any type.

For the purposes of the present disclosure, administering at the same time (e.g., simultaneously) refers to administering the drugs together in same formulation or in separate formulations wherein the administration may be a few minutes to a few hours apart, but no more than one day. As used herein administering at different times (e.g., sequentially) refers to administering the drugs of the combination therapy a few hours to days, weeks and even months apart. Therefore, in certain embodiments a subject undergoing combination therapy can receive both drugs at the same time (e.g., simultaneously) or at different times (e.g., sequentially, in either order, on the same day, or on different days), so long as the therapeutic effect of the combination of both drugs is caused in the subject undergoing therapy. In some embodiments, the combination of drugs will be given simultaneously for one dosing, but other dosing will include sequential administration, in either order, on the same day, or on different days. Where the two drugs are administered simultaneously, they can be administered as separate pharmaceutical compositions, each comprising either drug of the combination, or can be administered as a single pharmaceutical composition comprising both of these drugs.

TLR3 Agonist Formulations and Delivery Systems

By TLR3 agonist is meant in this document a dsRNA according to the invention, unless contrary indication.

Preferably, the TLR3 agonist is formulated into a pharmaceutically acceptable composition. The pharmaceutically acceptable compositions described herein additionally comprise pharmaceutically acceptable carriers, adjuvants and/or vehicles. Pharmaceutically acceptable carriers, adjuvants and vehicles that may be used include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers including nanoparticles, or both, and then if necessary shaping the product.

In certain embodiments, the composition is administered to the tumour. It can be applied on the surface, e.g. using an appropriate formulation such as a gel or a patch for prolonged contact with the tumor site, or in the tumour mass, e.g. using an implant, or injected into the tumour, e.g. using injectable compositions as described herein.

In certain preferred embodiments, the compound is administered orally. Compositions suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172 and 4,842,866. Coatings can be used for delivery of compounds to the intestine (see, e.g., U.S. Pat. Nos. 6,638,534, 5,217,720, and 6,569,457, 6,461,631, 6,528,080, 6,800,663).

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and/or suspending agents. If desired, certain sweetening and/or flavoring and/or coloring agents may be added. Surfactants such as sodium lauryl sulfate may be useful to enhance dissolution and absorption.

In certain embodiments, the composition is linked either covalently or not with another molecule such as an antibody, another protein or peptide, a lipid or a sugar, or another receptor ligand.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

In certain embodiments, the composition is linked either covalently or not with nanoparticles Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets. Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions may be administered in the form of suppositories for rectal or vaginal administration. These compositions can be prepared by mixing a compound with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions is especially useful when the desired treatment involves areas (including mucosa and mesothelial surfaces) or organs readily accessible by topical application. For application topically to the skin, the pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. Alternatively, the pharmaceutical composition can be formulated with a suitable gel. The pharmaceutical compositions of this invention may also be topically applied to the lower intestinal tract by rectal suppository formulation or in a suitable enema formulation. Topically-transdermal patches and iontophoretic administration are also described.

The pharmaceutical compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Aerosol formulations that may be utilized in the methods of this invention also include those described in U.S. Pat. No. 6,811,767.

Liposomes which are pH-sensitive or negatively-charged, entrap dsRNA rather than complex with it. Since both the dsRNA and the lipid are similarly charged, repulsion rather than complex formation occurs. The dsRNA is thus entrapped in the aqueous interior of these liposomes. One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol. Liposomes that include nucleic acids have been described, for example, in WO 96/40062, U.S. Pat. Nos. 5,264,221, 5,665,710.

Also described herein is an implantable drug release device impregnated with or containing a TLR3 agonist or a composition comprising a TLR3 agonist, such that said TLR3 agonist is released from said device and is therapeutically active.

TLR3 Agonist Combination Compositions

Treatment with a TLR3 agonist as described herein can optionally advantageously be combined with one or more other therapeutic agents useful in the treatment of cancer. Thus, the TLR3 agonists described herein can be used conjointly, or in combination with, another therapeutic agent useful in the treatment of cancer. The TLR3 agonist compositions described above may thus additionally include other therapeutic agents useful in the treatment of cancer. The other therapeutic agent may be in the same or preferably in a separate container. Such agents include other dsRNA-TLR3 agonists of different nucleotide sequence; cytotoxins, including but not limited to those recited above for use in cytotoxic and tumoricidal TLR3 ligand complexes; cytotoxic and tumoricidal TLR3 ligand complexes; agents that target a tumor antigen or a tumor proliferative protein; chemotherapy agents including, but not limited to, cisplatin (CDDP), carboplatin, oxaliplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tarnoxifen, raloxifene, estrogen receptor binding agents, taxol, gemcitablen, navelbine, famesyl-protein tansferase inhibitors, transplatinum, 5-fluorouracil, vincristin, vinblastin and methotrexate, or any analog or derivative variant of the foregoing; therapeutic agents and combination of therapeutic agents for treatment of specific cancers, such as for breast cancer: doxorubicin, epirubicin, the combination of doxorubicin and cyclophosphamide (AC), the combination of cyclophosphamide, doxorubicin and 5-fluorouracil (espace ajouté) (CAF), the combination of cyclophosphamide, epirubicin and 5-fluorouracil (CEF), Herceptin™), tamoxifen, the combination of tamoxifen and a cytotoxin, taxanes including docetaxel and Paclitaxel, the combination of a taxane plus doxorubicin and cyclophophamide; for colon cancer: the combination of 5-FU and leucovorin, the combination of 5FU and levamisole, irinotecan (CPT-11) or the combination of irinotecan, 5-FU and leucovorin (IFL) or oxaliplatin; for prostate cancer: a radioisotope (i.e., palladium, strontium-89 and Iridium), leuprolide or other LHR agonists, nonsteroidal antiandrogens (flutamide, nilutamide, and bicalutamide), steroidal antiandrogens (cyproterone acetate), the combination of leuprolide and flutainide, estrogens such as DES, chlorotrianisene, ethinyl estradiol, conjugated estrogens U.S.P., DES-diphosphate, second-line hormonal therapies such as aminoglutethimide, hydrocortisone, flutamide withdrawal, progesterone, and ketoconazole, low-dose prednisone, or other chemotherapy agents or combination of agent reported to produce subjective improvement in symptoms and reduction in PSA level including docetaxcl, paclitaxel, estramustine/docetaxel, estramustine/etoposide, estramustine/vinblastine, and estramustine/Paclitaxel; for melanoma: dacarbazine (DTIC), nitrosoureas such as carmustine (BCNU) and lomustine (CCNU), agents with modest single agent activity including vinca alkaloids, platinum compounds, and taxanes, the Dartmouth regimen (cisplatin, BCNU, and DTIC), interferon alpha (IFN-A), and interleukin-2 (IL-2); for ovarian cancer: Paclitaxel, docetaxel, cisplatin, oxaliplatin, hexamethylmelamine, tamoxifen, ifosfamide, the combination of paclitaxel (Taxol) or docetaxel (Taxotere) and cisplatin or carboplatin, the combination of cyclophosphamide and cisplatin, the combination of cyclophosphamide and carboplatin, the combination of 5-fluorouracil (5FU) and leucovorin, etoposide, liposomal doxorubicin, gerucitabine or topotecan; for lung cancer: cisplatin, vincristine, vinblastine, mitomycin, doxorubicin, and etoposide, alone or in combination, the combination of cyclophosphamide, doxorubicin, vincristine/etoposide, and cisplatin (CAV/EP), the combination of cisplatin and vinorelbine, paclitaxel, docetaxel or gemcitabine, and the combination of carboplatin and paclitaxel.

In one aspect, the other therapeutic agent is an immune checkpoint inhibitor. It may be a biologic therapeutic or a small molecule. Preferably, the checkpoint inhibitor is a monoclonal antibody, a humanized antibody, a fully human antibody, a fusion protein or a combination thereof. The antibody may be directed against any protein that is involved in the pathway, and more particularly against either the receptor or the ligand. As it is known, an immune check point inhibitor is able to restore the immune response to the cancer cells. In particular, the inhibitor disrupts or impedes, or inhibits, the interaction between interacting proteins, and to allow for immune response, in particular T cells killing the tumor cells. In a further aspect, the checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 or a combination thereof. In an additional aspect, the checkpoint inhibitor interacts with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 or a combination thereof.

The invention comprises the combined use of an antibody that blocks, inhibits or reduces the PD1/PD-L1 and/or PD1/PD-L2 pathway. There are currently at least five agents blocking the pathway that are marketed or in clinical evaluation, any of these may be useful in combination with the invention. These agents are BMS-936558 (anti-PD-L1 mAb, Nivolumab/ONO-4538, Bristol-Myers Squibb, formerly MDX-1106 (antibody 5C4 in WO 2006/121168), MK-3475 (anti-PD1 mAb, lambrolizumab or pembrolizumab, Keytruda®, Merck), MPDL3280A/RG7446 (anti-PD-L1 mAb, Atezolizumab, Roche/Genentech), AMP-224 (immunoadhesin comprising an anti-PD-L2, Amplimmune and GSK), Pidlizumab (anti-PD1 mAb, CT-011, CureTech/TEVA—WO 2009/101611).

For MK-3475 DNA constructs encoding the variable regions of the heavy and light chains of the humanized antibodies h409All have been deposited with the American Type Culture Collection Patent Depository (10801 University Bld., Manassas, Va.). The plasmid containing the DNA encoding the heavy chain of h409A-I 1 was deposited on Jun. 9, 2008, and identified as 081469_SPD-H and the plasmid containing the DNA encoding the light chain of h409AI 1 was deposited on Jun. 9, 2008 and identified as 0801470_SPD-L-I 1.

Further known PD-1 antibodies and other PD-1 inhibitors include AMP-224 (a B7-DC/IgG1 fusion protein licensed to GSK), AMP-514 described in WO 2012/145493, antibody MEDI-4736 (an anti-PD-L-1 developed by AstraZeneca/Medimmune) described in WO2011/066389 and US2013/034559, antibody YW243.55.570 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/014708, WO2009/114335 and WO2013/019906. The disclosures of any document referred to herein are hereby incorporated by reference. Further examples of anti-PD1 antibodies are disclosed in WO2015/085847 for examples antibodies having light chain variable domain CDR1, 2 and 3 of SEQ ID NO:6, SEQ ID NO: 7 and SEQ ID NO: 8, respectively, and antibody heavy chain variable domain CDR1, 2 and 3 of SEQ ID NO: 3, SEQ ID NO: 4 and SEQ ID NO: 5, respectively, wherein the SEQ ID NO references are the numbering according to WO2015/085847.

The invention also comprises the combined use of an antibody against CTLA-4 (cytotoxic T-lymphocyte-associated protein 4), also known as CD152 is another inhibitor member of the CD28 family of receptors, and is expressed on T cells. Antibodies that bind and inhibit CTLA-4 are known in the art. In one example, the antibody is ipilimumab (trade name Yervoy®, Bristol-Myers Squibb), a human IgG antibody.

In another combination, TLR3 ligand is an agonist of stimulatory checkpoint pathways such as OX40, ICOS, GITR, 4-1BB or CD40.

In another combination, the agent associated with TLR3 ligand is molecule targeting tumor microenvironment such as an inhibitor of transforming growth factor-beta signaling pathway (i.e. galunisertib).

The methods of using a TLR3 agonist composition described herein may also comprises combination treatment with an anti-angiogenic agent. The TLR3 agonist compositions described above may thus also include an anti-angiogenic agent. New blood vessel formation (angiogenesis) is a fundamental event in the process of tumor growth and metastatic dissemination. The vascular endothelial growth factor (VEGF) pathway is well established as one of the key regulators of this process. The VEGF/VEGF-receptor axis is composed of multiple ligands and receptors with overlapping and distinct ligand-receptor binding specificities, cell-type expression, and function. Activation of the VEGF-receptor pathway triggers a network of signaling processes that promote endothelial cell growth, migration, and survival from pre-existing vasculature. In addition, VEGF mediates vessel permeability, and has been associated with malignant effusions. The VEGF-related gene family comprises six secreted glycoproteins referred to as VEGF-A, VEGF-B, VEGF-C, VEGF-D, VEGF-E, and placenta growth factor (PIGF)-1 and -2. A number of exemplary anti-angiogenic agents acting of the VEGR pathway are known, any of which can be used in accordance with the invention, including small molecule inhibitor, neutralizing antibodies antisense strategies, RNA aptamers and ribozymes against VEGF-related gene family (e.g. the VEGF-A, VEGF-B, VEGF-C, VEGF-D, VEGF-E proteins). Variants of VEGF with antagonistic properties may also be employed, as described in WO 98/16551. Further exemplary anti-angiogenic agents that are useful in connection with combined therapy are listed in Table D of U.S. Pat. No. 6,524,583. Particularly preferred anti-angiogenic agents inhibit signaling by a receptor tyrosine kinase including but not limited to VEGFR1, VEGFR-2,3 PDGFR-beta, Flt-3, c-Kit, p38 alpha and FGFR-1. Further anti-angiogenic agent may include agents that inhibit one or more of the various regulators of VEGF expression and production, such as EGFR, HER-2, COX-2, or HIF-1. Another preferred class of agents includes thalidomide or the analogue CC-5013.

In one aspect, the other therapeutic agent is an immune modulator including indolamine oxydase inhibitor, selected VEGF/VEGFR inhibitors of the monoclonal antibody (mAb) and tyrosine kinase inhibitor (TKI) class that include bevacuzimab (Avastin) (mAb, inhibiting VEGF-A, Genentech); IMC-1121B (mAb, inhibiting VEGFR-2, ImClone Systems); CDP-791 (Pegylated DiFab, VEGFR-2, Celltech); 2C3 (mAb, VEGF-A, Peregrine Pharmaceuticals); PTK-787 (TKI, VEGFR-1, -2, Novartis); AEE788 (TKI, VEGFR-2 and EGFR, Novartis); ZD6474 (TKI, VEGFR-1, -2, -3, EGFR AstraZeneca); AZD2171 (TKI, VEGFR-1, -2, AstraZeneca); SU11248 (TKI, VEGFR-1,-2, PDGFR Pfizer); AG13925 (TKI, VEGFR-1, -2, Pfizer); AG013736 (TKI, VEGFR-1, -2, Pfizer); CEP-7055 (TKI, VEGFR-1, -2, -3, Cephalon); CP-547,632 (TKI, VEGFR-1, -2, Pfizer); VEGF-trap (Soluble hybrid receptor VEGF-A, P1GF (placenta growth factor) Aventis/Regeneron); GW786024 (TKI, VEGFR-1, -2, -3, GlaxoSmithKline); Bay 93-4006 (TKI, VEGFR-1, -2, PDGFR Bayer/Onyx); and AMG706 (TKI, VEGFR-1, -2, -3, Amgen). Most preferred are tyrosine kinase inhibitors that inhibit one or more receptor tyrosine kinases selected from the group consisting of VEGFR1, VEGFR-2,3 PDGFR-beta, Flt-3, c-Kit, p38 alpha and FGFR-1. Preferred examples include SU11248 (Pfizer) and Bay 93-4006 (sorefanib, Bayer).

The methods of using a TLR3 agonist composition described herein may also comprise combination treatment with a pro-apoptotic agent. The TLR3 agonist compositions described above may thus also include a pro-apoptotic agent. A number of proteins useful as targets for modulation by pharmaceutical agents are known in the art, including any of those reviewed in Green and Kroemer, J. (2005) Clin. Investig. 115(10):2610-2617. Examples of pro-apoptotic pharmaceutical agents include: drugs that induce mitochondrial outer membrane permeabilization such as oblimirsen (Bcl-2 antisense oligonucleotide, Genta), EGCG (small molecule targeting Bcl-2, Burnham Inst./Mayo Clinic), Gossypol (small molecule targeting Bcl-2, Univ. Michigan), LY2181308 (antisense oligonucleotide targeting survivine (Eli Lilly/Isis), and arsenic trioxide; drugs that regulate p53 activity such as Advexin INGN201 (adenovirus modulating p53, Introgen), SCH58500 (adenovirus modulating p53, Schering-Plough), ONYX-015 (E1B mutated adenovirus modulating p53, Onyx Pharma.); drugs that modulate caspases and/or endogenous inhibitors or caspases such as AEG35156 (antisense oligonucleotide targeting XIAP, Aegara/Hybridon); drugs that modulate cIAP1-2 such as birinapant; drugs that modulate death receptors and/or their ligands, such as TNF-alpha polypeptides, HGS-ETR1 (agonistic mAb targeting TRAIL-R1, Human Genome Sciences), HGS-ETR2 and HGS-TR2J ((two agonistic mAbs targeting TRAIL-R2, Human Genome Sciences); PRO1764 (soluble TRAIN ligands, Genentech/Amgen); and drugs targeting poly(ADP-ribose) polymerase (PARP), such as AG014699 (small molecule, Cancer Res. Tech.); drugs targeting the proteosome, such as bortezomib (Velcade) (26S proteosome inhibitor, Millennium Pharma.); and kinase inhibitors, such as herceptin (mAb targeting HER2, Roche), centuximab (mAb targeting HER1, Imclone/BMS), gefitinib (Iressa) and erlotinib (Tarceva) (small molecule inhibitors of HER1, AstraZeneca and Genentech/OSI respectively, CCI-779 (small molecule acting on mTOR, Novartis, Bay 43-9006 (small molecule inhibitor of kinases including Raf and VEGFR, and imatinib mesylate (Gleevec, STI-571) (small molecule inhibitor of cKit, PDGFR, Bcr-Abl, Novartis).

The TLR3 agonist compositions described above may also include other therapeutic agents such as immunomodulatory agents such as tumor necrosis factor, interferon alpha, beta, and gamma, IL-2, IL-12, IL-15, IL-21, CpG-containing single-stranded DNA, agonists of other TLRs including for example BCG, other cytokines and immunostimulating agents; F42K and other cytokine analogs; or MIP-1, MIP-1 beta, MCP-1, RANTES, and other chemokines; agents that affect the upregulation of cell surface receptors and GAP junctions; cytostatic and differentiation agents; or inhibitors of cell adhesion.

Also described is a composition of matter comprising a TLR3 agonist and another therapeutic agent useful in the treatment of cancer in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The agent and the TLR3 agonist are preferably packaged together in a blister pack or other multi-chamber package, or as connected, separately sealed containers (such as foil pouches or the like) that can be separated by the user (e.g., by tearing on score lines between the two containers).

The TLR3 agonist compositions described above may also include other therapeutic modalities including the use of Ionizing radiation, the injection of CAR-T cells and/or the use of oncolytic viruses.

Cancer and Therapeutic Methods and Uses for.

The present specification encompasses a TLR3 agonist for use in the prevention, management, treatment or amelioration of cancer or one or more symptoms thereof. The invention also encompasses the use of a TLR3 agonist for the manufacture of a medicament for the prevention, management, treatment or amelioration of cancer or one or more symptoms thereof. It also encompasses methods for preventing, managing, treating or ameliorating cancer or one or more symptoms thereof. More precisely, and in accordance with the Summary of Invention, by use of a TLR3 agonist according to the invention in a method of use or in a use for treating, it is intended a TLR3 agonist per se as or a composition as disclosed herein, based on such TLR3 agonist.

Examples of cancers that can be prevented, managed, treated or ameliorated in accordance with the methods invention include, but are not limited to, solid tumors, and particularly cancers such as cancer of the head, neck, eye, mouth, throat, esophagus, chest, bone, lung, colon, rectum, stomach, prostate, breast, ovaries, kidney, liver, pancreas, and brain.

A particular object of the invention is a method of treatment of bladder cancer or a use for treating bladder cancer. In the method of treatment, the bladder cancer may be treated by a composition as disclosed herein administered in sufficient amount to a patient in need thereof. A composition as disclosed herein may be for use in treating bladder cancer in a patient.

In an embodiment, bladder cancer is a bladder cancer with resistance to standard immunotherapy. Standard immunotherapy comprises therapy with BCG and/or with an Inhibitor of Immune Check Point (ICI), such as an anti-PD1 or an anti-PD-L1 (especially with an anti-PD1 or an anti-PD-L1 monoclonal antibody and the like). In this embodiment, a composition as disclosed herein is used for treating said bladder cancer or administered to a patient in need thereof having such a bladder cancer. These resistant bladder cancers may be any one the particular bladder cancers that will now be presented.

In another embodiment, bladder cancer is a Non Muscle Invasive Bladder Cancer (NMIBC). In this embodiment, a composition as disclosed herein is used for treating NMIBC or administered to a patient in need thereof, i.e. having NMIBC.

For NMIBC, the gold standard is BCG therapy, or chemotherapy (e.g. epirubicine, mitomycine, gemcitabine). This type of cancer may be resistant to standard immunotherapy (BCG and/or ICI such as an anti-PD1 or an anti-PD-L1, especially with an anti-PD1 or an anti-PD-L1 monoclonal antibody and the like) and/or to chemotherapy (e.g. epirubicine, mitomycine, gemcitabine). Thus, the treatment also comprises treating a NMIBC cancer that is resistant to standard immunotherapy and/or to chemotherapy.

In another embodiment, bladder cancer is Muscle Invasive Bladder Cancer (MIBC). In this embodiment, a composition as disclosed herein is used for treating MIBC or administered to a patient in need thereof, i.e. having MIBC.

For MIBC, the gold standard is chemotherapy, especially MVAC chemotherapy (Methotrexate, Vinblastine, Doxorubicin, Cisplatin), possibly combined with ICI (mainly anti-PD1 or an anti-PD-L1, especially with an anti-PD1 or an anti-PD-L1 monoclonal antibody and the like), possibly combined to cystectomy. However, some of patients are possibly not eligible or reluctant to chemotherapy, especially MVAC, and/or immunotherapy (ICI), and/or to cystectomy. Thus, the treatment also comprises treating a MIBC cancer that is not eligible or reluctant to chemotherapy and/or immunotherapy (ICI) and/or cystectomy.

In another embodiment, bladder cancer is Metastatic Muscle Invasive Bladder Cancer (MMIBC). In this embodiment, a composition as disclosed herein is used for treating MMIBC or administered to a patient in need thereof, i.e. having MMIBC.

For this type of cancer, the gold standard is chemotherapy and immunotherapy such as with ICI (mainly anti-PD1 or an anti-PD-L1, especially with an anti-PD1 or an anti-PD-L1 monoclonal antibody and the like). However, some patients are not eligible to chemotherapy and/or are resistant to immunotherapy. Thus, the treatment also comprises treating a MMIBC that is not eligible to chemotherapy and/or resistant to immunotherapy such as anti-PDL1 and anti-PD1.

The composition usable in the treatment of a bladder cancer as disclosed herein may be in particular a composition comprising double-stranded RNAs (dsRNA) as active principle, wherein said dsRNA has two complementary strands, comprising at least one block or homopolymer of poly A and the complementary block or homopolymer of poly U, each block comprising at least 15, 20, 25 or 30 Å, or U, and each strand having a determined length of between 50 and 200 bases, preferably between 55 and 200 bases, and the composition comprises a pharmaceutically acceptable vehicle, carrier or excipient.

In particular, the composition usable in the treatment of a bladder cancer as disclosed herein may be a composition comprising dsRNA consisting of, or essentially consisting of, dsRNA having two complementary strands, comprising at least one block or homopolymer of poly A and the complementary block or homopolymer of poly U, each block comprising at least 15, 20, 25 or 30 Å, or U, and each strand having a determined length of between 50 and 200 bases, preferably between 55 and 200 bases, and a pharmaceutically acceptable vehicle, carrier or excipient.

Advantageously, all the strands or substantially all the strands in the composition have the predetermined length. Preferably, the strands and the dsRNAs are synthetic. The composition may comprise 0.01 to 100 mg of said dsRNA per ml of composition.

Preferably, said dsRNA is of Formula (II), (Ill), (IV), (V), or (VI) as disclosed herein, or a defined mixture of at least two different dsRNA of Formula (II), (Ill), (IV), (V), or (VI). More particularly, said dsRNA is of formula (II), (Ill) or (IV), preferably of formula (III), as disclosed herein.

In a modality, said dsRNA is of formula (III), wherein P and R are both I, and Y and Z are both C.

The definitions given supra for these formulas (II), (Ill), (IV), (V), and (VI) apply to this subject-matter.

All these compositions may be used in this treating of bladder cancer, especially of the different types of bladder cancers as disclosed herein.

In particular, the dsRNA is dsRNA ID #422, 432, 442, 452, 532, 533, or a mixture of at least two of them. In an embodiment, the composition comprises dsRNA comprising dsRNA ID #422, 432, 442, 452, 532, 533, or a mixture of at least two of them, as active principle, or the dsRNA in the composition consists of, or essentially consists of dsRNA ID #422, 432, 442, 452, 532, 533, or a mixture of at least two of them. In an embodiment, the composition comprises dsRNA comprising dsRNA ID #532 as active principle, or the dsRNA in the composition consists of, or essentially consists of, dsRNA ID #532. These compositions may be used in this treating of bladder cancer, especially of the different types of bladder cancers as disclosed herein.

The present invention also relates to the use of one of these dsRNAs: dsRNA ID #422, 432, 442, 452, 532, 533, or a mixture of at least two of them, for example of dsRNA ID #532, for treating a bladder cancer as disclosed herein.

The present invention also relates to a method of treatment of, or the use for treating, an epithelial cell cancer or epithelial cancer, in particular epithelial Lung cancer, for example of Small-Cell Lung Cancer or Non-Small-Cell Lung Cancer. In a specific embodiment, the Lung cancer is Non-Small-Cell Lung Cancer. In the method of treatment, this epithelial cancer may be treated by a composition as disclosed herein administered in sufficient amount to a patient in need thereof. A composition as disclosed herein may be for use in treating this epithelial cancer in a patient.

The composition usable in the treatment of such epithelial cancer, in particular the different types of Lung cancers as disclosed herein, especially Non-Small-Cell Lung Cancer, comprises as active principle, dsRNA of Formula (II), (Ill), (IV), (V), or (VI) as disclosed herein, or a defined mixture of at least two different dsRNA of Formula (II), (Ill), (IV), (V), or (VI).

In particular, the composition comprises dsRNA consisting of, or essentially consisting of, dsRNA of Formula (II), (Ill), (IV), (V), or (VI) as disclosed herein, or a defined mixture of at least two different dsRNA of Formula (II), (Ill), (IV), (V), or (VI).

More particularly, the dsRNA is of formula (II), (Ill) or (IV), preferably of formula (III), as disclosed herein.

In a modality, the dsRNA is of formula (III), wherein P and R are both I, and Y and Z are both C.

The definitions given supra for these formulas (II), (Ill), (IV), (V), and (VI) apply to this subject-matter.

In particular, the dsRNAs is dsRNA ID #422, 432, 442, 452, 532, 533, or a mixture of at least two of them. In an embodiment, the composition comprises dsRNA comprising dsRNA ID #422, 432, 442, 452, 532, 533, or a mixture of at least two of them, as active principle, or the dsRNA in the composition consists of, or essentially consists of dsRNA ID #422, 432, 442, 452, 532, 533, or a mixture of at least two of them. In an embodiment, the composition comprises dsRNA comprising dsRNA ID #532 as active principle, or the dsRNA in the composition consists of, or essentially consists of, dsRNA ID #532. These compositions may be used in this treating of epithelial cancer, especially of the different types of Lung cancers as disclosed herein, in particular Non-Small-Cell Lung Cancer.

The present invention also relates to the use of one of these dsRNAs: dsRNA ID #422, 432, 442, 452, 532, 533, or a mixture of at least two of them, for example of dsRNA ID #532, for treating an epithelial cancer as disclosed herein.

Described are methods for preventing, managing, treating or ameliorating cancer that has the potential to metastasize or has metastasized to an organ or tissue (e.g., bone) or one or more symptoms thereof. Also described is a TLR3 agonist for use in preventing, managing, treating or ameliorating cancer that has the potential to metastasize or has metastasized to an organ or tissue (e.g., bone) or one or more symptoms thereof.

Said methods and uses comprise administering to a subject in need thereof one or more doses of a prophylactically or therapeutically amount of a TLR3 agonist according to the invention. Preferably, the TLR3 agonist is administered more than once. Optionally, the TLR3 agonist is administered at an interval of less than one month, less than three weeks, less than two weeks, or less than one week. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

The present specification provides methods for preventing, managing, treating or ameliorating cancer or one or more symptoms thereof, said methods comprising administering to a subject in need thereof a dosage of a prophylactically or therapeutically effective amount of a TLR3 agonist in combination with the administration of a dosage of a prophylactically or therapeutically effective amount of one or more other agents useful for cancer therapy. The specification also concerns a TLR3 agonist for use in preventing, managing, treating or ameliorating cancer, wherein said TLR3 agonist is used in combination with one or more agents useful for cancer therapy. Preferably, the TLR3 agonist is administered more than once. Optionally, the TLR3 agonist is administered at an interval of less than one month, less than three weeks, less than two weeks, or less than one week. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

Each compound of the combinations or pharmaceutical compositions according to the invention can be administered separately, sequentially or simultaneously.

In an embodiment, the TLR3 agonist of the invention is administered before or after the other chemotherapeutic agent, or at the same time.

In an embodiment, the composition of TLR3 agonist of the invention is administered before or after an Immune Check Point Inhibitor (ICI), or at the same time.

As disclosed herein, the composition of TLR3 agonist of the invention may be administered to a patient in need thereof for treating a cancer being resistant to Immunotherapy such as with ICI, mainly anti-PD1 or an anti-PD-L1, especially a cancer being resistant to an anti-PD1 or an anti-PD-L1 monoclonal antibody and the like (by "and the like", it is meant derivatives of a monoclonal antibody, such as, but not limited thereto, binding fragment thereof, bispecific antibody, antibody-drug-conjugate, etc.). However, the TLR3 agonist may also be administered to a patient in need thereof for treating a cancer responding to such immunotherapy or to a patient in need thereof in a combined therapy with such an Immunotherapy.

In all these situations, it may be beneficial to the patient to be treated both by Immunotherapy and by a composition according to the invention. The Applicant demonstrated that the combination of an anti-PD-L1 monoclonal antibody and a TLR3 agonist composition of the invention generates good results and even synergism. It is thus herein proposed to combine treatment with a TLR3 agonist composition of the invention and Immunotherapy such as with ICI, mainly anti-PD1 or an anti-PD-L1, especially with an anti-PD1 or an anti-PD-L1 monoclonal antibody and the like, in all these situations, including in a patient resistant to Immunotherapy.

Thus, the invention also relates to a method of treatment of cancer as disclosed herein in a patient in need thereof comprises administering to a patient in need thereof, a sufficient amount of a composition of the invention, and of at least one ICI or composition containing said ICI. This encompasses that the TLR3 agonist composition and the ICI are administered simultaneously (including punctual administration; prolonged administration, such as by long infusion, implantable pouch; and delayed-type vehicles or implants) or within an interval of time such that both active principles (TLR3 agonist and ICI) are present and active at a same time.

In an embodiment, the method is for treating a bladder cancer as disclosed herein, such as NMIBC, MIBC and MMIBC, bladder cancer having resistance to ICI, including NMIBC, MIBC and MMIBC having resistance to ICI. In this embodiment, the composition comprising dsRNAs is in particular as disclosed herein in part entitled "Cancer and Therapeutic Methods and Uses for".

Another object of the invention is the use of a TLR3 agonist composition according to the invention and of an ICI for combined therapy for treating a patient against a cancer as disclosed herein; the ICI may in particular be an inhibitor of PD1 or of PD-L1, especially it is an anti-PD1 or an anti-PD-L1 monoclonal antibody and the like. The cancer is preferably a cancer expressing TLR3 as disclosed herein.

In an embodiment, it is a bladder cancer as disclosed herein, such as NMIBC, MIBC and MMIBC, bladder cancer having resistance to ICI, including NMIBC, MIBC and MMIBC having resistance to ICI. In this embodiment, the composition comprising dsRNAs is in particular as disclosed herein in part entitled "Cancer and Therapeutic Methods and Uses for".

The ICI may in particular be an inhibitor of PD1 or of PD-L1; especially it is an anti-PD1 or an anti-PD-L1 monoclonal antibody and the like. It may be for example any antibody currently in use in clinic or any antibody in development. Such antibodies are disclosed herein. In a modality, the antibody is MPDL3280A/RG7446 (anti-PD-L1 mAb, Atezolizumab, Roche/Genentech).

In the combined therapy, the TLR3 agonist composition and the ICI may be administered simultaneously (including punctual administration; prolonged administration, such as by long infusion, implantable pouch; and delayed-type vehicles or implants) or within an interval of time such that both active principles are present and active at a same time. The skilled person is able to determine this based on the half-life of both active principles.

Preferably, the combined therapy provides for the administration of:

- a TLR3 agonist composition wherein the dsRNA is of Formula (II), (Ill), (IV), (V), (VI) as disclosed herein, more particularly, of formula (II), (Ill) or (IV), preferably of formula (III), as disclosed herein; and
- an anti-PD1 or an anti-PD-L1 monoclonal antibody and the like.

Preferably, the combined therapy provides for the administration of:

- a TLR3 agonist composition wherein the dsRNA is of formula (III), wherein P and R are both I, and Y and Z are both C; and
- an anti-PD1 or an anti-PD-L1 monoclonal antibody and the like.

Preferably, the combined therapy provides for the administration of:

- a TLR3 agonist composition wherein the dsRNA is dsRNA ID #422, 432, 442, 452, 532 or 533; and
- an anti-PD1 or an anti-PD-L1 monoclonal antibody and the like.

Preferably, the combined therapy provides for the administration of:

- TLR3 agonist composition wherein the dsRNA is dsRNA ID #532; and
- an anti-PD1 or an anti-PD-L1 monoclonal antibody and the like.

In one embodiment, a dsRNA is administered to a subject using a dose regimen that maintains the plasma concentration of the agonist at a desirable level. In a specific embodiment, the plasma concentration of the dsRNA is maintained at about 10 μg/ml, 15 μg/ml, 20 μg/ml, 25 μg/ml, 30 μg/ml, 35 μg/ml, 40 μg/ml, 45 μg/ml or 50 μg/ml. The plasma concentration that is desirable in a subject will vary depending on several factors including, but not limited to, the nature of the cancer, the severity of the cancer, and the circulation half-life (stability) and binding affinity of the TLR3 agonist.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight.

In particular, the doses of TLR3 agonist according to the invention that can be administered are between 0.1 mg/kg and 10 mg/kg of body weight, for example 0.1, 0.5, 1, 2, 3, 4, 5, 6, 7, 8, 9 or 10 mg/kg of body weight.

Preferably, a therapeutically effective amount of a TLR3 agonist (optionally in combination with another therapeutic agent or therapeutic protocol) reduces the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as PBS.

In the scope of the present invention, it has to be understood that "a TLR3 agonist for use" is equivalent to "the use of a TLR3 agonist" and in particular that "a TLR3 agonist for use in the treatment of" is equivalent to "the use of a TLR3 agonist for the treatment of". The invention also encompasses "the use of a TLR3 agonist for the manufacture of a medicament intended for the treatment of" in accordance with the present disclosure.

Types of Cancers

In various embodiments, the present specification provides methods for determining treatment regimens for cancer subjects. The methods can be used to determine treatment regimens of any cancer, or tumor, for example, but not limited to, malignancies and related disorders include but are not limited to the following, and expressing TLR3.

Accordingly, the methods are useful in the treatment of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyosarcoma, and osteosarcoma; and other tumors, including melanoma, xenoderma pigmentosum, keratoacanthoma, seminoma, thyroid follicular cancer and teratocarcinoma. In specific embodiments, malignancy or dysproliferative changes (such as metaplasias and dysplasias), or hyperproliferative disorders, are treated in the ovary, bladder, breast, colon, lung, skin, pancreas, or uterus. In other specific embodiments, sarcoma, melanoma, or leukemia is treated.

The methods are used for TLR3 positive solid tumors. Example of tumors include breast, colon, ovarian, lung, brain and prostate cancers and melanoma.

Preferably the methods are directed at treating breast cancer, lung cancer, such as non-small cell lung cancer, and bladder cancer.

Synthesis of dsRNA

Standard synthesis methods may be used to produce dsRNA compositions according to the specifications of the invention. As an example, standard phosphoramidite solid-phase synthesis technology may be used. See M. D. Matteucci et al., Tetrahedron Lett. 22, 1859-1862 (1981). 2'-ACE RNA synthesis chemistry may be used and based on a protecting group scheme as disclosed in S. A. Scaringe, Ph.D Thesis, University of Colorado, 1996. Dharmacon™ technology for RNAi, Gene Expression & Gene Editing, 2'-ACE RNA synthesis chemistry of GE Healthcare may be used. Methods such as electrophoresis on gel, such as the acrylamide gel used in the examples, may be used to check purity.

FIGURES

FIG. 1: dsRNA profile on a 8% acrylamide gel (TBE 1×) of 50 bp dsRNAs and commercial Poly(A:U). 5 μg of dsRNA (dsRNA ID #s 345, 397, 398, 415, 418, 405, 411, 412, 413, as defined in Table 1) and commercial Poly(A:U) were loaded on 8% acrylamide gel and stained with BET. Data are representative of 9 out of 17 50 bp dsRNA tested.

Figure 2:
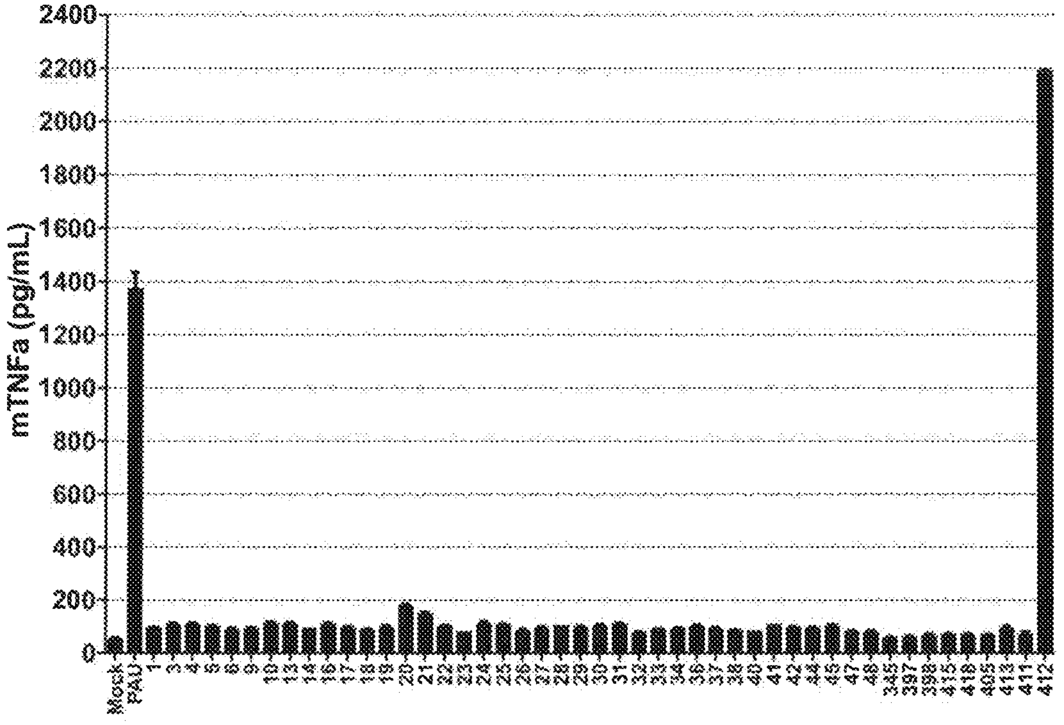

FIG. 2: Secretion of TNF alpha by mouse macrophages RAW264.7 cells in response to 50 bp dsRNA alone. RAW264.7 cells were treated for 24 hours with 10 μg/mL of each dsRNA, as defined in Table 1, and mTNF alpha secretion was measured with ELISA. Data are representative of two independent assays using two different batches of the 50 bp dsRNA ID #412.

Figure 3:
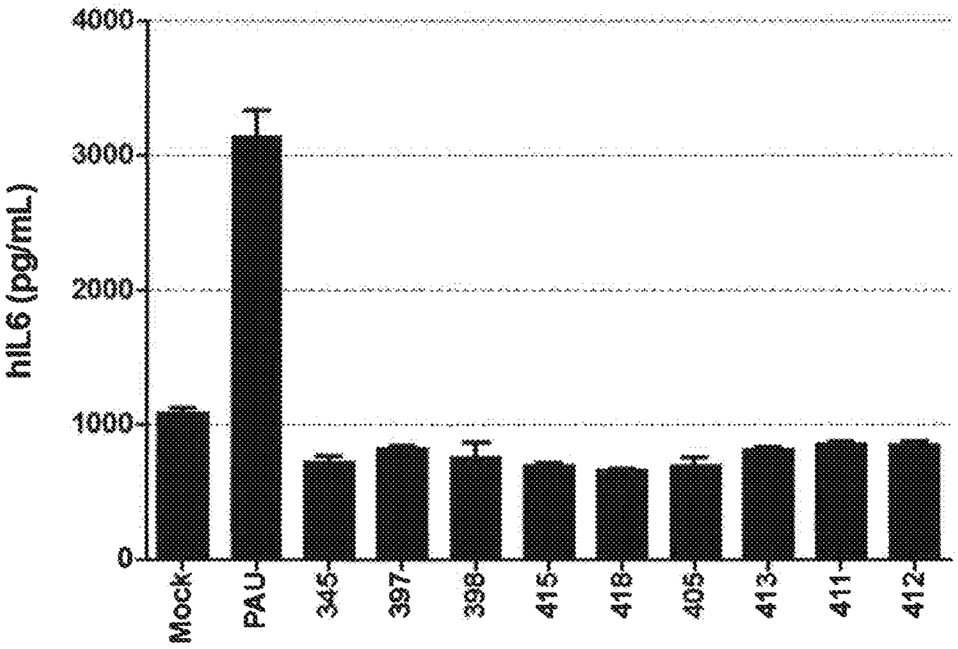
Figure 4:
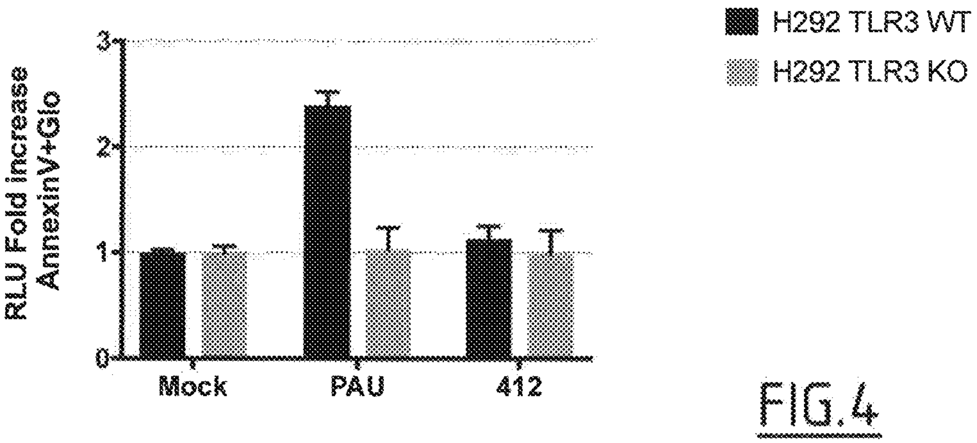

FIG. 3: Secretion of IL6 by human non-small cell lung cancer cells NCI-H292 after treatment with 9 50 bp dsRNA alone. NCI-H292 cells were treated for 24 hours with 10 μg/mL of each dsRNA, as defined in Table 1, and hIL6 secretion was measured with ELISA. Data are representative of three independent assays.

FIG. 4: 50 bp dsRNA ID #412 does not trigger death in human non-small cell lung cancer cells NCI-H292. NCI-H292 cells were treated for 24 hours with 50 μg/mL of the dsRNA. AnnexinV positives cells were measured by chemiluminescence (kit Annexin V-Glo, Promega). Data are representative of three independent assays using two different batches of the 50 bp dsRNA ID #412.

FIG. 5: dsRNA profile on a native 6% acrylamide gel (TBE 1×) of the dsRNA ID #s 412, 432, 452 and commercial Poly(A:U). 1 μg of dsRNA ID #s 412 (Poly(A:U) 50pb), 432 (Poly(A:U) 70pb), 452 (Poly(A:U) 90pb) (as defined in Tables 1 and 2) and commercial Poly(A:U) were loaded on 6% acrylamide gel and stained with BET. Data representative of two independent experiments.

Figure 6:
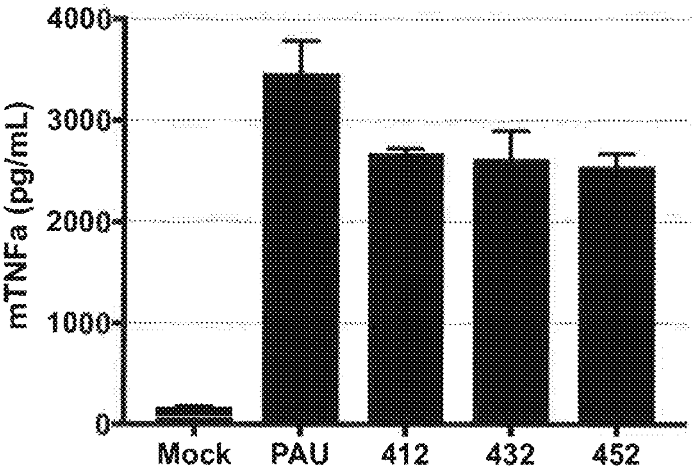
Figure 7:
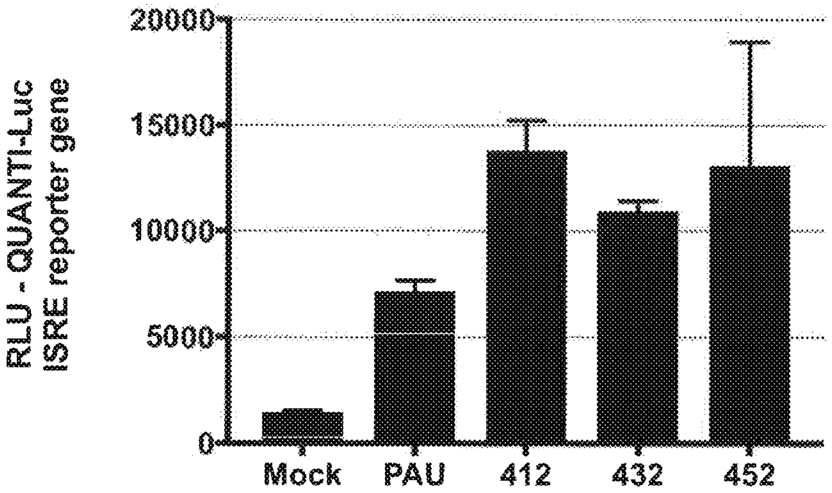

FIG. 6: Secretion of TNF alpha by mouse macrophages RAW264.7 cells in response to Poly(A:U) of increasing size alone. RAW264.7 cells were treated for 24 hours with 10 μg/mL of each dsRNA, as defined in Tables 1 and 2, and mTNF alpha secretion was measured with ELISA. Data are representative of three independent assays.

FIG. 7: Poly(A:U) of increasing sizes alone activate the ISRE-reporter gene in mouse macrophages RAW264.7. RAW264.7 cells were treated for 24 hours with 50 μg/mL with the indicated dsRNA, as defined in Tables 1 and 2. ISRE-driven bioluminescence was measured (QUANTI-luc, Invivogen). Data are representative of three independent assays.

Figure 8:
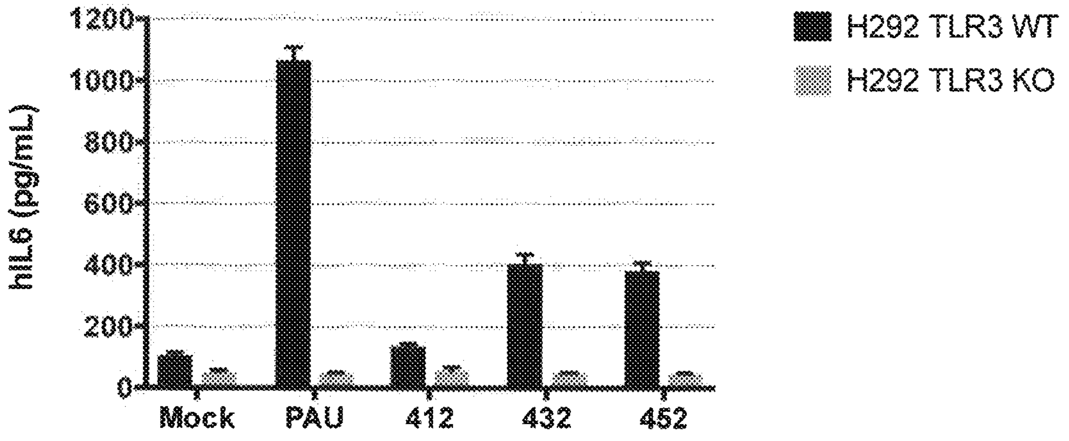

FIG. 8: Poly(A:U) of increasing sizes alone trigger the TLR3-dependant secretion of IL6 by human non-small cell lung cancer cells NCI-H292. WT or TLR3 KO NCI-H292 cells were treated for 24 hours with 10 μg/mL of each dsRNA, as defined in Tables 1 and 2, and hIL6 secretion was measured with ELISA. Data are representative of three independent assays.

Figure 9:
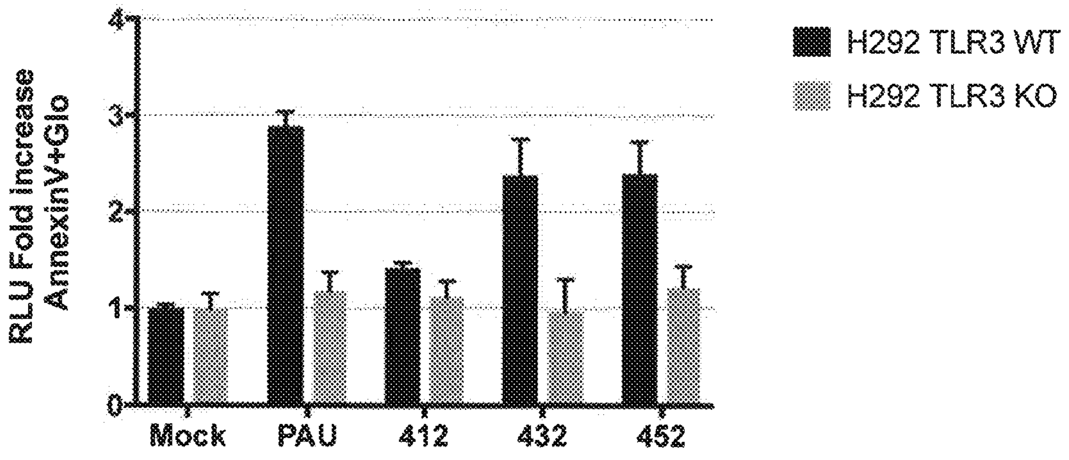

FIG. 9: Poly(A:U) of increasing sizes alone trigger the TLR3-dependant death of human non-small cell lung cancer cells NCI-H292. NCI-H292 cells were treated for 24 hours with 50 μg/mL of the indicated dsRNAs, as defined in Tables 1 and 2. AnnexinV positives cells were measured by chemiluminescence (kit Annexin V-Glo, Promega). Data are representative of three independent assays.

FIG. 10: dsRNA profile on a native 6% acrylamide gel (TBE 1×) of the dsRNA ID #422, 432, 442, 532, 533, 534, 535, and commercial Poly(A:U). 1 μg of each one of these dsRNA and commercial Poly(A:U) were loaded on 6% acrylamide gel and stained with BET. Data representative of two independent experiments.

FIG. 11: Secretion of TNF alpha by mouse macrophages RAW264.7 cells in response to commercial Poly(A:U) and dsRNA ID #422, 432, 442, 532, 533, 534, 535. RAW264.7 cells were treated for 24 hours with 10 μg/mL of each dsRNA and mTNF alpha secretion was measured with ELISA. Data are representative of two independent assays.

FIG. 12: TLR3-dependant secretion of IL6 by human non-small cell lung cancer cells NCI-H292, in response to commercial Poly(A:U) and dsRNA ID #422, 432, 442, 532, 533, 534, 535. WT or TLR3 KO NCI-H292 cells were treated for 24 hours with 10 μg/mL of each dsRNA and hIL6 secretion was measured with ELISA. Data are representative of at least two independent assays.

FIG. 13: TLR3-dependant death of human non-small cell lung cancer cells NCI-H292, in response to commercial Poly(A:U) and dsRNA ID #422, 432, 442, 532, 533, 534, 535. NCI-H292 cells were treated for 24 hours with 50 μg/mL of the indicated dsRNAs. AnnexinV positive cells were measured by chemiluminescence (kit Annexin V-Glo, Promega). Data are representative of two independent assays.

Figure 14:
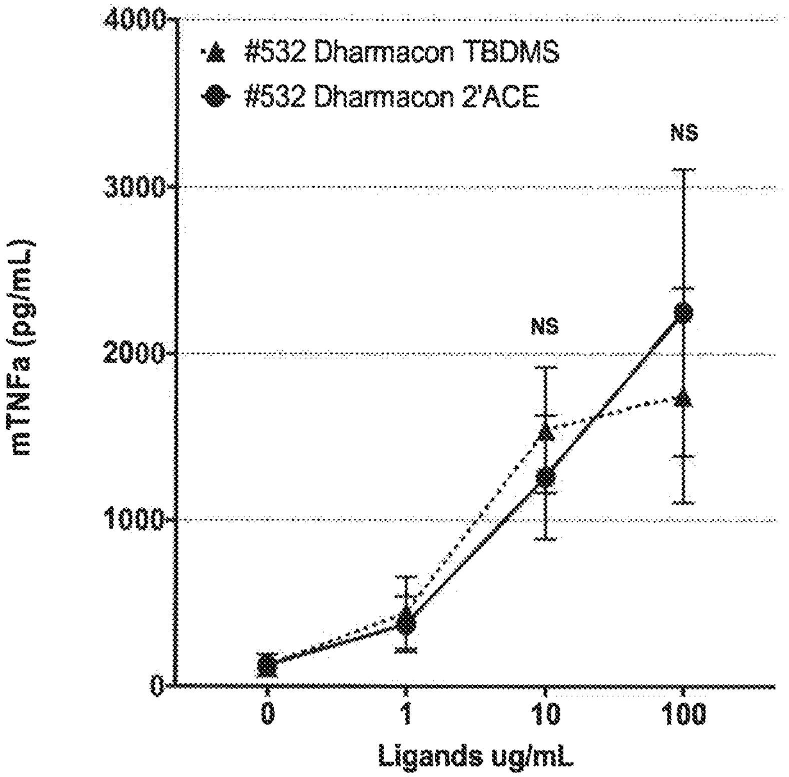

FIG. 14: Secretion of TNF alpha by mouse macrophages RAW264.7 cells in response to dsRNA ID #532 made from two different chemical manufacturing technologies. RAW264.7 cells were treated for 24 hours with a dose-response from 1 to 100 μg/mL of the indicated dsRNA ID #532 and mTNF alpha secretion was measured with ELISA. Data are the mean of at least three independent assays and are representative from at least six independent assays.

Figure 15:
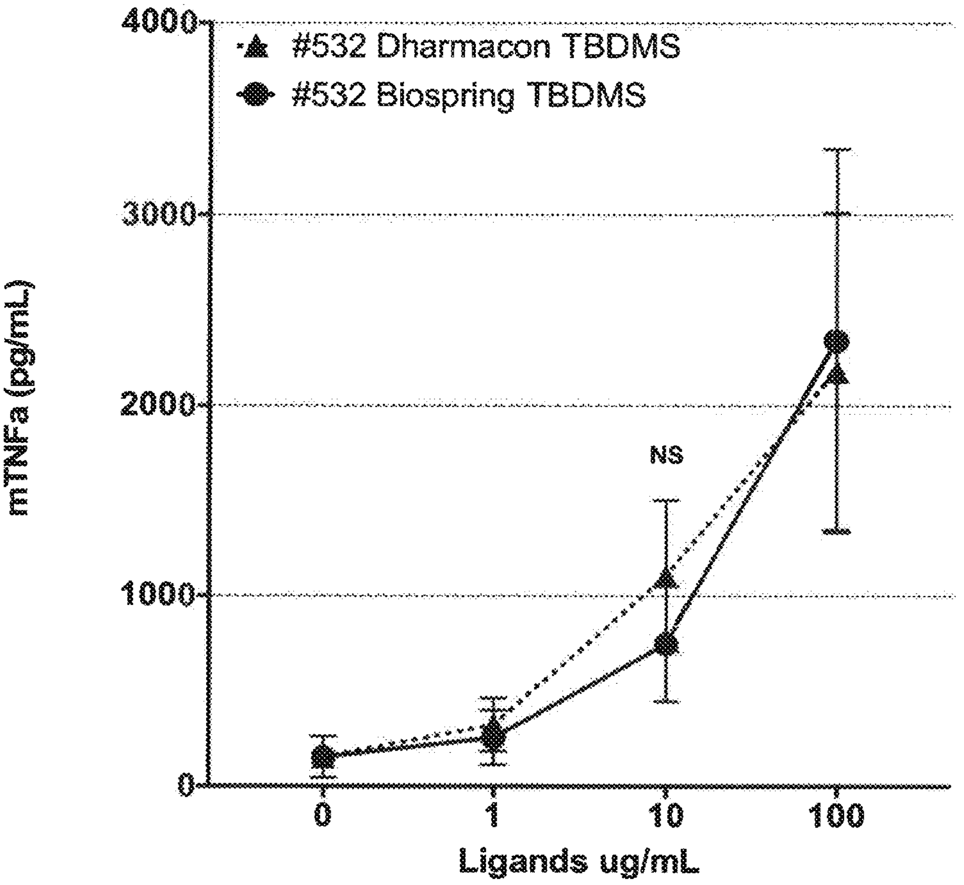

FIG. 15: Secretion of TNF alpha by mouse macrophages RAW264.7 cells in response to dsRNA ID #532 made from two different manufacturers companies. RAW264.7 cells were treated for 24 hours with a dose-response from 1 to 100 μg/mL of the indicated dsRNA ID #532 and mTNF alpha secretion was measured with ELISA. Data are the mean of at least five independent assays.

Figure 16:
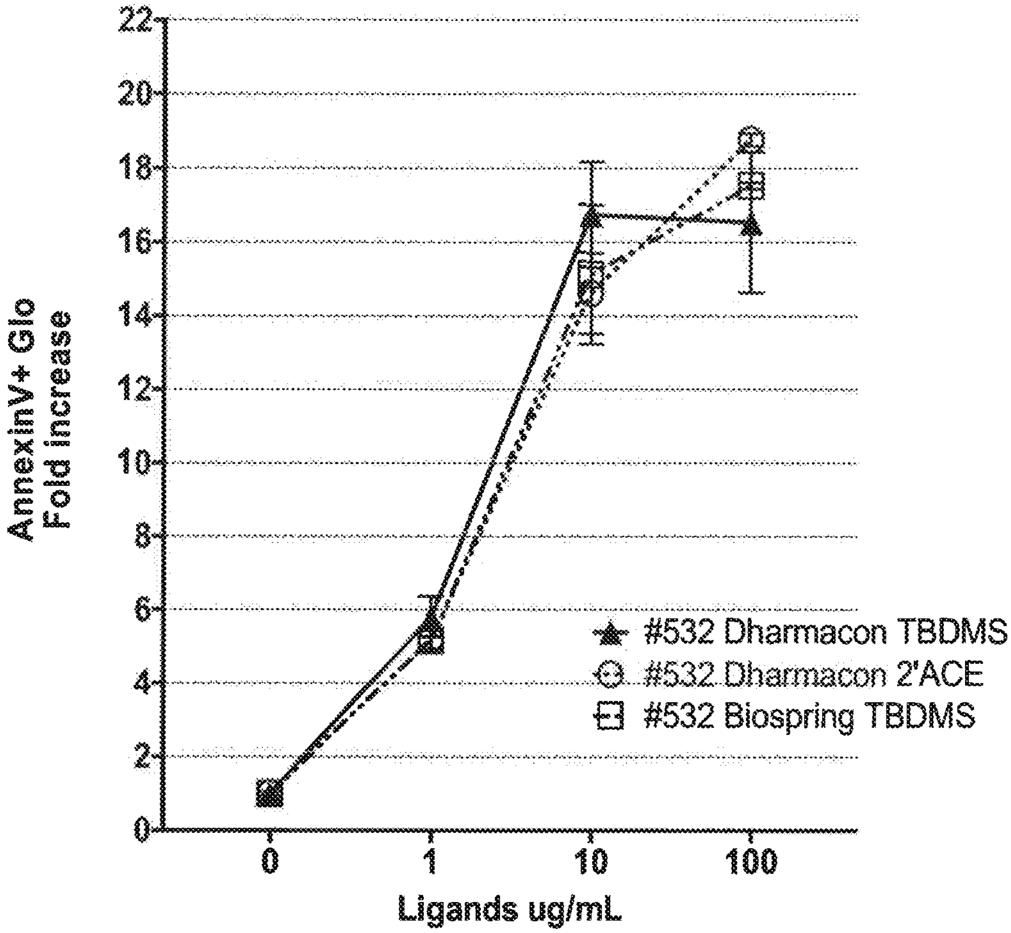

FIG. 16: dsRNA ID #532 made from two different chemical synthesis technologies or from two different manufacturers companies trigger the same level of death of human non-small cell lung cancer cells NCI-H292. NCI-H292 cells were treated for 24 hours with a dose-response from 1 to 100 μg/mL of the indicated dsRNAs. AnnexinV positives cells were measured by chemiluminescence (kit Annexin V-Glo, Promega). Data are representative of at least four independent assays.

Figure 17:
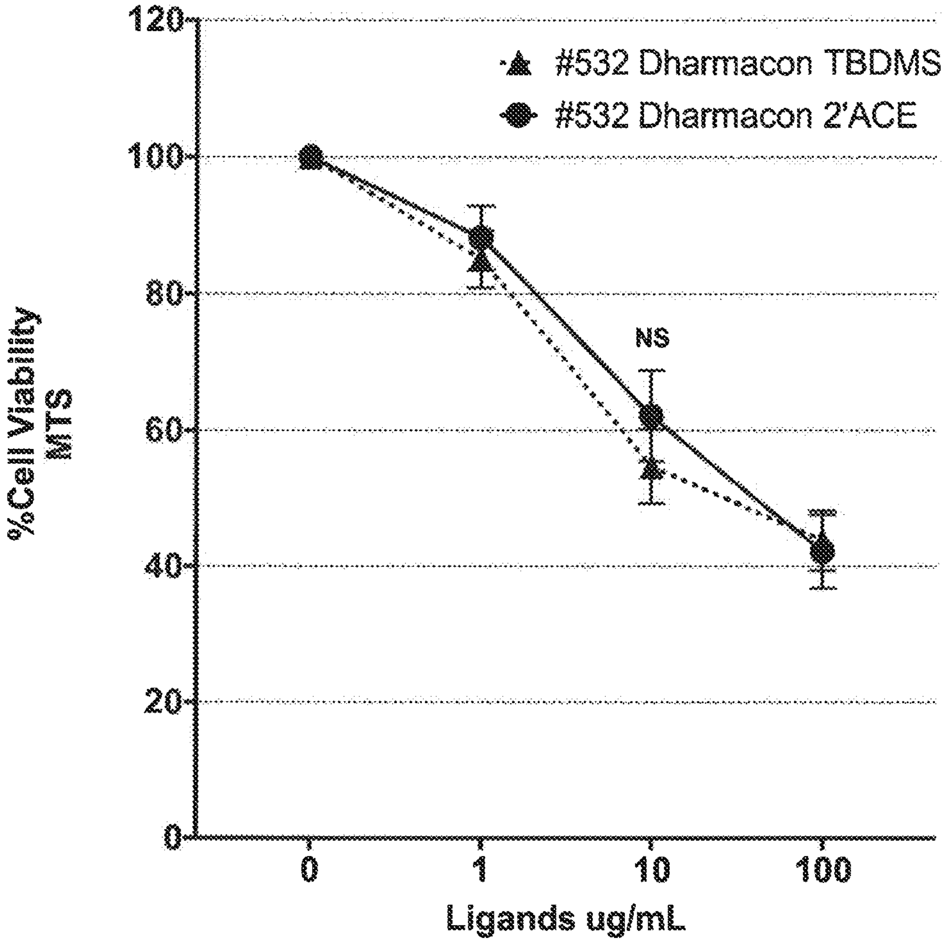

FIG. 17: dsRNA ID #532 made from two different chemical synthesis technologies trigger the same level of cell viability reduction of human non-small cell lung cancer cells NCI-H292. NCI-H292 cells were treated for 24 hours with a dose-response from 1 to 100 μg/mL of the indicated dsRNAs. Cell viability assays were measured by MTS (kit Cell Titer Aqueous solution, Promega). Data are representative of at least four independent assays.

Figure 18:
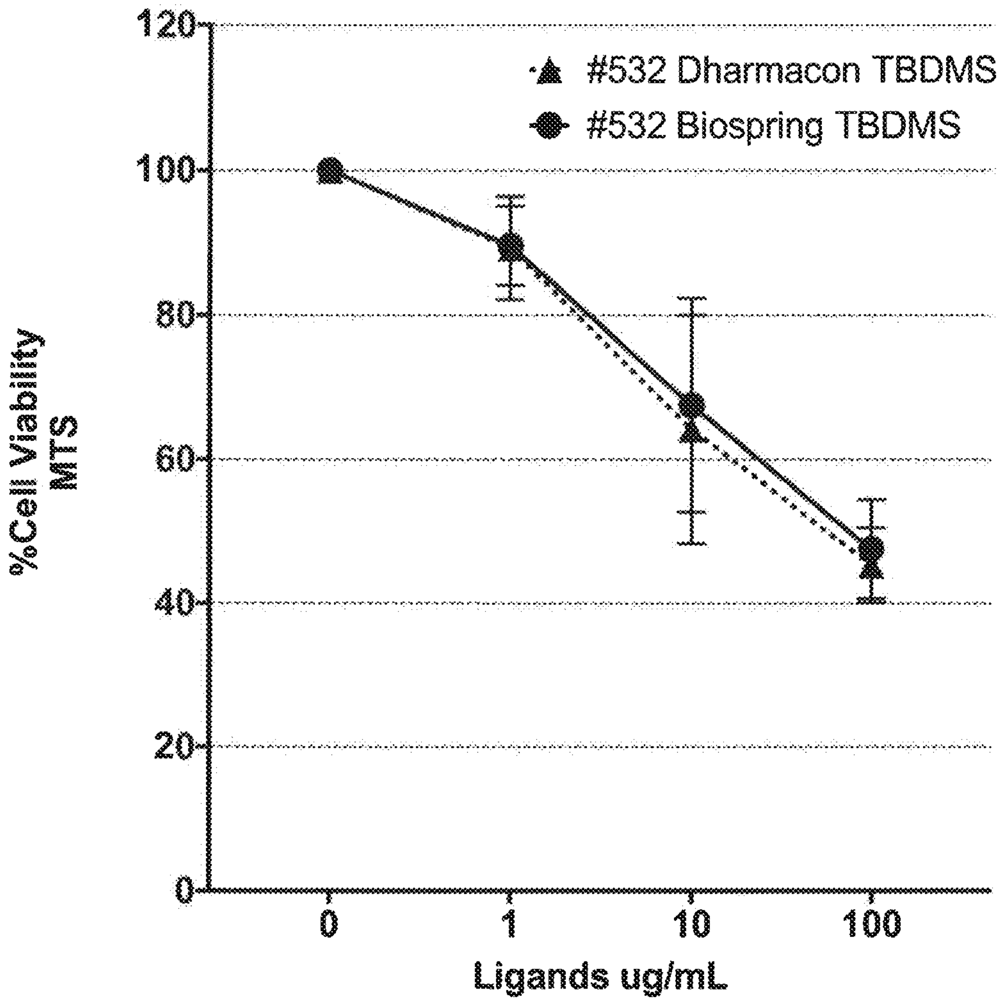

FIG. 18: dsRNA ID #532 made from two different manufacturers companies trigger the same level of cell viability reduction of human non-small cell lung cancer cells NCI-H292. NCI-H292 cells were treated for 24 hours with a dose-response from 1 to 100 μg/mL of the indicated dsRNAs. Cell viability assays were measured by MTS (kit Cell Titer Aqueous solution, Promega). Data are representative of at least five independent assays.

Figure 19:
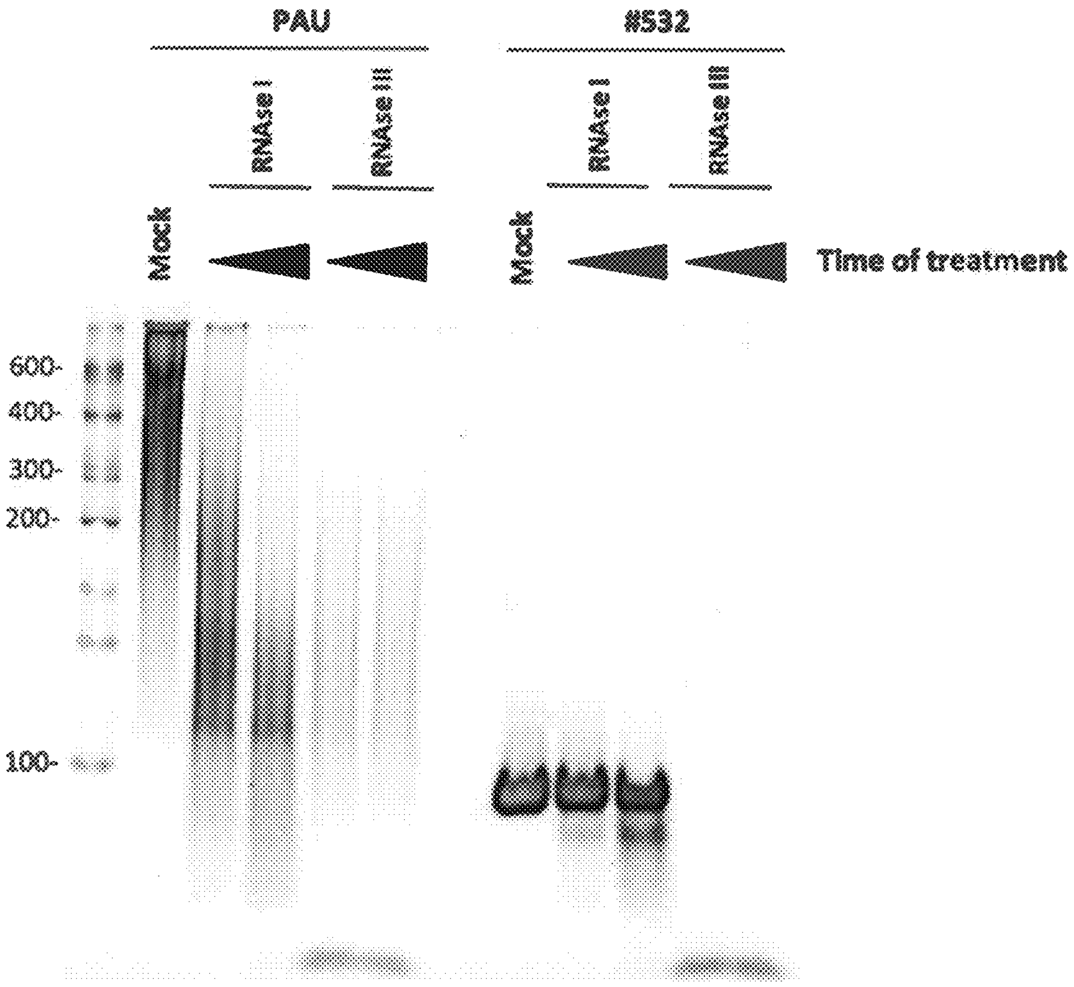

FIG. 19: dsRNA profile on a native 6% acrylamide gel (TBE 1×) of the Poly(A:U) and dsRNA ID #532 after digestion with either RNAse I or RNAse III. 1 μg of dsRNA and commercial Poly(A:U) were loaded on 6% acrylamide gel and stained with BET. Data are representative of at least two independent assays.

Figure 20:
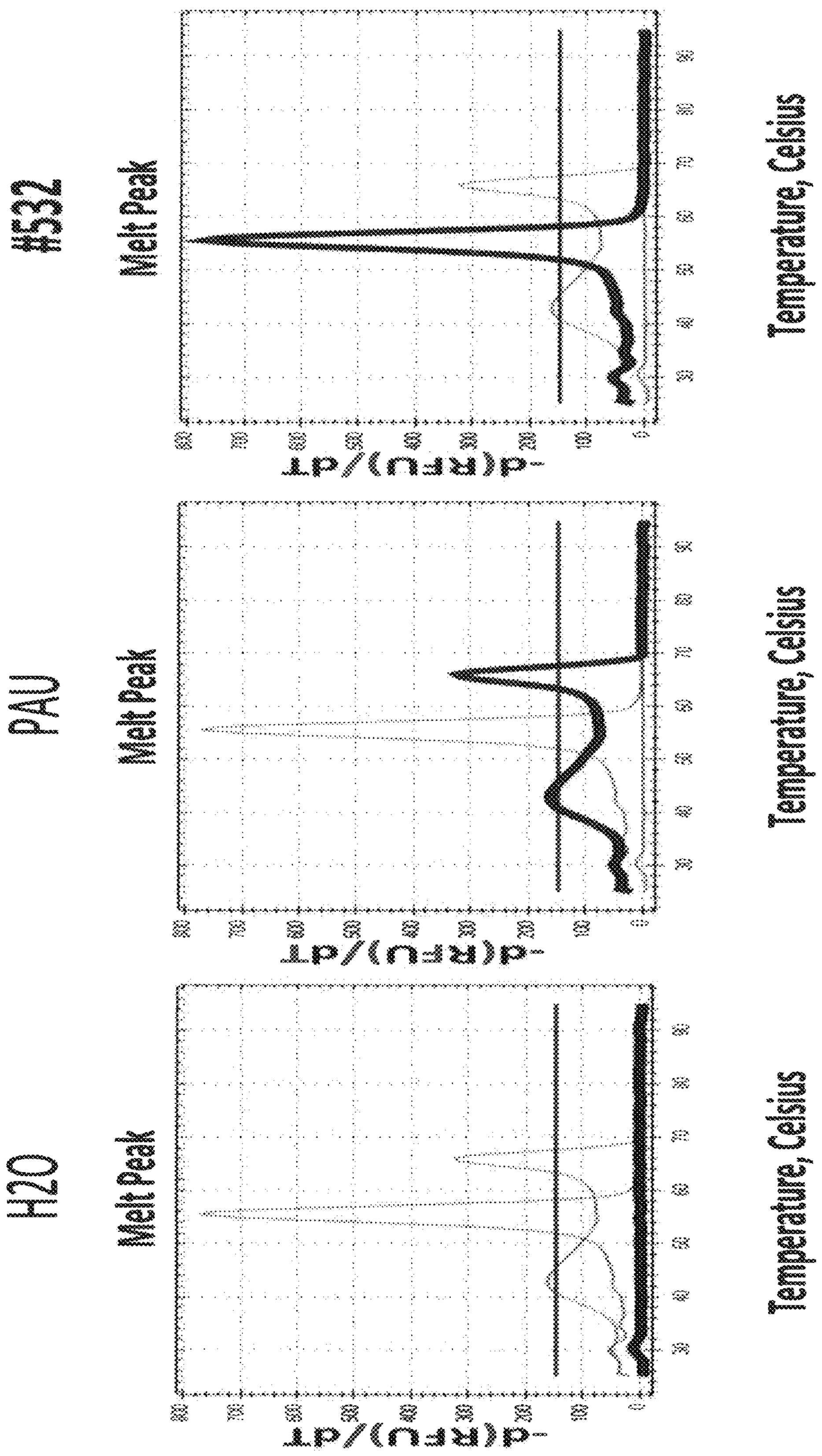

FIG. 20: dsRNA Tm calculation profile of the Poly(A:U) and the dsRNA ID #532. 1 μg of dsRNA were mix with a SyBr green Q-PCR mix and melting curve analysis were performed. Data are representative of at least three independent assays. In abciss, temperature in ° Celsius. In ordinate, −d(RFU)/dT. The Melt peak is indicated.

Figure 21:
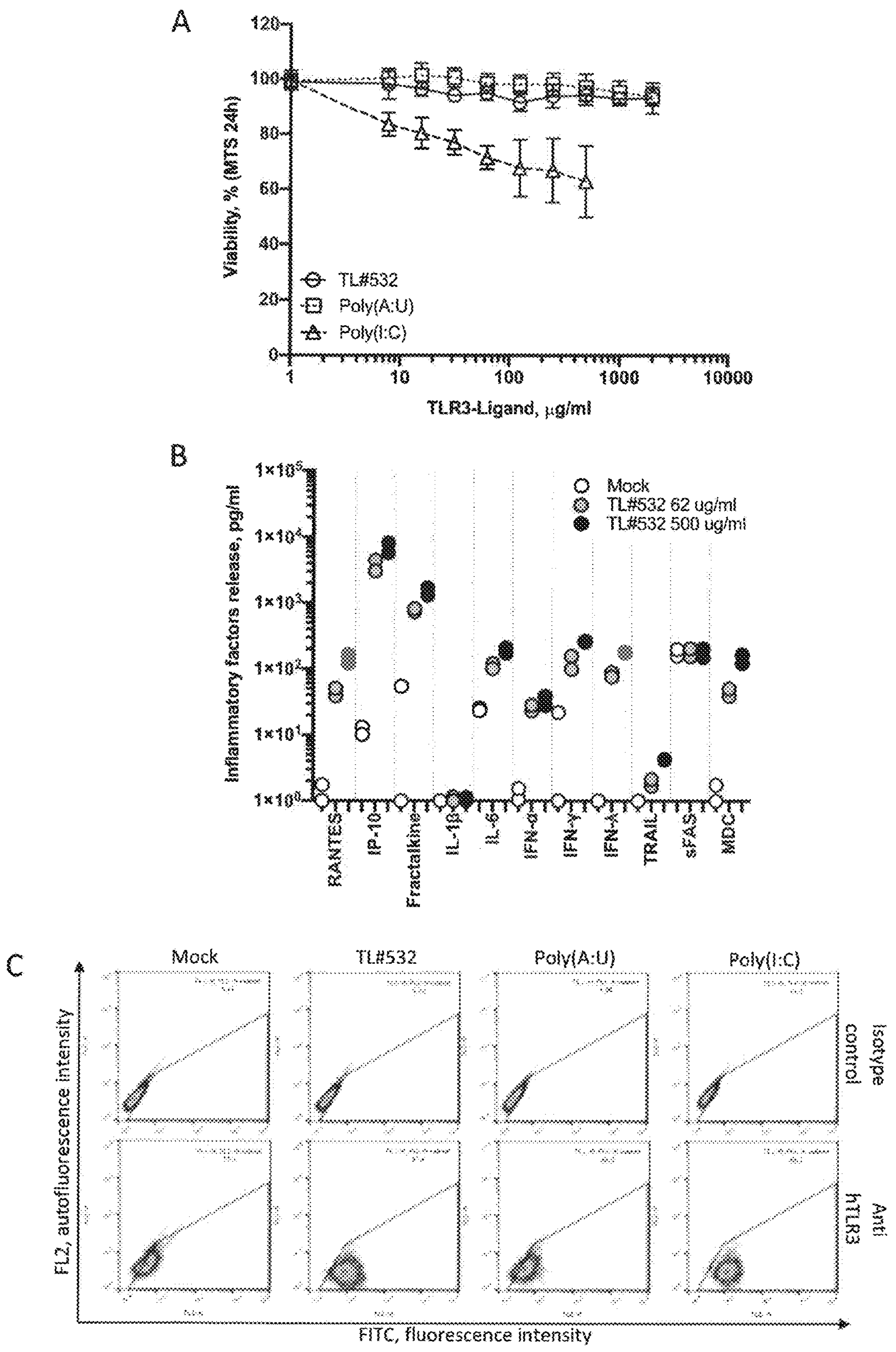

FIG. 21: DsRNA ID #532 (TL #532) has no toxicity but induces antitumor inflammation and over expression of TLR3 within normal urothelial bladder primary cells (UBPC). (A) Toxicity of TLR3 ligands on UBPC: UBPC were treated for 24 hours with a dose-response from 8 to 2000 μg/mL of the indicated dsRNAs. Cell viability assays was measured by MTS (kit Cell Titer Aqueous solution, Promega). Data are the mean of two independent assays. (B) TL #532 induces antitumor inflammation on normal UBPC: Supernatants of UPBC either mock treated of treated with TL #532 were collected at 24 h post-treatment and submitted to Multiparametric ELISA from Mesoscale Diagnostics. Results are shown as single dot per independent experiment on 2 different healthy donors. (C) TL #532 induces TLR3 overexpression on normal UBPC: UPBC were treated for 24 hours using the indicated dsRNAs without transfection reagent at final concentrations of 160 ug/ml before Flow cytometry was performed using FACS-Calibur.

Figure 22:
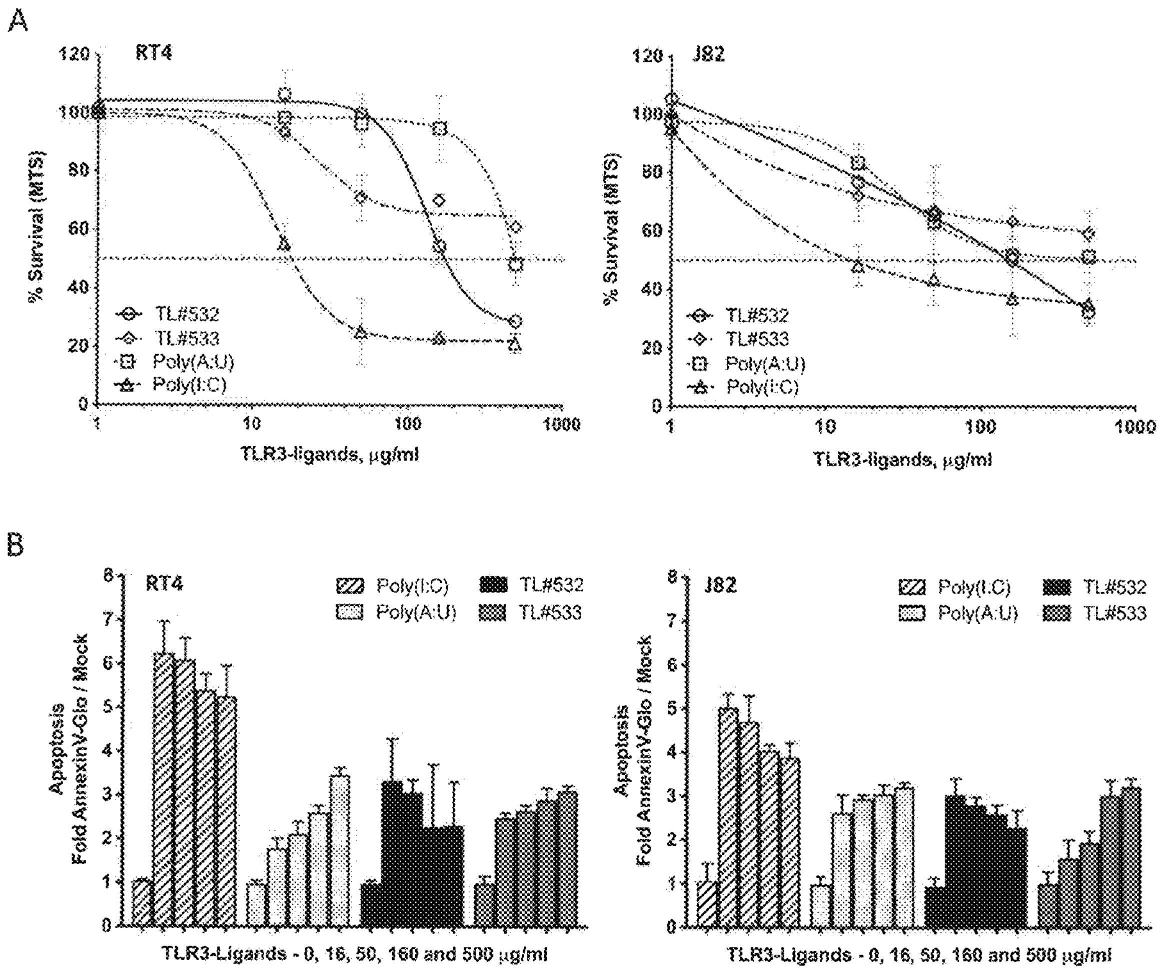

FIG. 22: TL #532 and dsRNA ID #533 (TL #533) induces bladder tumor cells death through apoptosis. RT4 (left panel) and J82 (right panel) bladder cancer cell lines from ATCC (Cat #HTB-2 and #HTB-1), were treated for 24 hours with the indicated dsRNAs, at final concentrations ranging from 16 μg/mL to 500 ug/ml. (A) Cell viability was measured 24 h post-treatment using MTS Cell Titer Aqueous solution from Promega. (B) Apoptosis was measured with AnnexinV+ luminescence read-out using the Real-Time Glo AnnexinV kit from Promega. Data are the mean of three independent experiments.

Figure 23:
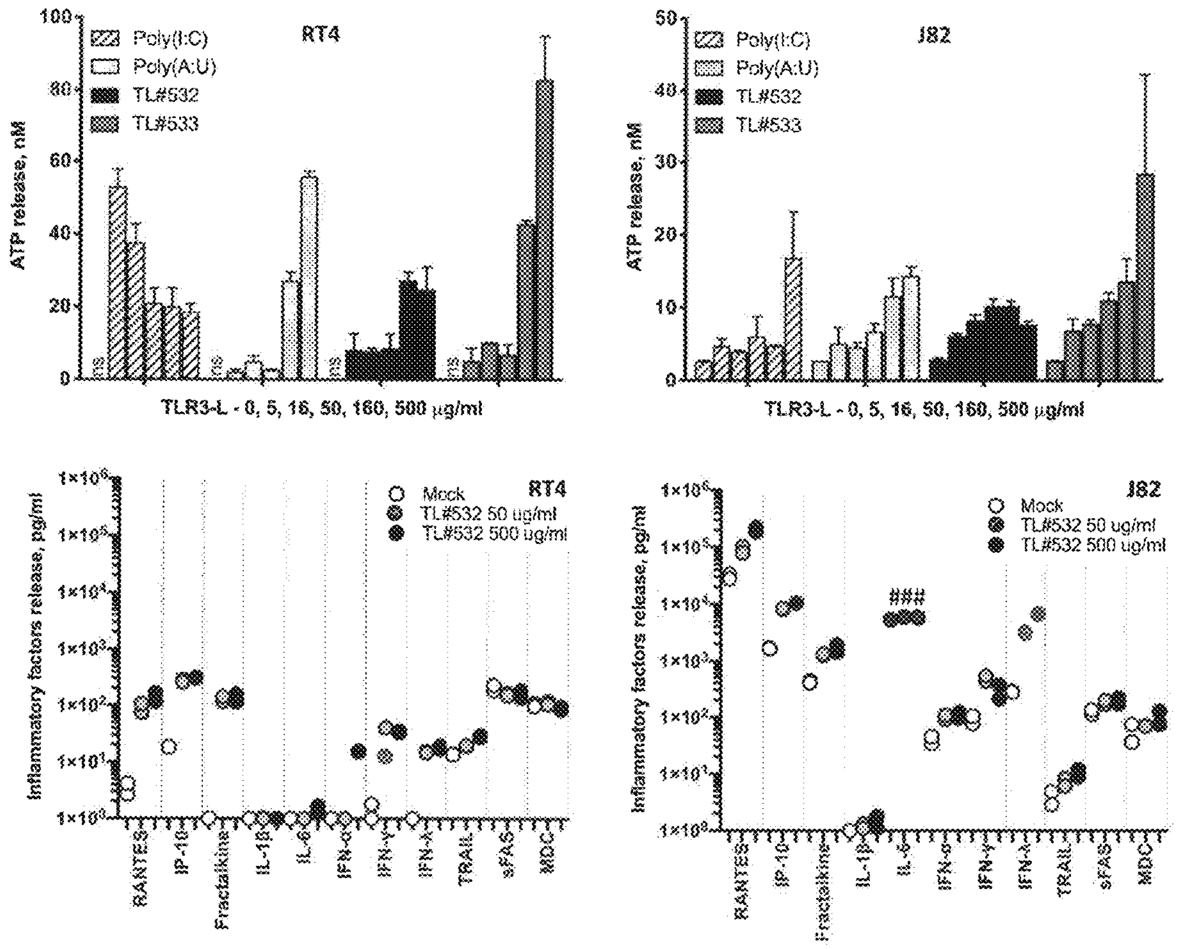

FIG. 23: TL #532 and TL #533 induces immunogenicity and inflammation. RT4 (left panel) and J82 (right panel) bladder cancer cell lines from ATCC (Cat #HTB-2 and #HTB-1) were treated for 24 hours with the indicated dsRNAs, without transfection reagent, at final concentrations ranging from 5 μg/mL to 500 ug/ml. (A) Early active ATP release was measured using CellTiter-Glo Luminescent Assay from Promega (Cat #G7570). Data are the mean of two independent experiments with Standard Deviation. (B) Supernatants of RT4 and J82 either were collected at 24 h post-treatment and submitted to Multiparametric ELISA from Mesoscale Diagnostics. Results are shown as single dot per independent experiment. Out of range values are indicated by red dots.

Figure 24:
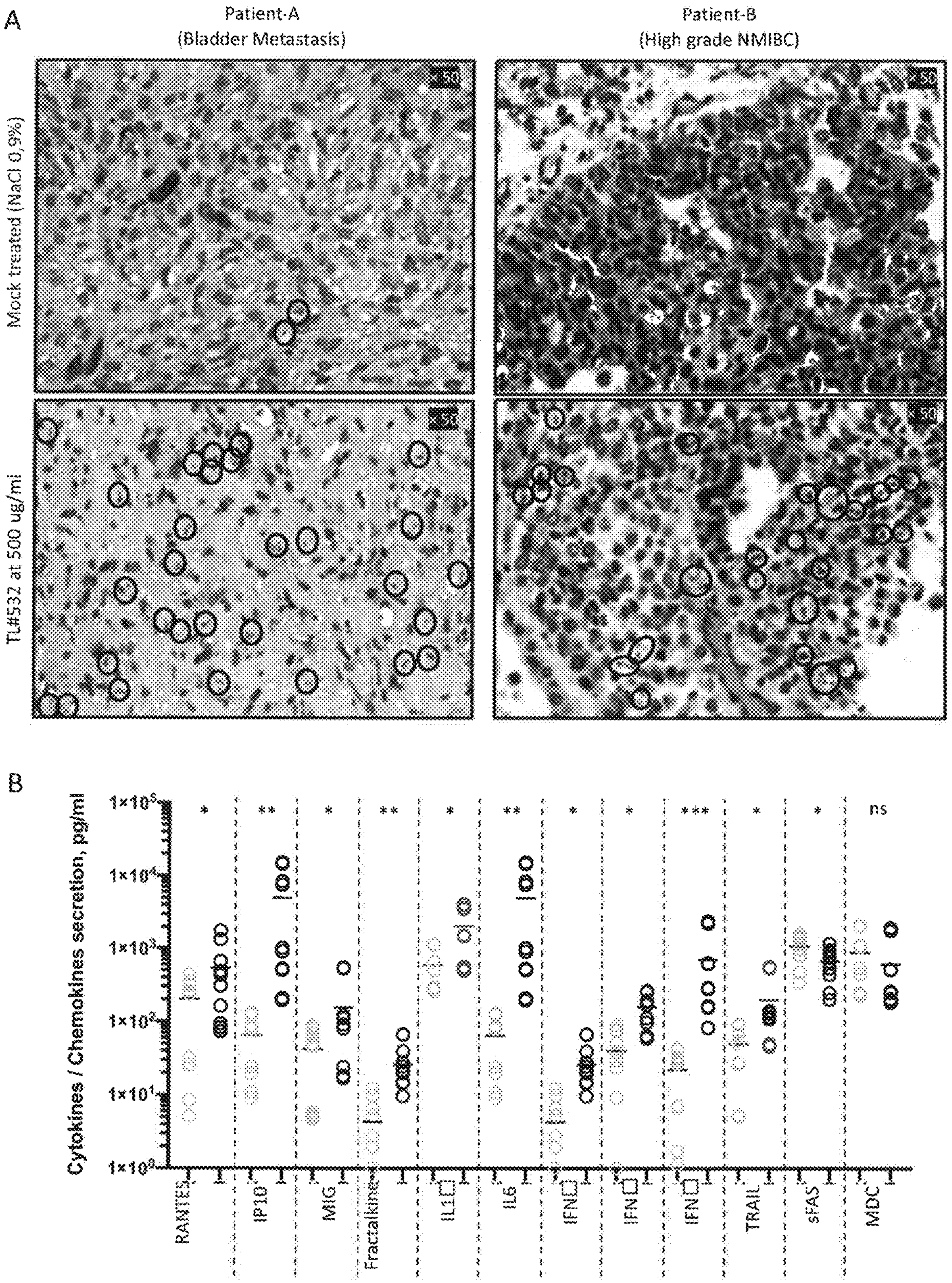

FIG. 24: Experiments on freshly resected bladder tumors treated ex-vivo demonstrates that TL #532 induces cell death through apoptosis and proinflammatory antitumor response. (A) Representative tissues sections (HPS staining) of two tumors (bladder metastasis—left panel and high grade of NMIBC—right panel) from two patients, after 24 h of treatment with either saline (mock) or TL #532 (final concentration 500 μg/ml). Cell death is demonstrated by the partial disruption of cancer tissue and the appearance of late apoptotic bodies (circled in black). (B) The supernatants of the same tumor tissues section cultures contained several inflammatory cytokines and chemokines measured with the Multiparametric Elisa MSD (Meso Scale Discovery). Mean values are presented and statistics were performed using unpaired t-test (*=$p \leq 0.05$, =$p \leq 0.01$, *=$p \leq 0.001$).

Figure 25:
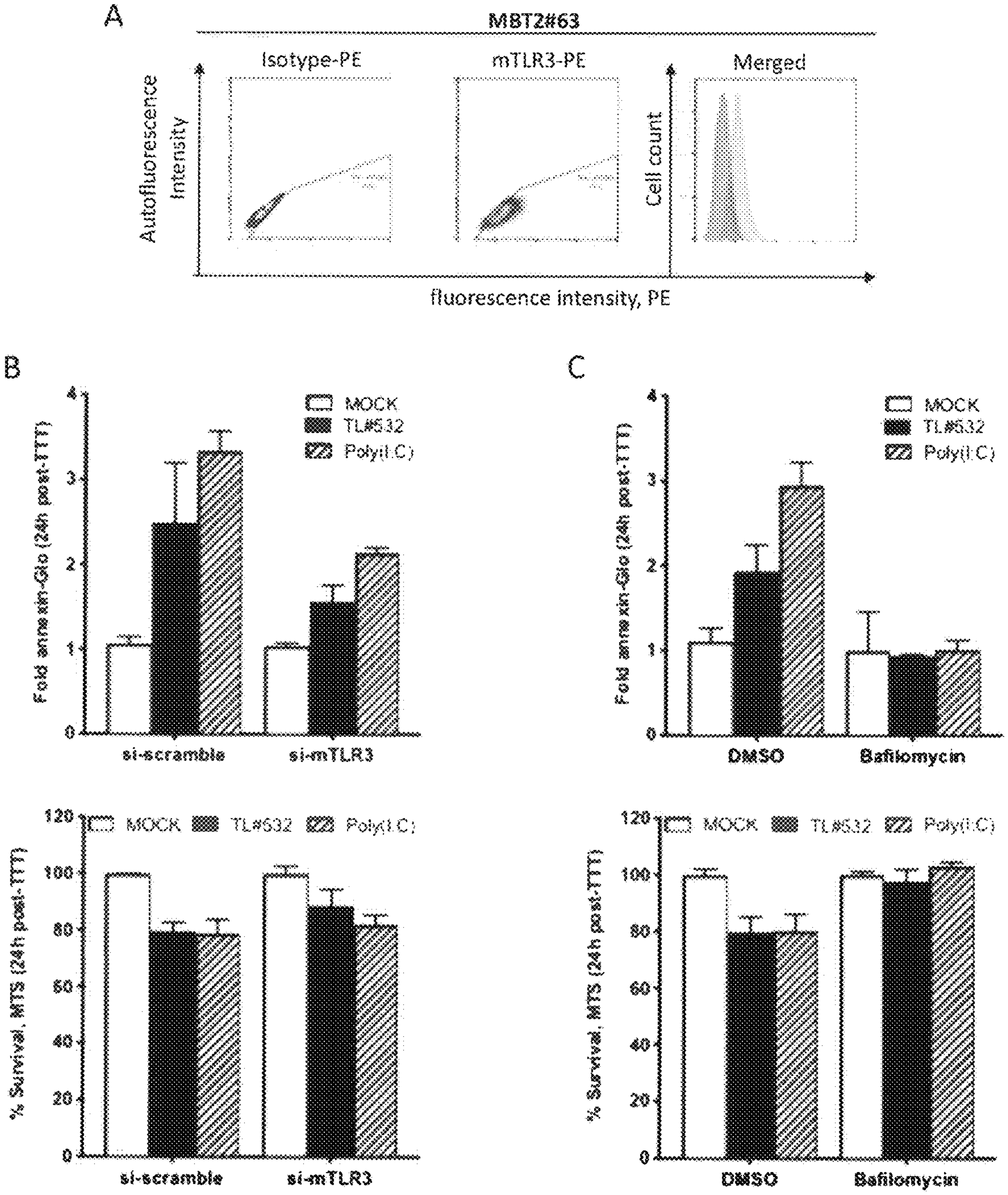

FIG. 25: TLR3-Ligands induces cell death through apoptosis, is specific of TLR3 activation, in murine syngeneic cell line MTB2 #63. (A) MBT2 #63 murine cell line model express murine TLR3. MBT2 cells were fixed and permeabilized before flow cytometry was performed. Results are shown for 10.000 cells per treatment as dot plot of autofluorescence versus FITC-fluorescence intensity and a merged histogram where isotype and mTL3 are represented in dark-grey and light-grey respectively. (B) TLR3 cell death specificity was monitored by pretreating MBT2 cells with small interferent RNA for TLR3 expression. The transfection of si-scramble or si-mTLR3 of MBT2 cells was performed before treatment using the indicated dsRNAs without transfection reagent, at 250 ug/ml. (C) Acidic endolysosomal conditions are detrimental for TLR3 activation. MBT2 cells were pretreated with Bafilomycin-A1 before MBT2 cells were treated with the indicated dsRNAs, without transfection reagent, at the final concentrations of 250 ug/ml. (B and C upper panel) Apoptosis was measured with AnnexinV+ luminescence read-out using the Real-Time Glo AnnexinV kit from Promega. (B and C Lower panel) Cell viability was measured 24 h post-treatment using MTS Cell Titer Aqueous solution from Promega. Data are the mean of two independent experiments with SD.

Figure 26:
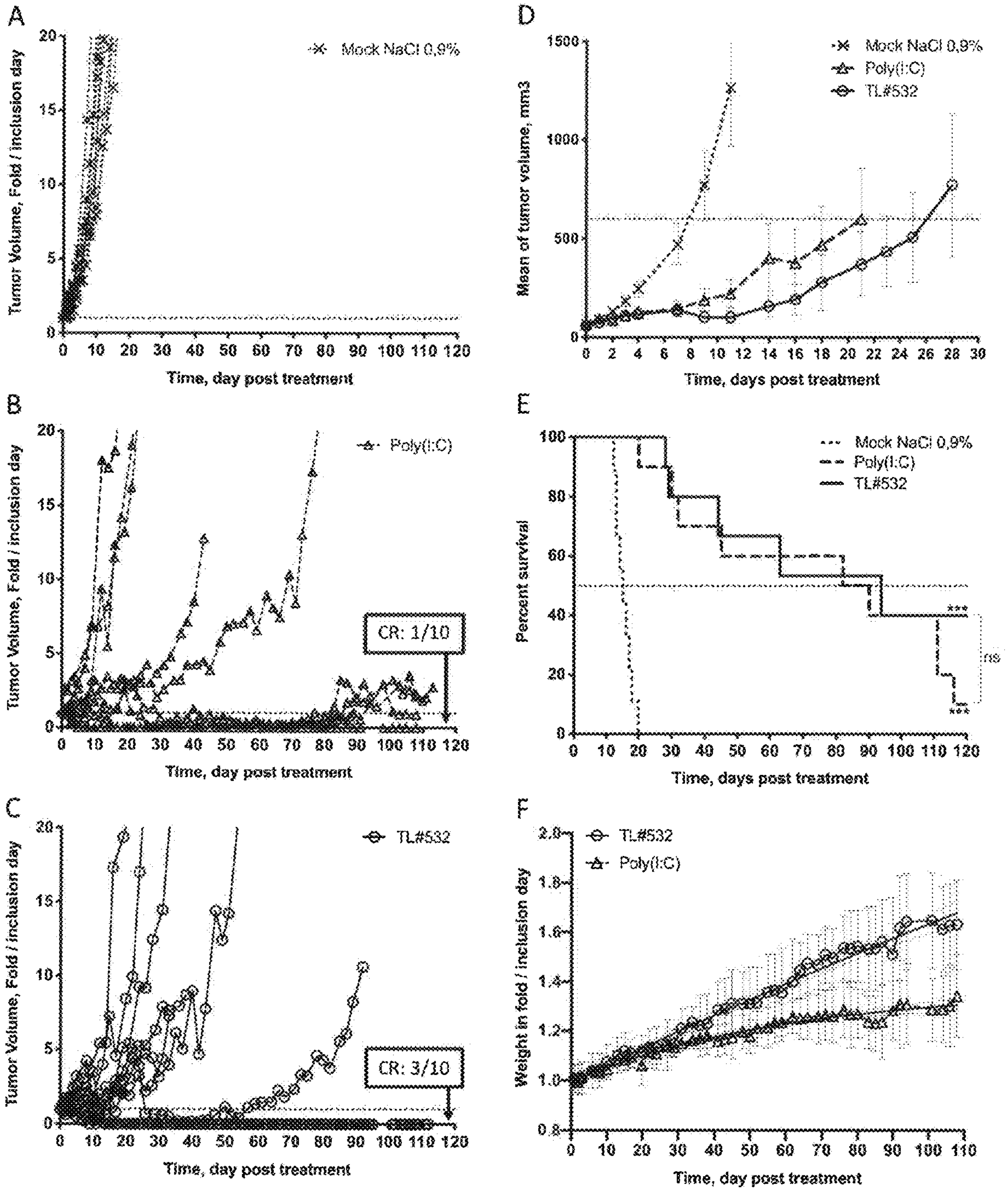

FIG. 26: TL #532 induces equal or better anti tumoral effect than Poly(I:C) on syngeneic bladder cancer model MBT2 in vivo, with a better tolerance for the TL #532 treatment. Mouse model C3H/HeN from Charles River, is an immunocompetent species from which MBT-2 #63 bladder cancer model is derived. 6 weeks old female mice were used to perform subcutaneous grafts of 1,000,000 MBT-2 #63 cells on the right flank. The first day of treatment is designated as day zero (d0). Tumor inclusion window was between 75 and 125 mm3. In order to best mimic the route of clinical administration, one half is injected via the intratumoral route and the remainder via the subcutaneous peritumoral route. Three groups of ten mice were treated either with Poly(I:C) or TL #532, without transfection reagent, at final dose of 200 and 500 ug respectively. Treatments were administered 3 times per week, up to the end point or the total regression of the tumor or the end of treatment at three months. The weight of the animals and tumor volumes were monitored three times a week. Tumor growth of the mock-treated (A), or treated with either Poly(I:C) (B) or TL #532 (C) groups, are shown. We observed 1/10 mice and 3/10 complete responder mice in Poly(I:C) and TL #532 treated groups respectively. (D) Effect of TL #532 is confirmed by the tumor growth delay (TGD). TGD of the Poly(I:C) group is extended by 13 days (×2,6) and the TGD TL #532 by 18 days (×3,25), as compared to Mock-treated group. (E) A significant improvement is observed in the survival of the mice when they are treated with TLR3-ligands. (F) TL #532 is better tolerated compared with Poly(I:C) as shown by the weight curve. CR: mice in complete responders/total treated. Kaplan Meier results were analyzed using Mann-Whitney U test and Log rank statistical methods. Tumor growth monitoring was analyzed using an unpaired t-test with p value 0.05 considered as significant.

Figure 27:
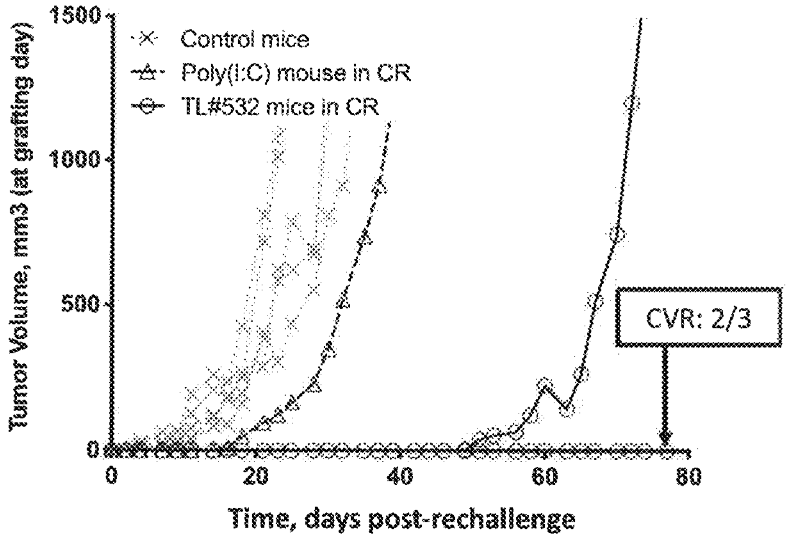

FIG. 27: TL #532 induces vaccinal effect for all the three complete responders when rechallenged on the opposite flank 3 months after remission. All the complete responders shown in FIG. 26 (1 from Poly(I:C) group and 3 from TL #532 group) were rechallenged on the opposite flank three months after their remission, using the same protocol. The TGD of the rechallenged mice treated with TL #532 is greater than the rechallenged mouse treated with Poly (I:C), with two TL #532 rechallenged mice displaying a complete vaccine response effect.

Figure 28:
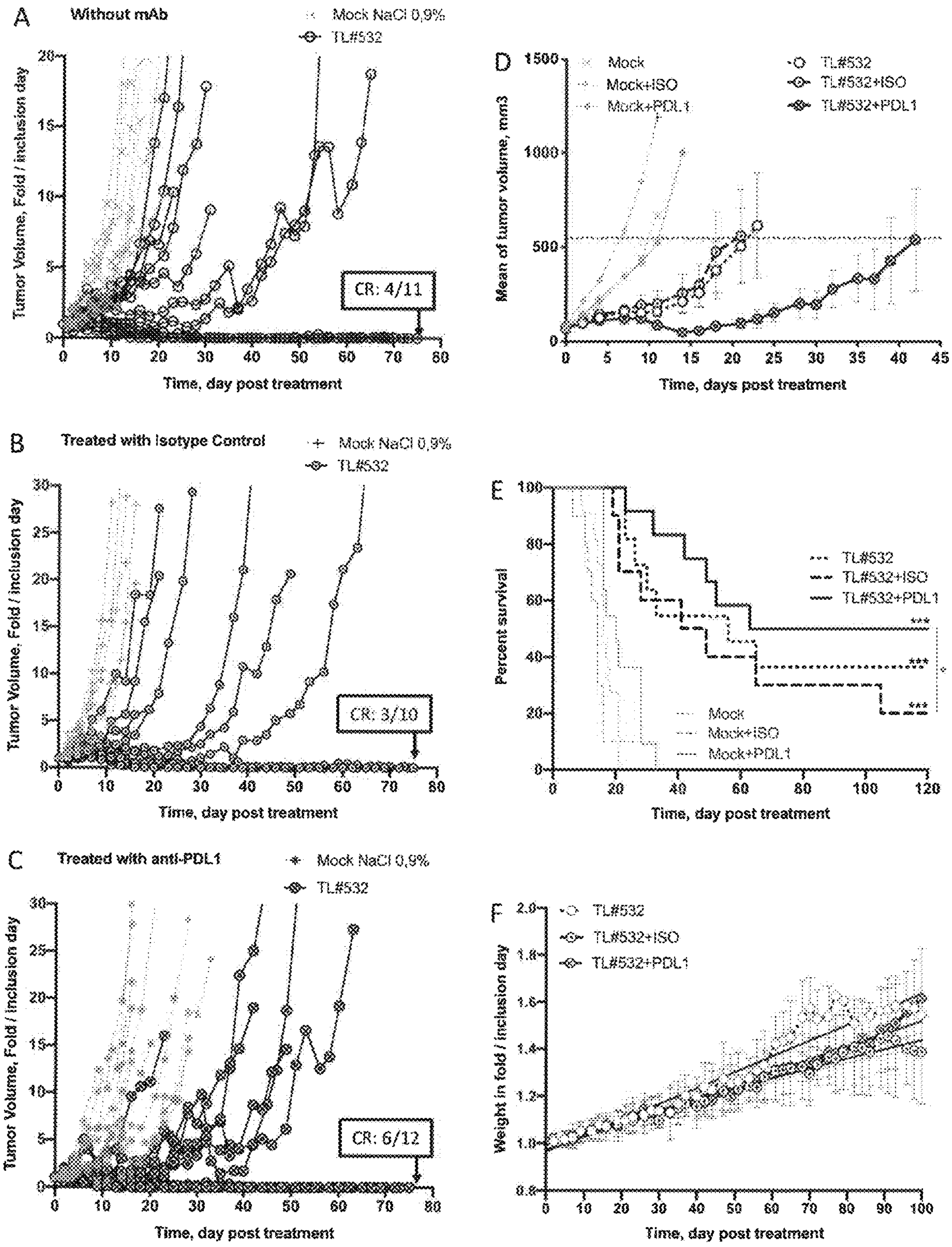

FIG. 28: TL #532 induces better anti tumoral effects than Immune-checkpoint inhibitor anti-PDL1 and their combo-therapy induces synergistic effects in vivo.

MBT2/C3H/HeN syngeneic model was used and grafted as described in FIG. 27. Mice were included when they developed a homogeneous spheroid tumour measuring between 75 and 125 mm3. 6 groups were sub-divided: group I was Mock-NaCl without monoclonal antibodies (mAb) treatment, group II was (Mock-NaCl+Isotype-control mAb), group III was (Mock-NaCl+Anti-PDL1 mAb), group IV was TL #532 group, group V was (TL #532+Isotype-control mAb) and the group VI was (TL #532+Anti-PDL1 mAb). A treatment, for a maximum period of 3 months, was chosen for this "proof of concept" experimentation. Tumor growth for mock-treated mice versus TL #532 treated mice are shown either without mAb combination treatments (A), in combination with isotype control mAb (B) or with anti-PDL1 mAb (C). Among all of the groups, only the TL #532 treated groups were able to reach complete responses, with a more pronounced complete response rate in the group VI where the combination is tested. The growth curves (A, B and C) and the TGD curves (D), demonstrate a strong synergy when anti-PDL1 is combined with TL #532. (E) Kaplan Meier curves show a very significant increase in survival in the groups treated with TL #532 as compared to the control groups and a slight improvement in survival in the "TL #532+anti-PDL1 combo". (F) Evolution of the weights of the mice in the groups IV, V and VI. The weights of the mice remain homogeneous and comparable between the three groups. Kaplan Meier results were analyzed using Mann-Whitney U test and Log rank statistical methods. Tumor growth monitoring was analyzed using an unpaired t-test with p value 0.05 considered as significant. CR: mice in complete responders versus total treated.

EXAMPLES

Abreviations

TLR3: Toll-like Receptor 3 (CD283)
WT: Wild Type
KO: Knock Out
TBE: Tris Borate EDTA
APS: Ammonium Persulfate
TEMED: Tetramethylethylenediamine
BET: Bromure Ethidium
DNA: Desoxyribonucleic Acid
RNA: Ribonucleic Acid
dsRNA: double stranded RNA
ssRNA: double stranded RNA
Poly(A:U): PolyAdenylic PolyUridylic acid
PAU: high molecular weight commercial Poly(A:U)
Poly(I:C): Polylnosinic PolyCytidylic acid
PIC: Poly(I:C)
bp: base pair
mTNFa: mouse Tumor Necrosis Factor alpha
hIL6: human Interleukin-6
Å: Angstrom
5'ppp: 5' tri-phosphate
ISRE: Interferon Stimulated Response Element

TABLE 1

| dsRNA ID# | Sequence 5'→3' | | SEQ ID NO: |
|---|---|---|---|
| 1 | Sense | UACIUCAUAUAIIIACCUAUIUUAUCUICIUIUCCAACCUUAIIAUUCAC | 1 |
| | Antisense | IUIAAUCCUAAIIUUIIACACICAIAUAACAUAIIUCCCUAUAUIACIUA | 2 |
| 3 | Sense | UCIIUCIACICAAICIAUUACACUCCUIUCACAUCAUAAUCIUUUICUAU | 3 |
| | Antisense | AUAICAAACIAUUAUIAUIUIACAIIAIUIUAAUCICUUICIUCIACCIA | 4 |
| 4 | Sense | AAUIAAIUAUUIICAIACAUUIAIUICCIAACAAIACCUIACCUAACIIU | 5 |
| | Antisense | ACCIUUAIIUCAIIUCUUIUUCIICACUCAAUIUCUICCAAUACUUCAUU | 6 |
| 5 | Sense | CICUIUUUUCIAAAUUACCCUUUAUICICIIIUAUUIAACCACICUUAUI | 7 |
| | Antisense | CAUAAICIUIIUUCAAUACCCICICAUAAAIIIUAAUUUCIAAAACAICI | 8 |
| 6 | Sense | IIAAIUIUIICUAIAUCUUAICUUACIUCACUAIAIIIUCCACIUUUAIU | 9 |
| | Antisense | ACUAAACIUIIACCCUCUAIUIACIUAAICUAAIAUCUAICCACACUUCC | 10 |
| 9 | Sense | AAIAIAIUCUCAUAAUACIUCCIICCICAUICICAIIIUAUAUUUIIACA | 11 |
| | Antisense | UIUCCAAAUAUACCCUICICAUICIICCIIACIUAUUAUIAIACUCUCUU | 12 |
| 10 | Sense | AUAIAAACUACAIIACUAACCUUCCUIICAACCIIIAIIUIIIAAUCCIU | 13 |
| | Antisense | ACIIAUUCCCACCUCCCIIUUICCAIIAAIIUUAIUCCUIUAIUUUCUAU | 14 |
| 13 | Sense | IAIIAIIAIUCIUCAIACCAIAUAICUUUIAUIUCCUIAUCIIAAIIAUC | 15 |
| | Antisense | IAUCCUUCCIAUCAIIACAUCAAAICUAUCUIIUCUIACIACUCCUCCUC | 16 |
| 14 | Sense | IIAUACIAIAUCCIUAIAUUIAUAAIIIACACIIAAUAUCCCCIIACICA | 17 |
| | Antisense | UICIUCCIIIIAUAUUCCIUIUCCCUUAUCAAUCUACIIAUCUCIUAUCC | 18 |
| 16 | Sense | ACIUUCUAAIAIUUIIACIAAAUIUUUCICIACCUAIIAUIAIIUCICCC | 19 |
| | Antisense | IIICIACCUCAUCCUAIIUCICIAAACAUUUCIUCCAACUCUUAIAACIU | 20 |
| 17 | Sense | UACIUAICAAIIUIACACAAICACAIUAIAUCCUICCCICIUUUCCUAUI | 21 |
| | Antisense | CAUAIIAAACICIIICAIIAUCUACUIUICUUIUIUCACCUUICUACIUA | 22 |
| 18 | Sense | CUAIUUIUIIAUUIIAUUICCAUUCUCCIAIUIUAUUACCIUIACIICCI | 23 |
| | Antisense | CIICCIUCACIIUAAUACACUCIIAIAAUIICAAUCCAAUCCACAACUAI | 24 |

TABLE 1 -continued

| dsRNA ID# | Sequence 5'→3' | | SEQ ID NO: |
|---|---|---|---|
| 19 | Sense | CACIIIUCCCAUIUAAUICAIUCIUAICCUACCUIACUIUACUUIIAAIU | 25 |
| | Antisense | ACUUCCAAIUACAIUCAIIUAIICUACIACUICAUUACAUIIIACCCIUI | 26 |
| 20 | Sense | IACCIIACIAACCACAIAICICUIIAAIAAUCUCUAICUICUUUACAAAI | 27 |
| | Antisense | CUUUIUAAAICAICUAIAIAUUCUUCCAICICUCUIUIIUUCIUCCIIUC | 28 |
| 21 | Sense | UUUCCCACUICCUUAAICCIICUUICCCUUUCUICCUIUAIAUCCAUUII | 29 |
| | Antisense | CCAAUIIAUCUACAIICAIAAAIIICAAICCIICUUAAIICAIUIIIAAA | 30 |
| 22 | Sense | ICAACUUCIAIIACCUAAUIUIACCIACCUAIAUUCIICAUUIUIIICAI | 31 |
| | Antisense | CUICCCACAAUICCIAAUCUAIIUCIIUCACAUUAIIUCCUCIAAIUUIC | 32 |
| 23 | Sense | IAUCUAUIICIUIAIACCCIUUAUICUCCAUUACIIUCAIUIIIUCACAI | 33 |
| | Antisense | CUIUIACCCACUIACCIUAAUIIAICAUAACIIIUCUCACICCAUAIAUC | 34 |
| 24 | Sense | ACUICIACIUUCUAAACIUUIIUCCIUCAIAAICICCAUCCAIIAUCACI | 35 |
| | Antisense | CIUIAUCCUIIAUIICICUUCUIACIIACCAACIUUUAIAACIUCICAIU | 36 |
| 25 | Sense | ACUIIUICCAACICICAIICAUAIUUCIAIIAIAAUUAUCCIIIIICAAU | 37 |
| | Antisense | AUUICCCCCIIAUAAUUCUCCUCIAACUAUICCUICICIUUIICACCAIU | 38 |
| 26 | Sense | IACAACCAICAUCUCIIIUCUUICCCAACCCIUCUACACICUIUUAUAIC | 39 |
| | Antisense | ICUAUAACAICIUIUAIACIIIUUIIICAAIACCCIAIAUICUIIUUIUC | 40 |
| 27 | Sense | CAUICUAICIUICIIIIUACACUUICUAACCAUUUIIIACACIIIACACU | 41 |
| | Antisense | AIUIUCCCIUIUCCCAAAUIIUUAICAAIUIUACCCCICACICUAICAUI | 42 |
| 28 | Sense | AUAIACIIACAICUUIIUAUCCUIAICACAIUCICICIUCCIAAUCUAIC | 43 |
| | Antisense | ICUAIAUUCIIACICICIACUIUICUCAIIAUACCAAICUIUCCIUCUAU | 44 |
| 29 | Sense | UACCCAUACUCCACCIUUIICAIIIIIAUCICAUIUCCCACIUIAAACAU | 45 |
| | Antisense | AUIUUUCACIUIIIACAUICIAUCCCCCUICCAACIIUIIAIUAUIIIUA | 46 |
| 30 | Sense | AIUACAAIACUAICCUUICUAICAACCICIIICUIIIAICCUAAIIUAUC | 47 |
| | Antisense | IAUACCUUAIICUCCCAICCCICIIUUICUAICAAIICUAIUCUUIUACU | 48 |
| 31 | Sense | UUCAICICICAIICUUIIIUCIAIAUAAAAUCUCCAIUICCCAAIACCAC | 49 |
| | Antisense | IUIIUCUUIIICACUIIAIAUUUUAUCUCIACCCAAICCUICICICUIAA | 50 |
| 32 | Sense | ICAACIIAACIUCCUUAICUCCIICAIICAAUUAAIIIIAACICAAICAU | 51 |
| | Antisense | AUICUUICIUUCCCCUUAAUUICCUICCIIAICUAAIIACIUUCCIUUIC | 52 |
| 33 | Sense | IUAUCAUUIUICACCUICCIIUIACCACUCAACIAUIUIIIIACICCIUU | 53 |
| | Antisense | AACIICIUCCCCACAUCIUUIAIUIIUCACCIICAIIUICACAAUIAUAC | 54 |
| 34 | Sense | IUUACCCAUAUIIUCCACAIIACACUCIUCICUUCCIIICUUICCCUCUA | 55 |
| | Antisense | UAIAIIICAAICCCIIAAICIACIAIUIUCCUIUIIACCAUAUIIIUAAC | 56 |
| 36 | Sense | ACICUIUCUCUIICACIUIIIUIICCUAIAIIAAUCACAUCCAAICCUII | 57 |
| | Antisense | CCAIICUUIIAUIUIAUUCCUCUAIICCACCCACIUICCAIAIACAICIU | 58 |
| 37 | Sense | IUCIUIICAAUIUUCIUCUIIIUIUIIUCUACACAAUICIIICIIUICIU | 59 |
| | Antisense | ACICACCICCCICAUUIUIUAIACCACACCCAIACIAACAUUICCACIAC | 60 |
| 38 | Sense | UIICAIACACACCIUIACCCCICCUCUCCAUUIAUICCACIICIAAUIUC | 61 |
| | Antisense | IACAUUCICCIUIICAUCAAUIIAIAIICIIIIUCACIIUIUIUCUICCA | 62 |
| 40 | Sense | AICCCUUCUCCCCUICIICCACICCCIUAIAIAUCACICCUUUIACCCUC | 63 |
| | Antisense | IAIIIUCAAAIICIUIAUCUCUACIIICIUIICCICAIIIIAIAAIIICU | 64 |
| 41 | Sense | ACICUICAIIACUUICAACCIIICAIACUCIICIICAIIUCCUAIUICAI | 65 |
| | Antisense | CUICACUAIIACCUICCICCIAIUCUICCCIIUUICAAIUCCUICAICIU | 66 |
| 42 | Sense | IICIAAIICCCUAACIIIAIAUACICICCCACAACUCIICICIAAUACII | 67 |
| | Antisense | CCIUAUUCICICCIAIUUIUIIICICIUAUCUCCCIUUAIIICCUUCICC | 68 |
| 44 | Sense | ICACCAIAUCUIUAAIIUCCICCACICAIACIAIICCIIICIIAIACCAC | 69 |
| | Antisense | IUIIUCUCCICCCIICCUCIUCUICIUIICIIACCUUACAIAUCUIIUIC | 70 |
| 45 | Sense | UCCUIIAIIAIIIICIIAUAICCUCUUACCCIUICCCCACCIUUIICIIU | 71 |
| | Antisense | ACCICCAACIIUIIIICACIIIUAAIAIICUAUCCICCCCUCCUCCAIIA | 72 |
| 47 | Sense | UICICCIIUCCCCAICCICICUCAUICUCIICACCICCAUAACCAIACCI | 73 |
| | Antisense | CIIUCUIIUUAUIICIIUICCIAICAUIAICICIICUIIIIACCIICICA | 74 |

TABLE 1 -continued

| dsRNA ID# | Sequence 5'→3' | | SEQ ID NO: |
|---|---|---|---|
| 48 | Sense | UAICCICCCCUIIICCICIIUCCICUACCUUICAIIAAUCIAIICCIUCC | 75 |
| | Antisense | IIACIICCUCIAUUCCUICAAIIUAICIIACCICIICCCAIIIICIICUA | 76 |
| 345 | Sense | ICUICUUCIICICCCCIIICICACCCCUICCICIIIIICIIIAUCICCCI | 77 |
| | Antisense | CIIICIAUCCCICCCCCICIICAIIIIUICICCCIIIICICCIAAICAIC | 78 |
| 397 | Sense | IUCIICICCCIICCCCCCIICCCCICAICIIICUCCCCICCCIIICCICC | 79 |
| | Antisense | IICIICCCIIICIIIIAICCCICUICIIIICCIIIIIICCIIICICCIAC | 80 |
| 398 | Sense | IIIIIICCCACICIICIICICCICCIICICCCCCIIIICICCCCICIUCI | 81 |
| | Antisense | CIACICIIIICICCCCIIIIICICCIICIICICCICCICIUIIICCCCCC | 82 |
| 415 | Sense | CIIICCIICIIIIIICIIICIIIIICCCCUIICCCICCCIICICCCCICI | 83 |
| | Antisense | CICIIIICICCIIICIIICCAIIIICCCCCICCCICCCCCCICCIICCCI | 84 |
| 418 | Sense | IIICCIIIICIICCCCIIICIICIICCICCIICCCCIICIICIIIICICC | 85 |
| | Antisense | IICICCCCICCICCIIIICCIICIICCICCICCCIIIICCICCCCIICCC | 86 |
| 405 | Sense | IIAUAIIIICIICCCCIIICIICIICCICCIICCCCIICIICIIIICIUU | 87 |
| | Antisense | AACICCCCICCICCIIIICCIICIICCICCICCCIIIICCICCCCUAUCC | 88 |
| 413 | Sense | AUUUAAAAAAUAAAUAUAAUAAAAUAUAAUUUAAUUAAUUAUUUAUUAAU | 89 |
| | Antisense | AUUAAUAAAUAAUUAAUUAAAUUAUAUUUUAUUAUAUUUAUUUUUUAAAU | 90 |
| 411 | Sense | IIIIIIIIIIIIIIIIIIIIIIIIIIIIIIIIIIIIIIIIIIIIIIIIII | 91 |
| | Antisense | CCCCCCCCCCCCCCCCCCCCCCCCCCCCCCCCCCCCCCCCCCCCCCCCCC | 92 |
| 412 | Sense | AAAAAAAAAAAAAAAAAAAAAAAAAAAAAAAAAAAAAAAAAAAAAAAAAA | 93 |
| | Antisense | UUUUUUUUUUUUUUUUUUUUUUUUUUUUUUUUUUUUUUUUUUUUUUUUUU | 94 |

TABLE 2

Sequences of the Poly(A:U) dsRNAs ranging from 60 to 90 pb (dsRNA ID 422, 432, 442, 452), and sequences of the dsRNA 70 pb family with increasing amount of Poly(Inosinic acid:Cytidylic acid) (dsRNAs ID #532, 533, 534, 535) with respect to the dsRNA ID #432 sequence and tested for their capacity to activate the inflammatory response in the mouse macrophages RAW264.7 cells, and apoptosis with inflammatory response in the human lung cancer NCI-H292 cell.

| dsRNA ID# | |
|---|---|
| 422 | Sense 60 bases A (SEQ ID NO: 103) |
| | Antisense 60 bases U (SEQ ID NO: 104) |
| 432 | Sense 70 bases A (SEQ ID NO: 105) |
| | Antisense 70 bases U (SEQ ID NO: 106) |
| 442 | Sense 80 bases A (SEQ ID NO: 107) |
| | Antisense 80 bases U (SEQ ID NO: 108) |
| 452 | Sense 90 bases A (SEQ ID NO: 109) |
| | Antisense 90 bases U (SEQ ID NO: 110) |
| 532 | Sense 70 bases : 10 I - 50 A - 10 I (SEQ ID NO: 111) |
| | Antisense 70 bases: 10 C - 50 U - 10 C (SEQ ID NO: 112) |
| 533 | Sense 70 bases : 35 A-35 I (SEQ ID NO: 113) |
| | Antisense 70 bases : 35 U - 35 C (SEQ ID NO: 114) |
| 534 | Sense 70 bases: 10 A-50 I - 10 A (SEQ ID NO: 115) |
| | Antisense 70 bases: 10 U - 50 C - 10 U (SEQ ID NO: 116) |
| 535 | Sense 70 bases I (SEQ ID NO: 117) |
| | Antisense 70 bases C (SEQ ID NO: 118) |

The following other strands and their complementary strands may be synthesized the same way and then hybridized:

5' (I)10-(U)50-(I)10 3' (SEQ ID NO: 95)
5' (A)60-(I)10 3'(SEQ ID NO: 119)
5' (A)50-(I)20 3'(SEQ ID NO: 120)
5' (A)20-(I)50 3'(SEQ ID NO: 121)
5' (A)10-(I)60 3'(SEQ ID NO: 122)
5' (I)5-(A)60-(I)5 3'(SEQ ID NO: 96)
5' (I)15-(A)40-(I)15 3'(SEQ ID NO: 97)
5' (I)20-(A)30-(I)20 3'(SEQ ID NO: 98)
5' (I)25-(A)20-(I)25 3'(SEQ ID NO: 99)
5' (I)30-(A)10-(I)30 3'(SEQ ID NO: 123)
5' (I)5-(A)50-(I)15 3'(SEQ ID NO: 100)
5' (I)13-(A)64-(I)13 3'(SEQ ID NO: 101)
5' (I)10-(A)70-(I)10 3'(SEQ ID NO: 102)

Example 1 and FIG. 1: Analysis of 50 bp dsRNAs and Commercial Poly(A:U) on Native 8% Acrylamide Gel (TBE 1×)

Lyophilized dsRNAs obtained from DHARMACON™ (Colorado, USA) were resuspended in sterile RNAse-free physiological water (INVIVOGEN, France) according to the manufacturer protocol. After addition of nucleic acid loading buffer (Invitrogen, Cat #AM8556), 5 µg of dsRNAs was loaded in a 8% acrylamide gel prepared as follow: 9.3 mL of sterile RNAse-free water (Sigma-Aldrich where, catalogue #W4502), 1.5 mL of TBE 10× (Sigma-Aldrich), 4 mL acrylamide-bis 30% (Merck Chemicals, Germany, Cat #1.00639.1000), 0.2 mL APS (Sigma-Aldrich), 20 µL TEMED (Sigma-Aldrich). RNA ladder was obtained from Invitrogen (cat #SM1833). Samples migration was set at 100V for 1 h before BET (Sigma-Aldrich) staining at 1 µg/mL. Gel was then visualized using the GelDoc XR+ analyzer (BIORAD, California, USA). Data are representative of 9 out of 17 50 bp dsRNA.

Example 2 and FIG. 2: Secretion of TNF-Alpha by Mouse Macrophages RAW264.7 Cells in Response to 50 bp dsRNA Alone Lyophilized dsRNAs were obtained from IDT or DHARMACON. $5 \cdot 10^4$ RAW264.7 cells were seeded in a final volume of 200 µL in 96-wells plates (CORNING, USA, Cat #353072). 24 hours later, cells were treated with dsRNA without transfection reagent at a final concentration of 10

μg/mL for 24 hours and supernatants were harvested to measure mouse TNF-alpha secretion by ELISA (BioLegend, USA Cat #430903). PAU=high molecular weight commercial Poly(A:U). Data are representative of two independent assays using two different batches of the 50 bp dsRNA ID #412.

Example 3 and FIG. 3: Secretion of IL6 by Human Non-Small Cell Lung Cancer Cells NCI-H292 after Treatment with PAU or with 50 bp dsRNAs Alone $3\cdot10^3$ NCI-H292 WT or TLR3 KO cells were seeded in a final volume of 300 μL/well of p48-well plates (CORNING, USA, Cat #353078). 24 hours later, culture medium was replaced with fresh one and cells treated with dsRNAs without transfection reagent at a final concentration of 10 μg/mL. 24 h later, supernatants were harvested to measure human IL-6 secretion by ELISA (BioLegend, USA Cat #430501). PAU=high molecular weight commercial Poly(A:U). Data are representative of three independent assays.

Example 4 and FIG. 4: 50 Bp dsRNA ID #412 does not Trigger Death in Human Non-Small Cell Lung Cancer Cells NCI-H292

$1\cdot10^4$ NCI-H292 WT or TLR3 KO cells were seeded in a final volume of 100 μL/well of p96-well plates (GREINER, USA, Cat #655098). 24 hours later, cells were treated with dsRNAs without transfection reagent at a final concentration of 50 μg/mL for 24 h later before apoptosis was measured with AnnexinV$^+$ luminescence read-out using the Real-Time Glo AnnexinV kit from Promega (France, Cat #JA1000). PAU=high molecular weight commercial Poly(A:U). Data are representative of three independent assays using two different batches of the 50 bp dsRNA ID #412.

Example 5 and FIG. 5: Analysis of dsRNA ID #412, 432, 452 and Poly(A:U) on a Native 6% Acrylamide Gel (TBE 1×)

Lyophilized dsRNAs obtained from DHARMACON were resuspended in sterile RNAse-free physiological water (INVIVOGEN) according to the manufacturer protocol. After addition of RNA loading buffer (Invitrogen), 1 μg of dsRNA was loaded in a 6% acrylamide gel prepared as follow: 10.3 mL of sterile RNAse-free water (Sigma-Aldrich), 1.5 mL of TBE 10× (Sigma-Aldrich), 3 mL acrylamide-bis 30% (Merck Chemicals), 0.2 mL APS (Sigma-Aldrich), 20 μL TEMED (Sigma-Aldrich). RNA ladder was purchased from Invitrogen. Samples migration was set at 100V for 1 h before BET (Sigma-Aldrich) staining at 1 μg/mL. Gel was then visualized using the Gel Doc analyzer (BIORAD).

Example 6 and FIG. 6: Secretion of TNFalpha by Mouse Macrophages RAW264.7 Cells in Response to Poly(A:U) of Increasing Size Alone $5\cdot10^4$ RAW264.7 cells were seeded in a final volume of 200 μL in 96-well plate (CORNING, USA, Cat #353072). 24 hours later, cells were treated with dsRNA without transfection reagent at a final concentration of 10 μg/mL for 24 hours and supernatants were harvested to measure mouse TNF-alpha secretion by ELISA (BioLegend). PAU=high molecular weight commercial Poly(A:U). Data are representative of three independent assays.

Example 7 and FIG. 7: Poly(A:U) of Increasing Sizes Alone Activate the ISRE-Reporter Gene in Mouse Macrophages RAW264.7

$5\cdot10^4$ RAW264.7 cells (Invivogen, France, Cat #rawl-isg) were seeded in a final volume of 100 μL per well in 96-wells plates (CORNING, USA, 353072). 24 hours later, cells were treated with dsRNA without transfection reagent at a final concentration of 50 μg/mL for 24 hours before ISRE-driven bioluminescence assay using QUANTI-Luc kit (Invivogen, Cat #rep-old), according to manufacturer's protocol. PAU=high molecular weight commercial Poly(A:U). Data are representative of three independent assays.

Example 8 and FIG. 8: Poly(A:U) of Increasing Sizes Alone Trigger the TLR3-Dependant Secretion of IL6 by Human Non-Small Cell Lung Cancer Cells NCI-H292

$3\cdot10^4$ NCI-H292 WT or TLR3 KO cells were seeded in a final volume of 300 μL per well in 48-wells plates (CORNING, USA, Cat #353078). After 24 hours, culture medium was replaced with fresh one and cells treated with dsRNAs without transfection reagent at a final concentration of 10 μg/mL. 24 h later, supernatants were harvested to measure human IL-6 secretion by ELISA (BioLegend). PAU=high molecular weight commercial Poly(A:U). Data are representative of three independent assays.

Example 9 and FIG. 9: Poly(A:U) of Increasing Sizes Alone Trigger the TLR3-Dependant Death of Human Non-Small Cell Lung Cancer Cells NCI-H292

$1\cdot10^4$ NCI-H292 WT or TLR3 KO cells were seeded in a final volume of 100 μL/well of p96-well plate (CORNING, USA, Cat #655098). 24 hours later cells were treated with dsRNAs without transfection reagent at a final concentration of 50 μg/mL for 24 h before apoptosis was measured with AnnexinV+ luminescence read-out using the Real-Time Glo AnnexinV kit from Promega (France, Cat #JA1000). PAU=high molecular weight commercial Poly(A:U). Data are representative of three independent assays.

Example 10 and FIG. 10: Analysis of dsRNA ID #422, 432, 442, 532, 533, 534, 535, and Poly(A:U) on a Native 6% Acrylamide Gel (TBE 1×)

Lyophilized dsRNAs obtained from DHARMACON were resuspended in sterile RNAse-free physiological water (INVIVOGEN) according to the manufacturer protocol. After addition of RNA loading buffer (Invitrogen), 1 μg of dsRNA was loaded in a 6% acrylamide gel prepared as follow: 10.3 mL of sterile RNAse-free water (Sigma-Aldrich), 1.5 mL of TBE 10× (Sigma-Aldrich), 3 mL acrylamide-bis 30% (Merck Chemicals), 0.2 mL APS (Sigma-Aldrich), 20 μL TEMED (Sigma-Aldrich). RNA ladder was purchased from Invitrogen. Samples migration was set at 100V for 1 h before BET (Sigma-Aldrich) staining at 1 μg/mL. Gel was then visualized using the Gel Doc analyzer (BIORAD). Gel is representative of two independent assays.

Example 11 and FIG. 11: Secretion of TNFalpha by Mouse Macrophages RAW264.7 Cells in Response to Poly(A:U) and dsRNA ID #422, 432, 442, 532, 533, 534, 535

$5\cdot10^4$ RAW264.7 cells were seeded in a final volume of 200 μL per well using p96-well plate (CORNING, USA, Cat

#353072). 24 hours later, cells were treated with dsRNA without transfection reagent at a final concentration of 10 μg/mL for 24 hours and supernatants were harvested to measure mouse TNF-alpha secretion by ELISA (BioLegend). PAU=high molecular weight commercial Poly(A:U). Data are representative of two independent assays.

Example 12 and FIG. 12: Poly(A:U) of Increasing Sizes and dsRNA ID #422, 432, 442, 532, 533, 534, 535 Alone Trigger the TLR3-Dependant Secretion of IL6 by Human Non-Small Cell Lung Cancer Cells NCI-H292

$3 \cdot 10^4$ NCI-H292 WT or TLR3 KO cells were seeded in a final volume of 300 μL per well using p48-well plate (CORNING, USA, Cat #353078). 24 hours later, cells were treated with dsRNAs without transfection reagent at a final concentration of 10 μg/mL for 24 h and supernatants were harvested to measure human IL-6 secretion by ELISA (BioLegend). PAU=high molecular weight commercial Poly (A:U). Data are representative of at least two independent assays.

Example 13 and FIG. 13: Poly(A:U) of Increasing Sizes and dsRNA ID #422, 432, 442, 532, 533, 534, 535 Alone Trigger the TLR3-Dependant Apoptosis of Human Non-Small Cell Lung Cancer Cells NCI-H292

$1 \cdot 10^4$ NCI-H292 WT or TLR3 KO cells were seeded in a final volume of 100 μL per well using p96-well plate (GREINER, USA, Cat #655098). 24 hours later, cells were treated with dsRNAs without transfection reagent at a final concentration of 50 μg/mL for 24 h before apoptosis was measured with AnnexinV$^+$ luminescence read-out using the Real-Time Glo AnnexinV kit from Promega (France, Cat #JA1000). PAU=high molecular weight commercial Poly (A:U). Data are representative of at least two independent assays.

Example 14 and FIG. 14: Secretion of TNF-Alpha by Mouse Macrophages RAW264.7 Cells in Response to dsRNA ID #532 Made with Two Different Chemical Manufacturing Technologies Lyophilized dsRNAs were obtained from DHARMACON using two different chemical manufacturing technologies: TBDMS or 2'ACE. $5 \cdot 10^4$ RAW264.7 cells were seeded in a final volume of 200 μL per well of p96-wells plates (CORNING, USA, Cat #353072). 24 hours later, cells were treated with dsRNA without transfection reagent at a final concentration ranging from 1 to 100 μg/mL for 24 hours and supernatants were harvested to measure mTNF-alpha secretion by ELISA (BioLegend, USA Cat #430903). Data are the mean from at least three different assays and are representative from at least six independent assays. Statistical analysis is performed using two-tailed unpaired t-student test; NS=Not Significant with $p>0.05$.

Example 15 and FIG. 15: Secretion of TNF-Alpha by Mouse Macrophages RAW264.7 Cells in Response to dsRNA ID #532 Made from Two Different Manufacturers Companies Lyophilized dsRNAs were obtained either from DHARMACON or from BIOSPRING. $5 \cdot 10^4$ RAW264.7 cells were seeded in a final volume of 200 μL per well of p96-wells plates (CORNING, USA, Cat #353072). 24 hours later, cells were treated with dsRNA without transfection reagent at a final concentration ranging from 1 to 100 μg/mL for 24 hours and supernatants were harvested to measure mTNF-alpha secretion by ELISA (BioLegend, USA Cat #430903). Data are the mean from at least five different experiments. Statistical analysis is performed using two-tailed unpaired t-student test; NS=Not Significant with $p>0.05$.

Example 16 and FIG. 16: dsRNA ID #532 from Different Chemical Manufacturing Synthesis and from Different Manufacturers Companies Trigger the Same Apoptosis Level of Human Non-Small Cell Lung Cancer Cells NCI-H292

Lyophilized dsRNAs were obtained from DHARMACON using two different chemical manufacturing technologies: TBDMS or 2'ACE; in addition, lyophilized dsRNAs were obtained from BIOSPRING. $1 \cdot 10^4$ NCI-H292 WT cells were seeded in a final volume of 100 μL per well using p96-well plate (GREINER, USA, Cat #655098). 24 hours later, cells were treated with dsRNAs without transfection reagent at a final concentration ranging from 1 to 100 μg/mL for 24 h before apoptosis was measured with AnnexinV+ luminescence read-out using the Real-Time Glo AnnexinV kit from Promega (France, Cat #JA1000). Data are representative of at least four independent assays.

Example 17 and FIG. 17: dsRNA ID #532 from Different Chemical Manufacturing Synthesis Trigger the Same Cell Viability Reduction Level of Human Non-Small Cell Lung Cancer Cells NCI-H292

Lyophilized dsRNAs were obtained from DHARMACON using two different chemical manufacturing technologies: TBDMS or 2'ACE. $1 \cdot 10^4$ NCI-H292 WT cells were seeded in a final volume of 100 μL per well using p96-well plate (GREINER, USA, Cat #655098). 24 hours later, cells were treated with dsRNAs without transfection reagent at a final concentration ranging from 1 to 100 μg/mL for 24 h before cell viability was measured with Cell Titer Aqueous solution from Promega (France, Cat #G3580). Data are representative of at least four independent assays. Statistical analysis is performed using two-tailed unpaired t-student test; NS=Not Significant with $p>0.05$.

Example 18 and FIG. 18: dsRNA ID #532 from Different Manufacturers Companies Trigger the Same Cell Viability Reduction Level of Human Non-Small Cell Lung Cancer Cells NCI-H292

Lyophilized dsRNAs were obtained either from DHARMACON or from BIOSPRING. $1 \cdot 10^4$ NCI-H292 WT cells were seeded in a final volume of 100 μL per well using p96-well plate (GREINER, USA, Cat #655098). 24 hours later, cells were treated with dsRNAs without transfection reagent at a final concentration ranging from 1 to 100 μg/mL for 24 h before cell viability was measured with Cell Titer Aqueous solution from Promega (France, Cat #G3580). Data are representative of at least five independent assays.

Example 19 and FIG. 19: Analysis of Poly(A:U) and the dsRNA ID #532 Sensitivity to the RNAse I and to the RNAse III and Analysis on a Native 6% Acrylamide Gel (TBE 1×)

RNAse I is a RNAse that displays high preference for single stranded RNA over double stranded RNA independently of the sequence, while RNAse III is a RNAse that cleaves double stranded RNA into short 12-30 bases dsRNA. Lyophilized dsRNAs obtained from DHARMACON were resuspended in sterile RNAse-free physiological water (INVIVOGEN) according to the manufacturer protocol. 1 μg of dsRNA was first incubated with either 1 unit of RNAse I (ThermoFischer AMBION, Cat #AM2294) or 1 unit of RNAse III (ThermoFischer AMBION, Cat #AM2290) for 10 or 30 min at 37° C. before addition of RNA loading buffer (Invitrogen) and loading in a 6% acrylamide gel prepared as follow: 10.3 mL of sterile RNAse-free water (Sigma-Aldrich), 1·5 mL of TBE 10× (Sigma-Aldrich), 3 mL acrylamide-bis 30% (Merck Chemicals), 0.2 mL APS (Sigma-Aldrich), 20 uL TEMED (Sigma-Aldrich). RNA ladder was purchased from Invitrogen. Samples migration was set at 100V for 45 minutes before BET (Sigma-Aldrich) staining at 1 μg/mL. Gel was then visualized using the Gel Doc analyzer (BIORAD). PAU=high molecular weight commercial Poly(A:U). Data are representative from at least two independant assays.

Example 20 and FIG. 20: Analysis of RNA Melting Curve Profile Using Q-PCR Machine Analysis Lyophilized dsRNAs obtained from DHARMACON were resuspended in sterile RNAse-free physiological water (INVIVOGEN) according to the manufacturer protocol. 1 μg of dsRNA was mixed with SyBr green PCR mix (Biorad, Cat #1725270) before melting curve analysis using Q-PCR machine from Biorad (Biorad, CFX Connect). Bold line corresponds to the named dsRNA above the respective graph. PAU=high molecular weight commercial Poly(A:U). Data are representative from at least three independant assays.

TABLE 3

Effects of the lengths and base composition of dsRNAs, as defined in Tables 1 and 2, on RAW264.7 and NCI-H292 cells activation.

| Molecules | Inflammation in murine myeloid macrophage RAW264.7 cells | Human epithelial non-small cell lung cancer NCI-H292 Inflammation | Human epithelial non-small cell lung cancer NCI-H292 Apoptosis |
|---|---|---|---|
| Commercial Poly(A:U) PAU | ++ | ++ | ++ |
| dsRNA ID #411 | – | – | – |
| dsRNA ID #535 | – | ++ | ++ |
| dsRNA ID #412 | ++ | – | – |
| dsRNA ID #432 | ++ | + | + |
| dsRNA ID #532 | ++ | ++ | ++ |
| dsRNA ID #533 | ++ | ++ | ++ |
| dsRNA ID #534 | – | ++ | ++ |

Legend :
– = Negative Effect,
+ to ++ = Positive Activation

TABLE 4

Effects of the lengths and base composition of dsRNAs, as defined in Tables 1 and 2, as defined in on RAW264.7 and NCI-H292 cells activation.

| Bases composition | Molecules | Inflammation in murine myeloid macrophage RAW264.7 cells | Human epithelial non-small cell lung cancer NCI-H292 Inflammation | Human epithelial non-small cell lung cancer NCI-H292 Apoptosis |
|---|---|---|---|---|
| (A:U) > 50% | Commercial Poly(A:U) PAU | +++ | +++ | +++ |
| | dsRNA ID #413 | – | – | – |
| | dsRNA ID #412 | +++ | – | – |
| | dsRNA ID #422 | +++ | + | + |
| | dsRNA ID #432 | +++ | ++ | ++ |
| | dsRNA ID #442 | +++ | ++ | +++ |
| | dsRNA ID #452 | +++ | ++ | ++ |
| | dsRNA ID #532 | +++ | +++ | +++ |
| (A:U) = (I:C) = 50% | dsRNA ID #533 | +++ | +++ | +++ |
| (I:C) > 50% | dsRNA ID #411 | – | – | – |
| | dsRNA ID #535 | – | +++ | +++ |
| | dsRNA ID #534 | – | +++ | +++ |

Legend :
– = Negative Effect,
+ to ++ = Positive Activation

TABLE 5

Effects of the lengths and base composition of dsRNAs, as defined in Tables 1 and 2, on RAW264.7 and NCI-H292 cells activation.

| Bases composition | Molecules | Inflammation in murine myeloid macrophage RAW264.7 cells | Human epithelial non-small cell lung cancer NCI-H292 Inflammation | Human epithelial non-small cell lung cancer NCI-H292 Apoptosis |
|---|---|---|---|---|
| (A:U) > 50% | Commercial Poly(A:U) PAU | +++ | +++ | +++ |
| | dsRNA ID #413 | – | – | – |
| | dsRNA ID #412 | +++ | – | – |
| | dsRNA ID #422 | +++ | +/– | +/– |
| | dsRNA ID #432 | +++ | + | + |
| | dsRNA ID #442 | +++ | + | ++ |
| | dsRNA ID #452 | +++ | ++ | ++ |
| | dsRNA ID #532 | +++ | +++ | +++ |
| (A:U) = (I:C) = 50% | dsRNA ID #533 | +++ | +++ | +++ |
| (I:C) > 50% | dsRNA ID #411 | – | – | – |
| | dsRNA ID #535 | – | +++ | +++ |
| | dsRNA ID #534 | – | +++ | +++ |

Legend : – = Negative Effect, +/– = Border line, + to +++ = Increase Positive Activation.

Application of the Invention to Bladder Cancer and Combined Therapy with an Anti-PD-L1

Bladder cancer is ranked fifth among all cancers in humans in Europe and accounts for 3% of deaths caused by cancer. Despite the efficacy of the different immunotherapies, *Bacillus* Calmette-Guerin (BCG) treatment and immune checkpoint inhibitors, a significant proportion of patients are non-responders either related to sub-optimal reprogramming of the immunosuppressive tumour microenvironment by BCG, or to the absence of cytotoxic T lymphocytes at the tumour site during treatment with anti-PD1/PD-L1.

It is shown that the ligands of the invention enable the stimulation of Toll like receptor 3 (TLR3) that induce cancer cell-specific extrinsic apoptosis, the invasion of tumour antigen specific cytotoxic T lymphocytes and immunostimulatory reprogramming of the tumour microenvironment, thus making it possible to overcome the limitations of available immunotherapies. The preclinical efficacy of the dsRNA ID #532 ligand (TL #532) has been studied in the human bladder tumour cell lines J82 and RT4 as also the toxicity thereof on human urothelial bladder primary cells (UBPC). Its efficacy has also been assessed in freshly resected human bladder cancer (ex vivo) as well as ectopic syngeneic murine (mouse) models of bladder cancer cells (MBT-2). The in vitro results show an apoptosis induction in the bladder tumour cell lines RT4 and J82 by TL #532 with the absence of toxicity on UBPC. The ex vivo results show TLR3 (IHC) expression in all the samples (7/7) and apoptosis of bladder cancer cells triggered by TL #532 (microscopic analysis on HES staining), on 4/4 of the samples. Reprogramming the tumour microenvironment is also observed, with stimulation of the secretion of 10 pro-inflammatory cytokines (IL6, CCL5, CXCL9, CXCL10, CD253, IL 1 beta, IFN-$\alpha$2a, IFN$\gamma$, IFN lambda, CX3CL1). In the ectopic (subcutaneous) murine model of bladder cancer cells, the intra tumour injection of TL #532 leads to a very significant slowing of tumour growth in the majority of mice (tumour growth delay multiplied by approximately 2.5) and a total regression of tumours in one third of cases (10/31). In addition, all the mice that were cured with TLR3 ligand rejected MBT-2 cells reimplanted 3 months after their recovery, demonstrating that an anti-tumour autovaccination had occurred. The preclinical project provides encouraging data for TLR3 ligand development in the treatment of urothelial carcinoma.

Non-Muscle-Invasive Bladder Cancer (NMIBC) is the most commonly occuring form of urothelial tumor and accounts for 70 to 80% of cases. 60 to 70% of patients experience recurrence or recidivism in the first year and 10 to 20% progress to either the muscle-invasive stage, or to a metastatic stage. Given a high risk of recurrence or recidivism, resection of the tumour is insufficient for intermediate and high risk NMIBCs. As a consequence, several complementary treatments associated with trans urethral resection of bladder tumour (TURBT) are recommended: either intravesical chemotherapy such as epirubicin, mitomycin or even gemcitabine, or immunotherapy with BCG therapy. Currently, BCG treatment with at least one year of maintenance treatment is the most effective complementary treatment and the only one that has shown a reduction in the risk of progression on to muscle-invasive stage. However, 30% of patients, mainly patients at very high risk, do not respond to this treatment. Currently, the Association Francaise d'Urologie (AFU)/French Association of Urology, European Association of Urology (UAE) and American Urology Association (AUA) recommend the undertaking of maintenance treatment with BCG for a period of 1 year for intermediate risk NMIBCs and for a period of 3 years for high risk NMIBCs. Intra-vesical instillation of *Bacillus* Calmette-Guérin (BCG) is a prototypical immunotherapy and has been used to treat NMIBC, making it the first treatment therapy to reprogram the immune microenvironment of the bladder tumour. It induces an innate immune response for several weeks that leads to a durable anti-tumour adaptive immune response. This mechanism is mainly mediated by Toll Like Receptors (TLRs), such as TLR2, 4 and 9. However, it appears that the BCG's ability to reprogram the cancer-associated cytokine environment remains suboptimal, limiting its therapeutic activity and therefore its effectiveness. Moreover, there is significant toxicity with a rate of severe adverse events at around 10%. As a result, only 16% of patients complete the maintenance treatment.

Muscle-Invasive Bladder Cancer (M IBC): 20 to 30% of patients are initially diagnosed with a muscle-invasive bladder carcinoma (MIBC), usually treated with neoadjuvant cisplatin-based chemotherapy followed by cystectomy. Despite these intensely demanding approaches, the 5-year survival rate is about 50%. In addition, 5% of these patients are diagnosed to be at a metastatic stage with poor prognosis in spite of chemotherapy. For several decades, no major progress had been achieved in respect of bladder cancer treatment. Since 2016 however, a very promising new option, consisting of an antibody from the "immune checkpoint inhibitors" (ICI) family, has been approved by the FDA. These are monoclonal antibodies targeting the ICI, anti-PD1 and anti-PD-L1. Despite remarkable results with anti PD1/PD-L1 antibodies, the main problem lies in the low proportion of response in patients with locally advanced or metastatic disease with overall response rate of only 20 to 30% and complete response rate of approximately 10%. As in other types of cancer, failure has often been attributed to the absence of cytotoxic CD8+T cells at the tumour site, which would be required in order to kill the cancer cells and/or to the immunosuppressive environment of the tumor.

Example 21 and FIG. 21: TL #532 has No Toxicity but Induces Antitumor Inflammation and Over Expression of TLR3 within Normal Urothelial Bladder Primary Cells (UBPC)

(A) Toxicity of TLR3-Ligands on normal urothelial bladder primary cells (UBPC): UPBC from different healthy donors (Cell-Applications-INC, Cat #938-05a), were seeded at $7\cdot10^3$ cells in a final volume of 100 μL per well of synthetic BEC-GM medium (Cell-applications-INC, Cat #217-500), using p96-well plate (GREINER, USA, Cat #655098). 24 hours later, cells were treated using either Poly(A:U) from Invivogen (Cat #tlrl-pau); Poly(I:C) from Invivogen (Cat #tlrl-pic); or TL #532 from Dharmacon, without transfection reagent, at final concentrations ranging from 8 μg/mL to 2000 μg/ml. Cell viability was measured 24 h post-treatment using MTS Cell Titer Aqueous solution from Promega (France, Cat #G3580). Data are the mean of two independent experiments using UBPC from different healthy donors, each in triplicates. Statistical analysis is performed using confident intervals for $p<0.05$.

(B) TL #532 induces antitumor inflammation on normal UBPC: Supernatants of UPBC either mock treated of treated using 62 μg/ml or 500 μg/ml of TL #532 from previous experiment were collected at 24 h post-treatment and submitted to Multiparametric ELISA from Mesoscale Diagnostics, against eleven cytokines and chemokines. A threshold of 1 μg/ml was arbitrary determined. Results are shown as single dot per independent experiment on 2 different healthy donors.

(C) TL #532 induces TLR3 overexpression on normal UBPC: UPBC from healthy donors-2, were seeded at $3\cdot10^4$ cells in a final volume of 300 μL per well of synthetic BEC-GM medium, using p24-well plate (Falcon, Cat #353047). 24 hours later, cells were treated using either Poly(A:U) from Invivogen; Poly(I:C) from Invivogen; or TL #532 without transfection reagent, at final concentrations of 160 μg/ml. Cells were harvested 24 h post-treatment, fixed and permeabilized using Cytofix/Cytoperm as preconized by manufacturer (BD, Cat #554714). Cells were incubated with either TLR3·1 primary antibody mouse anti-human from Dendritics or Isotype IgG1 from R&D, at the final concentration of 5 μg/ml for 30 minutes at 4° C. Secondary antibody Goat anti-mouse-Alexa-488 from Thermofisher (Cat #A21235) was used as preconized by manufacturer. Flow cytometry was performed using FACS-Calibur (BD). Results are shown for 10.000 cells per treatment as dot plot of autofluorescence versus FITC-fluorescence intensity.

Example 22 and FIG. 22: TL #532 and TL #533 Induces Bladder Tumor Cells Death Through Apoptosis RT4 (left panel) and J82 (right panel) bladder cancer cell lines from ATCC (Cat #HTB-2 and #HTB-1), were seeded at $1\cdot10^4$ cells in a final volume of 100 μL per well of MacCoy's 5A and MEMalpha medium respectively (Gibco, Cat #26600-023, #32581-029), supplemented with 10% FBS from Dominique Dutscher (Cat #51810-500), using p96-well plate (GREINER, USA, Cat #655098). 24 hours later, cells were treated using either Poly(A:U) from Invivogen (Cat #tlrl-pau); Poly(I:C) from Invivogen (Cat #tlrl-pic); TL #532 or TL #533 from Dharmacon, without transfection reagent, at final concentrations ranging from 16 μg/mL to 500 ug/ml.

(A) Cell viability was measured 24 h post-treatment using MTS Cell Titer Aqueous solution from Promega (France, Cat #G3580).

(B) Apoptosis was measured with AnnexinV+ luminescence read-out using the Real-Time Glo AnnexinV kit from Promega (France, Cat #JA1000). Data are the mean of three independent experiments. Statistical analysis is performed using confident intervals for $p<0.05$.

Example 23 and FIG. 23: TL #532 and TL #533 Induces Immunogenicity and Inflammation RT4 (left panel) and J82 (right panel) bladder cancer cell lines from ATCC (Cat #HTB-2 and #HTB-1), were seeded at $1\cdot10^4$ cells in a final volume of 100 μL per well of MacCoy's 5A and MEMalpha medium respectively (Gibco, Cat #26600-023, #32581-029), supplemented with 10% FBS from Dominique Dutscher (Cat #51810-500), using p96-well plate (GREINER, USA, Cat #655098). 24 hours later, cells were treated using either Poly(A:U) from Invivogen (Cat #tlrl-pau); Poly(I:C) from Invivogen (Cat #tlrl-pic); TL #532 or TL #533 from Dharmacon, without transfection reagent, at final concentrations ranging from 5 μg/mL to 500 μg/ml. (A) Early active ATP release is a biomarker of immunogenicity inducing T-cells activation and promoting cross presentation with dendritic cells. ATP release was measured 3 h45 post-treatment using CellTiter-Glo Luminescent Assay from Promega (Cat #G7570). Data are the mean of two independent experiments with Standard Deviation. (B) Supernatants of RT4 and J82 either mock treated or treated using 50 μg/ml or 500 μg/ml of TL #532 from previous experiment were collected at 24 h post-treatment and submitted to Multiparametric ELISA from Mesoscale Diagnostics, against eleven cytokines and chemokines. A threshold of 1 μg/ml was arbitrary determined. Results are shown as single dot per independent experiment. Out of range values are indicated by "#" dots.

Example 24 and FIG. 24: Experiments on Freshly Resected Bladder Tumors Treated Ex-Vivo Demonstrates that TL #532 Induces Cell Death Through Apoptosis and Proinflammatory Antitumor Response Freshly resected bladder tumors were sliced in sections of 250-300 μm thickness using a vibratome (Thermo Scientific Microm HM650V). Tumors sections were then prepared and cultured in 1 ml of synthetic BEC-GM medium (Cell-applications-INC, Cat #217-500), and treated treated using either Poly(A:U) from Invivogen (Cat #tlrl-pau); Poly(I:C) from Invivogen (Cat #tlrl-pic); or TL #532 from Dharmacon, without transfection reagent, at a final concentration of 500 ug/ml for 24 hours at 37° C. and 5% $CO_2$. The tissue sections were harvested at 0 and 24 h and fixed in 4% formalin for a period of 24 hours and embedded in paraffin. Paraffin sections of 4 μm were generated for morphological (HPS) and immunohistochemical (IHC) analyses. Supernatants were harvested at 24 hours and stored at −80° C. for subsequent cytokine assays.

(A) Representative HPS sections of two different tumors (bladder metastasis—left panel and high grade of NMIBC—right panel), from different patients, either mock-treated (upper panels) or treated using 500 μg/ml of TL #532 (lower panels). TL #532 induces cell death as demonstrated by the partial disruption of cancer tissue and the appearance of late apoptotic cores (circled in black).

(B) The reprogramming of the tumour microenvironment was studied by measuring cytokines via Multiparametric Elisa MSD (Meso Scale Discovery) Kits that assay 12 soluble biomarkers (Ref MSD U-Plex and R-Plex), some pro-inflammatory such as IL6, CCL5 (RANTES), CXCL9 (MIG), CXCL10 (IP10), CD253 (TRAIL), IL 1 beta, IFNα2a, IFNγ, IFN lambda, CX3CL1 and other anti-inflammatory agents such as CCL22 (MDC) and sFas. Grey circles and black circles represents mock treated bladder cancer tissues and tissues treated with 500 ug/ml of TL #532 respectively. Mean value is represented and statistics were performed using unpaired t-test and are represented by asterisks: * means $p\leq0.05$;  means $p\leq0.001$; * means p≤0.000.1; "ns" means Not Significant.

Example 25 and FIG. 25: TLR3-Ligands Induces Cell Death Through Apoptosis, is Specific of TLR3 Activation, in Murine Syngeneic Cell Line MTB2 #63

(A) MBT2 #63 murine cell line model express murine TLR3. MBT2 cells were seeded at $1\cdot10^5$ cells in a final volume of 300 μL per well of RPMI 1640 medium from Gibco (Cat #21875-034), supplemented with 10% FBS from Dominique Dutscher (Cat #51810-500), using p24-well plate (Falcon, Cat #353047). Cells were harvested, fixed and permeabilized using Cytofix/Cytoperm as preconized by manufacturer (BD, Cat #554714). Cells were incubated with either with Rat-anti-mouse-TLR3-PE or rat-IgG2a-PE isotype (Biolegend), at the final concentration of 1·25 μg/ml for 30 minutes at 4° C. Flow cytometry was performed using FACS-Calibur (BD). Results are shown for 10.000 cells per treatment as dot plot of autofluorescence versus FITC-fluorescence intensity and a merged histogram where isotype and mTL3 are represented in dark-grey and light-grey respectively.

(B) TLR3 cell death specificity was monitored by pre-treating MBT2 cells with small interferent RNA for TLR3 expression (or its scramble control). Briefly, MBT2 cells were transfected using JetPrime transfection reagent from PolyPlus (Cat #114-07) with 30 nM of either si-mTLR3 or si-scramble from GeneCopoeia (Cat #SR421090 and #S-4001-2), according to the manufacturer protocols. The transfection was performed twice, 72 h and 24 h prior to treatment. MBT2 cells were then treated using either Poly (I:C) from Invivogen (Cat #tlrl-pic) or TL #532 from Dharmacon, without transfection reagent, at the final concentration of 250 ug/ml.

(C) Acidic endolysosomal conditions are detrimental for TLR3 activation. In order to demonstrate the specificity of the TL #532 to TLR3, we pretreated MBT2 cells 45 minutes prior to TLR3-Ligands, using 200 nM of Bafilomycin-A1, an inhibitor of vacuolar H(+)-ATPase (Sigma-Aldrich Cat #B1793), or with the same amount of DMSO. MBT2 cells were then treated using either Poly(I:C) from Invivogen (Cat #tlrl-pic) or TL #532 from Dharmacon, without transfection reagent, at the final concentrations of 250 μg/ml. (B and C upper panel) Apoptosis was measured with AnnexinV+ luminescence read-out using the Real-Time Glo AnnexinV kit from Promega (Cat #JA1000). (B and C Lower panel) Cell viability was measured 24 h post-treatment using MTS Cell Titer Aqueous solution from Promega (France, Cat #G3580). Data are the mean of two independent experiments with SD.

Example 26 and FIG. 26: TL #532 Induces Equal or Better Anti Tumoral Effect than Poly(I:C) on Syngeneic Bladder Cancer Model MBT2 In Vivo, with a Better Tolerance for the TL #532 Treatment Mouse model C3H/HeN from Charles River, is an immunocompetent species from which MBT-2 #63 bladder cancer model is derived (syngeneic model). 6 weeks old female mice (the age at which the immune system is fully mature) were used at the time of tumor graft. Ectopic grafts of the cells MBT-2 #63 were performed subcutaneously on the right flank using 1,000,000 cells in 100 μl of RPMI 1640 medium from Gibco (Cat #21875-034), without serum nor antibiotics. The first day of treatment is designated as day zero (d0). Tumour inclusion window was between 75 and 125 $mm^3$. In order to best mimic the route of clinical administration (submucosal injections and/or instillation), one half (in a volume of 10 μl) is injected via the intratumoral route and the remainder via the subcutaneous peritumoral route. Three groups of ten mice were treated either with Poly(I:C) from Invivogen (Cat #tlrl-pic), or TL #532 from Dharmacon, without transfection reagent, at final dose of 200 and 500 μg respectively, while mock treatment was performed using the same volume of molecule diluent NaCl 0.9%. Note that 200 μg is the maximal injectable dose of Poly(I:C) due to its solubility. Treatments were administered 3 times per week, up to the end point or the total regression of the tumor or the end of treatment. A treatment, for a maximum period of 3 months, was chosen for this "proof of concept" experimentation. The weight of the animals was noted at the time of inclusion and follow-up, at least three times a week. The tumor volume was assessed by means of three-dimensional caliper gauge measurements, calculated according to the spheroidal volume formula: $\pi/6\times L\times W\times H$ (L=Length, W=width, h=height). The animals were monitored for pain, signs of suffering and any signs of abnormal behavior. In accordance with animal welfare regulations, the following ethical sacrifice criteria are applicable to all the mice, regardless of their experimental status: size of tumor >1500 $mm^3$, weight loss >20%, reduced mobility, signs of pain and/or discomfort, prostration, ascites, necrosis inducing ulcer or anemia.

Tumor growth of the mock-treated (A), or treated with either Poly(I:C) (B) or TL #532 (C) groups, are shown in fold increase compared to the inclusion date with significant effect of TL #532 and Poly(I:C). In particular, we observed 1/10 mice and 3/10 mices complete responders in Poly(I:C) and TL #532 treated groups respectively.

(D) Effect of TL #532 is also confirmed by the tumor growth delay (TGD), in the treated groups as compared to the control group. TGD is objectified by the difference in the averages of the tumor volumes of the different groups when the mice therein are alive. TGD of the Poly(I:C) group is extended by 13 days (×2.6) and the TGD TL #532 by 18 days (×3.25), as compared to Mock-treated group.

(E) A significant improvement is observed in the survival of the mice when they are treated with TLR3-ligands.

(F) Eventually, it should be noted that the study of the evolution of weight gain in the mice, corresponding to the two relatively homogeneous groups of treatment with Poly (I:C) and TL #532, shows a clear disfavor for the group of Poly(I:C) as compared to the group of TL #532, meaning a better tolerance of the TL #532 compared with Poly(I:C). CR: mice in complete responders/total treated. Kaplan Meier results were analyzed using Mann-Whitney U test and Log rank statistical methods. Tumor growth monitoring was analyzed using an unpaired t-test with p value 0.05 considered as significant.

Example 27 and FIG. 27: TL #532 Induces Vaccinal Effect for all the Three Complete Responders when Rechallenged on the Opposite Flank 3 Months after Remission All the complete responders (1 from Poly(I:C) group and 3 from TL #532 group), of the previous experiment shown in FIG. 27 were rechallenged on the opposite flank three months after their remission, using the same protocol. For this experiment, five naive mice were included as a control group. No new treatment were introduced. The tumor growth was measured 3 times a week. Mouse treated with Poly (I:C) displays a very short tumor growth delay after rechallenge (about 35-40 days to reach 1500 $mm^3$) as compared to the naïve mice (around 20-30 days), showing a weak vaccine effect of this complete responder mouse treated with Poly (I:C). Similarly, we observed a tumor growth for the complete responders mouse treated with TL #532 after rechallenge. However, the TGD observed was more pronounced (D70) than that for the mouse treated with Poly(I:C), demonstrating an effect of immunity, even though the latter was not sufficient to contain the tumor growth. Finally, we observed a complete vaccine response effect (CVR) in the other two mice treated with TL #532, with no visible or palpable tumor growth.

Example 28 and FIG. 28: TL #532 Induces Better Anti Tumoral Effects than Immune-Checkpoint Inhibitor Anti-PDL1 and their Combo-Therapy Induces Synergistic Effects In Vivo MBT2/C3H/HeN syngeneic model was used and grafted as described in FIG. 27. Sixty-five mice were included when they developed a homogeneous spheroid tumour measuring between 75 and 125 mm3. The latter were divided into 6 groups: 11 mice in the control group (Mock-NaCl without monoclonal antibodies (mAb) treatment=group I), 10 mice in the group II (Mock-NaCl+Isotype-control mAb), 11 mice in the group III (Mock-NaCl+Anti-PDL1 mAb), 11 mice in the TL #532 group (group IV), 10 in the group V (TL #532+Isotype-control mAb) and 12 mice in the group VI (TL #532+Anti-PDL1 mAb). Monoclonal antibody (mAb) therapies were administered through intra-peritoneal route using 400 μg of either anti-PDL1 mAb or isotype-control mAb from BioXCell (respectively Cat #BE0101 and #LTF-2), in 200 μl of NaCl 0.9%, once a week until ethical end points are reached, or if the total regression of the tumor is achieved. TL #532 treatments were administered as described in FIG. 27. A treatment, for a maximum period of 3 months, was chosen for this "proof of concept" experimentation.

Tumor growth for mock-treated mice versus TL #532 treated mice are shown either without mAb combination treatments (A), in combination with isotype control mAb (B) or with anti-PDL1 mAb (C). Among all of the groups, only the TL #532 treated groups were able to reach complete responses. It should be noted that the "TL #532+anti-PDL1 combo" increased in a very significant manner the rate of mice in total remission (36% in "TL #532 monotherapy" and 30% in "TL #532+isotype", as opposed to 50% in "TL #532+anti-PDL1 combo").

The growth curves (A, B and C) and the TGD curves (D), demonstrate a weak anti tumoral effect in monotherapy of anti-PDL1 but a strong synergy when combined with TL #532. Despite a pro-tumor effect of the control isotype in monotherapy, the "TL #532 monotherapy" and "combo TL #532+control isotype" treatments are found to be relatively similar. As a result, the tumor growth delay (TGD) was multiplied by 2.1 for the "TL #532" group (group-IV versus I). This anti-tumor effect is even more pronounced for the "TL #532+isotype combo" (group-V versus II), with a TGD multiplied by 3. Finally, despite the weak effect of the anti-PDL1 on tumor growth as monotherapy, the "TL #532+ anti-PDL1 combo therapy" turns out to be synergistic. The tumor growth delay is multiplied by 3·8 (group-VI versus III) against 2.1 for TL #532 in monotherapy.

(E) Kaplan Meier curves show a very significant increase in survival in the groups treated with TL #532 as compared to the control groups and a slight improvement in survival in the "TL #532+anti-PDL1 combo".

(F) Evolution of the weights of the mice in the groups IV, V and VI. Contrary to the results of the proof of concept (where a clear difference in weight gain was observed between TL #532 and Poly(I:C)), here the weights of the mice remain homogeneous and comparable. Kaplan Meier results were analyzed using Mann-Whitney U test and Log rank statistical methods. Tumor growth monitoring was analyzed using an unpaired t-test with p value 0.05 considered as significant. CR: mice in complete responders versus total treated.

CONCLUSIONS

The results show that TL #532 has an anti-tumour activity on an ectopic model of murine urothelial carcinoma, that is comparable to that induced by Poly (I:C), but showing less adverse effects, in particular with respect to the weight gain. In vivo, tumor growth delay was significantly increased. Although all the tumors of the mice on the control group progressed, one-third of the TL #532-treated mice were complete responders (with a complete disappearance of the tumor). The "rechallenge" of the complete responders using the same murine bladder cancer cells, at 3 months, prevented the tumor proliferation in ⅔ of the mice. These data favorably support the development of an anti-tumor immune memory, resulting to an anti-tumor vaccination. This effect could be explained by a maturation and invasion of memory T cells specific to the tumor site.

The ex-vivo experiments demonstrated on freshly resected tumors of patients, TL #532 induces a strong secretion of cytokines and chemokines involved in the attraction of CTL (in particular RANTES, MIG and IP10) and decreases the chemokines involved in the recruitment of T-reg and MDSC (in particular MDC and sFas). These results are correlated with the in-vivo experiments, in which a synergistic effect between the ligand TLR3 and anti-PDL1 was observed by the extension of the tumor growth delay (TGD), as compared to the TLR3 ligand or anti-PDL1 alone. Especially, the rate complete responders increased to 50% when the two treatments were combined, as opposed to about 30% when TL #532 was in monotherapy.

Both in-vivo and in-vitro data demonstrate the absence of toxicity of the TL #532. The mice were found to maintain a better growing weight curve compared to the mice treated with Poly (I:C), demonstrating an enhanced tolerance of the TL #532 compared with Poly(I:C). This result is consistent with in-vitro experiments demonstrating the absence of toxicity of TL #532 on primary human bladder cells at 24 hours up to very high doses compared with toxic effects of Poly(I:C) at very low doses. This difference in toxicity observed between the different ligands TLR3, Poly(I:C) and TL #532, is explained by the Polyvalent effect of Poly (I:C). Indeed, Poly (I:C) will act on several pattern recognition receptors such as TLR3, but also MDA5 (Melanoma Differentiation-Associated Protein 5) and RIG-I (retinoic acid-inducible gene-I-like receptors) inducing several inflammatory pathways as well as high cytokinemia thus explaining its high toxicity (Matsumoto M, et al. Biochem. Biophys. Res. Commun. 2002 and Kato H, et al. Nature. 2006). In contrast, TL #532 has a specific activity on TLR3 by means of experiments using bafilomycin or siRNAs. Currently the standard medical treatments in human urothelial carcinoma, BCG therapy in NMIBC and chemotherapy in MIBC, are poorly tolerated therapies with many adverse effects (Lamm D L, et al. J. Urol. 2000; Colombel M, et al. J. Urol. 2006; Alfred Witjes J, et al. Eur Urol. 2017). The absence of toxicity of TL #532 is a real advantage for its development in the treatment of bladder cancer.

In addition, it has been demonstrated on freshly resected tumors treated ex-vivo using TL #532 that its mechanism of action involves apoptosis of bladder cancer cells, showing apoptotic bodies as early as from 24 hours of treatment. Finally, a reprogramming of tumor microenvironment, with secretion of pro-inflammatory cytokines (including CCL5, CXCL9, CXCL10, IFN gamma, IFN lambda and TRAIL) was observed on bladder tumors when they were treated with TL #532.

The ex vivo results show that 100% of bladder tumors express TLR3. Recently, Ayari et al showed that TLR3 receptors are expressed and functional on all their normal urothelial samples (11 samples), in most of the NMIBC tissues (11 samples), and to a lesser extent in the MIBC tumors (15 samples) (Ayari C, et al. J. Urol. 2011). Another team showed in 60 bladder cell samples (24 urothelial carcinomas and 46 normal tissues), the expression of the family of TLRs (TLR-1 to 9), but did not provide accurate data related to TLR3 (Sabah-Ozcan S, et al. Urol. Oncol. 2017).

The ligands of the invention are characterized by efficacy as a monotherapy, synergism with the anti-PDL1s, a vaccine effect and low toxicity, in addition to being synthesizable.

The invention claimed is:

1. A double-stranded RNA (dsRNA) having two complementary strands, wherein the dsRNA comprises at least one block or homopolymer of poly A and the complementary block or homopolymer of poly U, each block comprising at least 15 Å, or U, and each strand having a determined length of between 50 and 200 bases, the dsRNA being of formula (III):

$$[P]_a[A]_b[R]_c$$

$$[Y]_a[U]_b[Z]_c,$$

wherein P and R are independently chosen among I and C, and Y and Z are the complementary bases, b is an integer between 20 and 100, and a and c independently are between 5 and 50.

2. A method of treatment of cancer, comprising administering to a patient in need thereof an efficient amount of the double-stranded RNA (dsRNA) according to claim 1.

3. The method according to claim 2, wherein the cancer is a cancer expressing a TLR3 receptor.

4. The method of claim 2, wherein the cancer is bladder cancer.

5. The method of claim 2, wherein the cancer is Non Muscle Invasive Bladder Cancer, Muscle Invasive Bladder Cancer, or Metastatic Muscle Invasive Bladder Cancer.

6. The method of claim 2, wherein the cancer is an epithelial cancer.

7. The method of claim 2, wherein the cancer is Lung cancer, Non-Small-Cell Lung cancer, or Breast cancer.

8. The method of claim 2, further comprising administering to said patient an efficient amount of an Immune Check Point Inhibitor.

9. The method of claim 8, wherein the Immune Check Point Inhibitor is an anti-PD-1 or an anti-PD-L1 monoclonal antibody.

10. The dsRNA according to claim 1, wherein the dsRNA is selected from:

5' (I)10-(U)50-(I)10 3'
5' (I)10-(A)50-(I)10 3'
5' (I)5-(A)60-(I)5 3'
5' (I)15-(A)40-(I)15 3'
5' (I)20-(A)30-(I)20 3'
5' (I)25-(A)20-(I)25 3'
5' (I)5-(A)50-(I)15 3'
5' (I)13-(A)64-(I)13 3'; and
5' (I)10-(A)70-(I)10 3'.

11. The dsRNA according to claim 1, wherein the A, U, I, or C are modified nucleotides comprising O-methylated nucleotides or phosphorothioate nucleotides.

12. A composition comprising the dsRNA of claim 1 and a pharmaceutically acceptable vehicle, carrier or excipient.

13. The dsRNA according to claim 1, wherein a+b+c is at least 50.

14. The dsRNA according to claim 1, wherein a+b+c is at least 60.

15. The dsRNA according to claim 1, wherein a+b+c is at least 100.

16. The dsRNA according to claim 1, wherein a+b+c is between 70 and 150.

17. The dsRNA according to claim 1, wherein b is an integer between 35 and 100.

18. The dsRNA according to claim 1, wherein b is an integer between 40 and 100.

19. The dsRNA according to claim 1, wherein b is an integer between 50 and 100.

20. The dsRNA according to claim 1, wherein b is an integer between 50 and 90.

* * * * *

SEQUENCE LISTING

<160> NUMBER OF SEQ ID NOS: 123

<210> SEQ ID NO 1
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 1
uacnucauau annnaccuau nuuaucuncn unuccaaccu uannauucac 50

<210> SEQ ID NO 2
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 2
nunaauccua annuunnaca cncanauaac auannucccu auaunacnua 50

<210> SEQ ID NO 3
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 3
ucnnucnacn caancnauua cacuccunuc acaucauaau cnuuuncuau 50

<210> SEQ ID NO 4
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 4
auancaaacn auuaunaunu nacannanun uaaucncuun cnucnaccna 50

<210> SEQ ID NO 5
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 5

-continued aaunaanuau unncanacau unanunccna acaanaccun accuaacnnu 50

<210> SEQ ID NO 6
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 6
accnuuannu cannucuunu ucnncacuca aunucuncca auacuucauu 50

<210> SEQ ID NO 7
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 7
cncunuuuuc naaauuaccc uuuauncncn nnuauunaac cacncuuaun 50

<210> SEQ ID NO 8
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 8
cauaancnun nuucaauacc cncncauaaa nnnuaauuuc naaaacancn 50

<210> SEQ ID NO 9
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 9
nnaanununn cuanaucuua ncuuacnuca cuanannnuc cacnuuuanu 50

<210> SEQ ID NO 10
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i -continued

<400> SEQUENCE: 10
acuaaacnun nacccucuan unacnuaanc uaanaucuan ccacacuucc 50

<210> SEQ ID NO 11
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 11
aanananucu cauaauacnu ccnnccncau ncncannnua uauuunnaca 50

<210> SEQ ID NO 12
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 12
unuccaaaua uacccuncnc auncnnccnn acnuauuaun anacucucuu 50

<210> SEQ ID NO 13
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 13
auanaaacua cannacuaac cuuccunnca accnnnannu nnnaauccnu 50

<210> SEQ ID NO 14
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 14
acnnauuccc accucccnnu unccannaan nuuanuccun uanuuucuau 50

<210> SEQ ID NO 15
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 15
nannannanu cnucanacca nauancuuun aunuccunau cnnaannauc 50

<210> SEQ ID NO 16
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 16
nauccuuccn aucannacau caaancuauc unnucunacn acuccuccuc 50

<210> SEQ ID NO 17
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 17
nnauacnana uccnuanauu nauaannnac acnnaauauc cccnnacnca 50

<210> SEQ ID NO 18
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 18
uncnuccnnn nauauuccnu nucccuuauc aaucuacnna ucucnuaucc 50

<210> SEQ ID NO 19
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 19
acnuucuaan anuunnacna aaunuuucnc naccuannau nannucnccc 50

<210> SEQ ID NO 20
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)

<223> OTHER INFORMATION: n=i

<400> SEQUENCE: 20
nnncnaccuc auccuannuc ncnaaacauu ucnuccaacu cuuanaacnu 50

<210> SEQ ID NO 21
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 21
uacnuancaa nnunacacaa ncacanuana uccuncccnc nuuuccuaun 50

<210> SEQ ID NO 22
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 22
cauannaaac ncnnncanna ucuacununc uununucacc uuncuacnua 50

<210> SEQ ID NO 23
<211> LENGTH: 50
<212> TYPE: RNA
<213> ORGANISM: Artificial Sequence
<220> FEATURE:
<223> OTHER INFORMATION: sense stand of  dsRNA
<220> FEATURE:
<221> NAME/KEY: misc_feature
<222> LOCATION: (1)..(50)
<223> OTHER INFORMATION: n=i

<400> SEQUENCE: 23
cuanuununn auunnauunc cauucuccna nunuauuacc nunacnnccn 50

<210> SEQ ID NO 24
<211> LENGTH: 50
<212> TYPE: RNA
<213> ORGANISM: Artificial Sequence
<220> FEATURE:
<223> OTHER INFORMATION: antisense strand of  dsRNA
<220> FEATURE:
<221> NAME/KEY: misc_feature
<222> LOCATION: (1)..(50)
<223> OTHER INFORMATION: n=i

<400> SEQUENCE: 24
cnnccnucac nnuaauacac ucnnanaaun ncaauccaau ccacaacuan 50

<210> SEQ ID NO 25
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 25
cacnnnuccc aunuaaunca nucnuanccu accunacunu acuunnaanu 50

<210> SEQ ID NO 26
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 26
acuuccaanu acanucannu anncuacnac uncauuacau nnnacccnun 50

<210> SEQ ID NO 27
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 27
naccnnacna accacananc ncunnaanaa ucucuancun cuuuacaaan 50

<210> SEQ ID NO 28
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 28
cuuunuaaan cancuanana uucuuccanc ncucununnu ucnuccnnuc 50

<210> SEQ ID NO 29
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 29
uuucccacun ccuuaanccn ncuuncccuu ucunccunua nauccauunn 50

<210> SEQ ID NO 30
<211> LENGTH: 50
<212> TYPE: RNA
<213> ORGANISM: Artificial Sequence
<220> FEATURE:
<223> OTHER INFORMATION: antisense strand of dsRNA
<220> FEATURE:

-continued

<221> NAME/KEY: misc_feature
<222> LOCATION: (1)..(50)
<223> OTHER INFORMATION: n=i

<400> SEQUENCE: 30
ccaaunnauc uacanncana aannncaanc cnncuuaann canunnnaaa 50

<210> SEQ ID NO 31
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 31
ncaacuucna nnaccuaaun unaccnaccu anauucnnca uununnncan 50

<210> SEQ ID NO 32
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 32
cuncccacaa unccnaaucu annucnnuca cauuannucc ucnaanuunc 50

<210> SEQ ID NO 33
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 33
naucuaunnc nunanacccn uuauncucca uuacnnucan unnnucacan 50

<210> SEQ ID NO 34
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 34
cununaccca cunaccnuaa unnancauaa cnnnucucac nccauanauc 50

<210> SEQ ID NO 35
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 35
acuncnacnu ucuaaacnuu nnuccnucan aancnccauc cannaucacn 50

<210> SEQ ID NO 36
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 36
cnunauccun naunncncuu cunacnnacc aacnuuuana acnucncanu 50

<210> SEQ ID NO 37
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 37
acunnuncca acncncannc auanuucnan nanaauuauc cnnnnncaau 50

<210> SEQ ID NO 38
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 38 auunccccn nauaauucuc cucnaacuau nccuncncnu unncaccanu 50

<210> SEQ ID NO 39
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 39
nacaaccanc aucucnnnuc uuncccaacc cnucuacacn cunuuauanc 50

<210> SEQ ID NO 40
<211> LENGTH: 50
<212> TYPE: RNA
<213> ORGANISM: Artificial Sequence
<220> FEATURE:

<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 40
ncuauaacan cnunuanacn nnuunnncaa nacccnanau ncunnuunuc 50

<210> SEQ ID NO 41
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 41
cauncuancn uncnnnnuac acuuncuaac cauuunnnac acnnnacacu 50

<210> SEQ ID NO 42
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 42
anunucccnu nucccaaaun nuuancaanu nuaccccnca cncuancaun 50

<210> SEQ ID NO 43
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 43
auanacnnac ancuunnuau ccunancaca nucncncnuc cnaaucuanc 50

<210> SEQ ID NO 44
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 44
ncuanauucn nacncncnac ununcucann auaccaancu nuccnucuau 50

<210> SEQ ID NO 45
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 45
uacccauacu ccaccnuunn cannnnnauc ncaunuccca cnunaaacau 50

<210> SEQ ID NO 46
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 46
aunuuucacn unnnacaunc naucccccun ccaacnnunn anuaunnnua 50

<210> SEQ ID NO 47
<211> LENGTH: 50
<212> TYPE: RNA
<213> ORGANISM: Artificial Sequence
<220> FEATURE:
<223> OTHER INFORMATION: sense stand of dsRNA
<220> FEATURE:
<221> NAME/KEY: misc_feature
<222> LOCATION: (1)..(50)
<223> OTHER INFORMATION: n=i

<400> SEQUENCE: 47
anuacaanac uanccuuncu ancaaccncn nncunnnanc cuaannuauc 50

<210> SEQ ID NO 48
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 48
nauaccuuan ncucccancc cncnnuuncu ancaanncua nucuunuacu 50

<210> SEQ ID NO 49
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 49
uucancncnc anncuunnnu cnanauaaaa ucuccanunc ccaanaccac 50

<210> SEQ ID NO 50
<211> LENGTH: 50
<212> TYPE: RNA

<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 50
nunnucuunn ncacunnana uuuuaucucn acccaanccu ncncncunaa 50

<210> SEQ ID NO 51
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 51
ncaacnnaac nuccuuancu ccnncannca auuaannnna acncaancau 50

<210> SEQ ID NO 52
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 52
auncuuncnu uccccuuaau unccunccnn ancuaannac nuuccnuunc 50

<210> SEQ ID NO 53
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 53
nuaucauunu ncaccunccn nunaccacuc aacnaununn nnacnccnuu 50

<210> SEQ ID NO 54
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 54
aacnncnucc ccacaucnuu nanunnucac cnncannunc acaaunauac 50

<210> SEQ ID NO 55
<211> LENGTH: 50

<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 55
nuuacccaua unnuccacan nacacucnuc ncuuccnnnc uuncccucua 50

<210> SEQ ID NO 56
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 56
uanannncaa ncccnnaanc nacnanunuc cununnacca uaunnnuaac 50

<210> SEQ ID NO 57
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 57
acncunucuc unncacnunn nunnccuana nnaaucacau ccaanccunn 50

<210> SEQ ID NO 58
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 58
ccanncuunn aununauucc ucuannccac ccacnuncca nanacancnu 50

<210> SEQ ID NO 59
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 59
nucnunncaa unuucnucun nnununnucu acacaauncn nncnnuncnu 50

<210> SEQ ID NO 60

-continued

<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 60
acncaccncc cncauununu anaccacacc canacnaaca uunccacnac 50

<210> SEQ ID NO 61
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 61
unncanacac accnunaccc cnccucucca uunaunccac nncnaaunuc 50

<210> SEQ ID NO 62
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 62
nacauucncc nunncaucaa unnanannen nnnucacnnu nunucuncca 50

<210> SEQ ID NO 63
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 63
ancccuucuc cccuncnncc acncccnuan anaucacncc uuunacccuc 50

<210> SEQ ID NO 64
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 64
nannnucaaa nncnunaucu cuacnnncnu nnccncannn nanaannncu 50

<210> SEQ ID NO 65
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 65
acncuncann acuuncaacc nnncanacuc nncnncannu ccuanuncan 50

<210> SEQ ID NO 66
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 66
cuncacuann accunccncc nanucunccc nnuuncaanu ccuncancnu 50

<210> SEQ ID NO 67
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 67
nncnaanncc cuaacnnnan auacncnccc acaacucnnc ncnaauacnn 50

<210> SEQ ID NO 68
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 68
ccnuauucnc nccnanuunu nnncncnuau cucccnuuan nnccuucncc 50

<210> SEQ ID NO 69
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 69
ncaccanauc unuaannucc nccacncana cnannccnnn cnnanaccac 50

<210> SEQ ID NO 70
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 70
nunnucuccn cccnnccucn ucuncnunnc nnaccuuaca naucunnunc 50

<210> SEQ ID NO 71
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 71
uccunnanna nnnncnnaua nccucuuacc cnuncccac cnuunncnnu 50

<210> SEQ ID NO 72
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 72
accnccaacn nunnnncacn nnuaanannc uauccncccc uccuccanna 50

<210> SEQ ID NO 73
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 73
uncnccnnuc cccanccncn cucauncucn ncaccnccau aaccanaccn 50

<210> SEQ ID NO 74
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 74
cnnucunnuu aunncnnunc cnancaunan cncnncunnn naccnncnca 50

<210> SEQ ID NO 75
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 75
uanccncccc unnnccncnn uccncuaccu uncannaauc nannccnucc 50

<210> SEQ ID NO 76
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 76
nnacnnccuc nauuccunca annuancnna ccncnnccca nnnncnncua 50

<210> SEQ ID NO 77
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 77
ncuncuucnn cnccccnnnc ncaccccunc cncnnnnncn nnaucncccn 50

<210> SEQ ID NO 78
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 78
cnnncnaucc cncccccncn ncannnnunc ncccnnnncn ccnaancanc 50

<210> SEQ ID NO 79
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 79

-continued nucnncnccc nnccccccnn ccccncancn nncuccccnc ccnnnccncc 50

<210> SEQ ID NO 80
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 80
nncnncccnn ncnnnnancc cncuncnnnn ccnnnnnncc nnncnccnac 50

<210> SEQ ID NO 81
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 81
nnnnnnccca cncnncnncn ccnccnncnc ccccnnnncn ccccncnucn 50

<210> SEQ ID NO 82
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 82
cnacncnnnn cnccccnnnn ncnccnncnn cnccnccncn unnncccccc 50

<210> SEQ ID NO 83
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 83
cnnnccnncn nnnnncnnnc nnnnnccccu nncccncccn ncnccccncn 50

<210> SEQ ID NO 84
<211> LENGTH: 50
<212> TYPE: RNA
<213> ORGANISM: Artificial Sequence
<220> FEATURE:
<223> OTHER INFORMATION: antisense strand dsRNA
<220> FEATURE:
<221> NAME/KEY: misc_feature
<222> LOCATION: (1)..(50)
<223> OTHER INFORMATION: n=i

<400> SEQUENCE: 84
cncnnnncnc cnnncnnncc annnnccccc ncccnccccc cnccnncccn 50

<210> SEQ ID NO 85
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 85
nnnccnnnnc nncccennnc nncnnccncc nnccccnncn ncnnnncncc 50

<210> SEQ ID NO 86
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 86
nncnccccnc cnccnnnncc nncnnccncc ncccnnnncc nccccnnccc 50

<210> SEQ ID NO 87
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 87
nnauannnnc nnccccnnnc nncnnccncc nnccccnncn ncnnnncnuu 50

<210> SEQ ID NO 88
<211> LENGTH: 50
<212> TYPE: RNA
<213> ORGANISM: Artificial Sequence
<220> FEATURE:
<223> OTHER INFORMATION: antisense strand of dsRNA
<220> FEATURE:
<221> NAME/KEY: misc_feature
<222> LOCATION: (1)..(50)
<223> OTHER INFORMATION: n=i

<400> SEQUENCE: 88
aacnccccnc cnccnnnncc nncnnccncc ncccnnnncc nccccuaucc 50

<210> SEQ ID NO 89
<211> LENGTH: 50
<212> TYPE: RNA
<213> ORGANISM: Artificial Sequence
<220> FEATURE:
<223> OTHER INFORMATION: sense strand of dsRNA

<400> SEQUENCE: 89
auuuaaaaaa uaaauauaau aaaauauaau uuaauuaauu auuuauuaau 50

-continued

<210> SEQ ID NO 90
<211> LENGTH: 50
<212> TYPE: RNA
<213> ORGANISM: Artificial Sequence
<220> FEATURE:
<223> OTHER INFORMATION: antisense strand of dsRNA

<400> SEQUENCE: 90
auuaauaaau aauuaauuaa auuauauuuu auuauauuua uuuuuuaaau 50

<210> SEQ ID NO 91
<211> LENGTH: 50
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(50)
<223> OTHER INFORMATION: n=i

<400> SEQUENCE: 91
nnnnnnnnnn nnnnnnnnnn nnnnnnnnnn nnnnnnnnnn nnnnnnnnnn 50

<210> SEQ ID NO 92
<211> LENGTH: 50
<212> TYPE: RNA
<213> ORGANISM: Artificial Sequence
<220> FEATURE:
<223> OTHER INFORMATION: antisense strand of dsRNA

<400> SEQUENCE: 92
cccccccccc cccccccccc cccccccccc cccccccccc cccccccccc 50

<210> SEQ ID NO 93
<211> LENGTH: 50
<212> TYPE: RNA
<213> ORGANISM: Artificial Sequence
<220> FEATURE:
<223> OTHER INFORMATION: sense strand of dsRNA

<400> SEQUENCE: 93
aaaaaaaaaa aaaaaaaaaa aaaaaaaaaa aaaaaaaaaa aaaaaaaaaa 50

<210> SEQ ID NO 94
<211> LENGTH: 50
<212> TYPE: RNA
<213> ORGANISM: Artificial Sequence
<220> FEATURE:
<223> OTHER INFORMATION: antisense strand of dsRNA

<400> SEQUENCE: 94
uuuuuuuuuu uuuuuuuuuu uuuuuuuuuu uuuuuuuuuu uuuuuuuuuu 50

<210> SEQ ID NO 95
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 95
nnnnnnnnnn uuuuuuuuuu uuuuuuuuuu uuuuuuuuuu uuuuuuuuuu uuuuuuuuuu 60 nnnnnnnnnn 70

<210> SEQ ID NO 96
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 96
nnnnnaaaaa aaaaaaaaaa aaaaaaaaaa aaaaaaaaaa aaaaaaaaaa aaaaaaaaaa 60 aaaaannnnn 70

<210> SEQ ID NO 97
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 97
nnnnnnnnnn nnnnnaaaaa aaaaaaaaaa aaaaaaaaaa aaaaaaaaaa aaaaannnnn 60 nnnnnnnnnn 70

<210> SEQ ID NO 98
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 98
nnnnnnnnnn nnnnnnnnnn aaaaaaaaaa aaaaaaaaaa aaaaaaaaaa nnnnnnnnnn 60 nnnnnnnnnn 70

<210> SEQ ID NO 99
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 99
nnnnnnnnnn nnnnnnnnnn nnnnnaaaaa aaaaaaaaaa aaaaannnnn nnnnnnnnnn 60 nnnnnnnnnn 70

<210> SEQ ID NO 100
<211> LENGTH: 70
<212> TYPE: RNA

-continued

<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 100
nnnnnaaaaa aaaaaaaaaa aaaaaaaaaa aaaaaaaaaa aaaaaaaaaa aaaaannnnn 60 nnnnnnnnnn 70

<210> SEQ ID NO 101
<211> LENGTH: 90
<212> TYPE: RNA
<213> ORGANISM: Artificial Sequence
<220> FEATURE:
<223> OTHER INFORMATION: Sense strand of dsRNA
<220> FEATURE:
<221> NAME/KEY: misc_feature
<222> LOCATION: (1)..(90)
<223> OTHER INFORMATION: n=i

<400> SEQUENCE: 101
nnnnnnnnnn nnnaaaaaaa aaaaaaaaaa aaaaaaaaaa aaaaaaaaaa aaaaaaaaaa 60
aaaaaaaaaa aaaaaaannn nnnnnnnnnn 90

<210> SEQ ID NO 102
<211> LENGTH: 90
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(90)
<223> OTHER INFORMATION: n=i

<400> SEQUENCE: 102
nnnnnnnnnn aaaaaaaaaa aaaaaaaaaa aaaaaaaaaa aaaaaaaaaa aaaaaaaaaa 60
aaaaaaaaaa aaaaaaaaaa nnnnnnnnnn 90

<210> SEQ ID NO 103
<211> LENGTH: 60
<212> TYPE: RNA
<213> ORGANISM: Artificial Sequence
<220> FEATURE:
<223> OTHER INFORMATION: sense strand of dsRNA

<400> SEQUENCE: 103
aaaaaaaaaa aaaaaaaaaa aaaaaaaaaa aaaaaaaaaa aaaaaaaaaa aaaaaaaaaa 60

<210> SEQ ID NO 104
<211> LENGTH: 60
<212> TYPE: RNA
<213> ORGANISM: Artificial Sequence
<220> FEATURE:
<223> OTHER INFORMATION: antisense strand of dsRNA

<400> SEQUENCE: 104
uuuuuuuuuu uuuuuuuuuu uuuuuuuuuu uuuuuuuuuu uuuuuuuuuu uuuuuuuuuu 60

<210> SEQ ID NO 105
<211> LENGTH: 70
<212> TYPE: RNA
<213> ORGANISM: Artificial Sequence
<220> FEATURE:
<223> OTHER INFORMATION: sense strand of dsRNA

<400> SEQUENCE: 105
aaaaaaaaaa aaaaaaaaaa aaaaaaaaaa aaaaaaaaaa aaaaaaaaaa aaaaaaaaaa 60
aaaaaaaaaa 70

<210> SEQ ID NO 106
<211> LENGTH: 70
<212> TYPE: RNA
<213> ORGANISM: Artificial Sequence
<220> FEATURE:
<223> OTHER INFORMATION: antisense strand of dsRNA

<400> SEQUENCE: 106
uuuuuuuuuu uuuuuuuuuu uuuuuuuuuu uuuuuuuuuu uuuuuuuuuu uuuuuuuuuu 60
uuuuuuuuuu 70

<210> SEQ ID NO 107
<211> LENGTH: 80
<212> TYPE: RNA
<213> ORGANISM: Artificial Sequence
<220> FEATURE:
<223> OTHER INFORMATION: sense strand of dsRNA

<400> SEQUENCE: 107
aaaaaaaaaa aaaaaaaaaa aaaaaaaaaa aaaaaaaaaa aaaaaaaaaa aaaaaaaaaa 60
aaaaaaaaaa aaaaaaaaaa 80

<210> SEQ ID NO 108
<211> LENGTH: 80
<212> TYPE: RNA
<213> ORGANISM: Artificial Sequence
<220> FEATURE:
<223> OTHER INFORMATION: Antisense strand of dsRNA

<400> SEQUENCE: 108
uuuuuuuuuu uuuuuuuuuu uuuuuuuuuu uuuuuuuuuu uuuuuuuuuu uuuuuuuuuu 60
uuuuuuuuuu uuuuuuuuuu 80

<210> SEQ ID NO 109
<211> LENGTH: 90
<212> TYPE: RNA
<213> ORGANISM: Artificial Sequence
<220> FEATURE:
<223> OTHER INFORMATION: sense strand of dsRNA

<400> SEQUENCE: 109
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa 90

<210> SEQ ID NO 110
<211> LENGTH: 90
<212> TYPE: RNA
<213> ORGANISM: Artificial Sequence
<220> FEATURE:
<223> OTHER INFORMATION: antisense strand of dsRNA

<400> SEQUENCE: 110
uuuuuuuuuu uuuuuuuuuu uuuuuuuuuu uuuuuuuuuu uuuuuuuuuu uuuuuuuuuu 60
uuuuuuuuuu uuuuuuuuuu uuuuuuuuuu 90

```
<210> SEQ ID NO 111
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 111

nnnnnnnnnn aaaaaaaaaa aaaaaaaaaa aaaaaaaaaa aaaaaaaaaa aaaaaaaaaa     60

nnnnnnnnnn                                                             70


<210> SEQ ID NO 112
<211> LENGTH: 70
<212> TYPE: RNA
<213> ORGANISM: Artificial Sequence
<220> FEATURE:
<223> OTHER INFORMATION: antisense strand of dsRNA

<400> SEQUENCE: 112

cccccccccc uuuuuuuuuu uuuuuuuuuu uuuuuuuuuu uuuuuuuuuu uuuuuuuuuu     60

cccccccccc                                                             70


<210> SEQ ID NO 113
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 113

aaaaaaaaaa aaaaaaaaaa aaaaaaaaaa aaaaannnnn nnnnnnnnnn nnnnnnnnnn     60

nnnnnnnnnn                                                             70


<210> SEQ ID NO 114
<211> LENGTH: 70
<212> TYPE: RNA
<213> ORGANISM: Artificial Sequence
<220> FEATURE:
<223> OTHER INFORMATION: antisense strand of dsRNA

<400> SEQUENCE: 114

uuuuuuuuuu uuuuuuuuuu uuuuuuuuuu uuuuuccccc cccccccccc cccccccccc     60

cccccccccc                                                             70


<210> SEQ ID NO 115
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 115

aaaaaaaaaa nnnnnnnnnn nnnnnnnnnn nnnnnnnnnn nnnnnnnnnn nnnnnnnnnn     60
```

-continued aaaaaaaaaa 70

<210> SEQ ID NO 116
<211> LENGTH: 70
<212> TYPE: RNA
<213> ORGANISM: Artificial Sequence
<220> FEATURE:
<223> OTHER INFORMATION: antisense strand of dsRNA

<400> SEQUENCE: 116
uuuuuuuuuu cccccccccc cccccccccc cccccccccc cccccccccc cccccccccc 60
uuuuuuuuuu 70

<210> SEQ ID NO 117
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 117
nnnnnnnnnn nnnnnnnnnn nnnnnnnnnn nnnnnnnnnn nnnnnnnnnn nnnnnnnnnn 60 nnnnnnnnnn 70

<210> SEQ ID NO 118
<211> LENGTH: 70
<212> TYPE: RNA
<213> ORGANISM: Artificial Sequence
<220> FEATURE:
<223> OTHER INFORMATION: antisense strand of dsRNA

<400> SEQUENCE: 118
cccccccccc cccccccccc cccccccccc cccccccccc cccccccccc cccccccccc 60
cccccccccc 70

<210> SEQ ID NO 119
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 119
aaaaaaaaaa aaaaaaaaaa aaaaaaaaaa aaaaaaaaaa aaaaaaaaaa aaaaaaaaaa 60 nnnnnnnnnn 70

<210> SEQ ID NO 120
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i -continued

```
<400> SEQUENCE: 120

aaaaaaaaaa aaaaaaaaaa aaaaaaaaaa aaaaaaaaaa aaaaaaaaaa nnnnnnnnnn      60

nnnnnnnnnn                                                             70


<210> SEQ ID NO 121
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 121

aaaaaaaaaa aaaaaaaaaa nnnnnnnnnn nnnnnnnnnn nnnnnnnnnn nnnnnnnnnn      60

nnnnnnnnnn                                                             70


<210> SEQ ID NO 122
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 122

aaaaaaaaaa nnnnnnnnnn nnnnnnnnnn nnnnnnnnnn nnnnnnnnnn nnnnnnnnnn      60

nnnnnnnnnn                                                             70


<210> SEQ ID NO 123
<211> LENGTH: 70
<212> TYPE: RNA
<213> ORGANISM: Artificial Sequence
<220> FEATURE:
<223> OTHER INFORMATION: sense strand of dsRNA
<220> FEATURE:
<221> NAME/KEY: misc_feature
<222> LOCATION: (1)..(70)
<223> OTHER INFORMATION: n=i

<400> SEQUENCE: 123

nnnnnnnnnn nnnnnnnnnn nnnnnnnnnn aaaaaaaaaa nnnnnnnnnn nnnnnnnnnn      60

nnnnnnnnnn                                                             70
```